(12) United States Patent
Cali et al.

(10) Patent No.: US 9,273,343 B2
(45) Date of Patent: *Mar. 1, 2016

(54) COMPOUNDS AND METHODS FOR ASSAYING REDOX STATE OF METABOLICALLY ACTIVE CELLS AND METHODS FOR MEASURING NAD(P)/NAD(P)H

(75) Inventors: James J. Cali, Verona, WI (US); Sarah Duellman, Fitchburg, WI (US); Dieter Klaubert, Arroyo Grande, CA (US); Donna Leippe, Middleton, WI (US); Martha O'Brien, Madison, WI (US); John Shultz, Verona, WI (US); Jolanta Vidugiriene, Fitchburg, WI (US); Wenhui Zhou, Santa Maria, CA (US); Mary Sobol, McFarland, WI (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,579

(22) Filed: Aug. 31, 2012

(65) Prior Publication Data

US 2013/0130289 A1 May 23, 2013

Related U.S. Application Data

(60) Provisional application No. 61/530,559, filed on Sep. 2, 2011.

(51) Int. Cl.
| | |
|---|---|
| C07D 417/04 | (2006.01) |
| C07D 277/68 | (2006.01) |
| C07D 487/04 | (2006.01) |
| C12Q 1/32 | (2006.01) |
| C07D 493/10 | (2006.01) |
| C12Q 1/66 | (2006.01) |
| C07D 497/10 | (2006.01) |
| C07F 9/6558 | (2006.01) |
| C07F 9/6561 | (2006.01) |
| G01N 21/76 | (2006.01) |
| G01N 33/50 | (2006.01) |
| G01N 33/573 | (2006.01) |
| G01N 33/58 | (2006.01) |

(52) U.S. Cl.
CPC ............... *C12Q 1/32* (2013.01); *C07D 277/68* (2013.01); *C07D 417/04* (2013.01); *C07D 487/04* (2013.01); *C07D 493/10* (2013.01); *C07D 497/10* (2013.01); *C07F 9/6561* (2013.01); *C07F 9/65583* (2013.01); *C12Q 1/66* (2013.01); *G01N 21/763* (2013.01); *G01N 33/5038* (2013.01); *G01N 33/5735* (2013.01); *G01N 33/582* (2013.01)

(58) Field of Classification Search
USPC ......................................... 548/178; 544/350
See application file for complete search history.

(56) References Cited

U.S. PATENT DOCUMENTS

| | | | |
|---|---|---|---|
| 5,683,888 A * | 11/1997 | Campbell | ........................ 435/8 |
| 5,998,204 A | 12/1999 | Tsien et al. | |
| 7,378,255 B2 * | 5/2008 | Horn et al. | ...................... 435/25 |
| 7,807,402 B2 | 10/2010 | Horn et al. | |
| 2007/0015790 A1 * | 1/2007 | Cali et al. | ...................... 514/314 |
| 2008/0248511 A1 | 10/2008 | Daily et al. | |
| 2010/0047839 A1 | 2/2010 | Huang et al. | |
| 2012/0107849 A1 | 5/2012 | Klaubert et al. | |

FOREIGN PATENT DOCUMENTS

| | | |
|---|---|---|
| JP | 08-059686 | 3/1996 |
| JP | H08-294397 | 11/1996 |
| WO | 03/040100 | 5/2003 |
| WO | 03/066611 | 8/2003 |
| WO | 2013/033515 | 3/2013 |

OTHER PUBLICATIONS

Huang et al., Biosensors & Bioelectronics, (2008), 23(12), pp. 1793-1798.*
Goto, Pure and Applied Chemistry (1968), 17(3-41}, pp. 421-441.*
Fieser, L., et al., "Fieser and Fieser's Reagents for Organic Synthesis," John Wiley and Sons (1994), Cover and Content pages only.
Greene, T.W., et al., "Protective Groups in Organic Synthesis," 2d. Ed., John Wiley and Sons (1991), Table of Content pages only.
International Union of Pure and Applied Chemistry "Definitive Rules for Nomenlature of Organic Chemistry" J. Am. Chem. Soc. 1960, 82, 5545-5574.
Larock, R., "Comprehensive Organic Transformations, A Guide to Functional Group Preparation"s VCH Publishers (1989), Table of Content pages only.
Paquette, L., ed., "Encyclopedia of Reagents for Organic Synthesis," John Wiley and Sons (1995), Cover pages only.
Paquette, Leo A.; "Principles of Modem Heterocyclic Chemistry" (W.A. Benjamin, New York, 1968), particularly Chapters 1, 3, 4, 6, 7, 9. Table of Content pages only.
Weissberger, A., ed., "The Chemistry of Heterocyclic Compounds, A Series of Monographs," (John Wiley & Sons, New York, 1950 to present), in particular vols. 13, 14, 16, 19, and 28. Table of Content pages only.
PCT/US2012/053310 International Search Report and Written Opinion dated Dec. 18, 2012 (13 pages).
Silvers, W.C., et al., "Shedding light by cancer redox—human NAD(P)H: quinone oxidoreductase 1 activation of a cloaked fluorescent dye" Chemical Communications, vol. 47, 2011, 11264-11266. Sep. 19, 2011.
United States Patent Office Action for U.S. Appl. No. 14/032,420 dated Mar. 25, 2015 (19 pages).

(Continued)

*Primary Examiner* — Laura L. Stockton
(74) *Attorney, Agent, or Firm* — Michael Best & Friedrich LLP

(57) ABSTRACT

The present invention provides compounds and methods for assaying redox state of metabolically active cells and methods for assaying enzyme activity and/or metabolite level by coupling to redox defining co-factor NAD(P)/NAD(P)H measurement.

7 Claims, 43 Drawing Sheets

(56) References Cited

OTHER PUBLICATIONS

Oxford Dictionary of Biochemistry and Molecular Biology. Diaphorase. Oxford University Press. Second Edition. 2006. The General Editors. New York, New York, p. 178.

Inoue et al. Chemical studies of myctophina fish bioluminescence, Chemistry Letters (1987), (2), 417-18.

Mitani et al., "Enhancement effect of 2, 6-0-dimethyl-cyclodextrin on the chemiluminescent detection of -D-galactosidase using a Cypridina luceferin analog" Analytical Sciences (1995) 11(6), 1013-15.

United States Patent Office Action for U.S. Appl. No. 13/287,519 dated Feb. 27, 2015 (8 pages).

United States Patent Office Action for U.S. Appl. No. 13/287,519 dated Jul. 2, 2014 (10 pages).

United States Patent Office Action for U.S. Appl. No. 13/287,519 dated Nov. 7, 2014 (7 pages).

United States Patent Office Final Rejection for U.S. Appl. No. 13/287,519 dated Apr. 24, 2013 (10 pages).

United States Patent Office Final Rejection for U.S. Appl. No. 13/287,519 dated Sep. 6, 2013 (8 pages).

United States Patent Office Notice of Allowance for U.S. Appl. No. 13/287,519 dated Jun. 5, 2015 (5 pages).

Mitani, M. et al., "Chemiluminescent assay of beta-D-galactosidase using cypridina luciferin analogue: 3-(Beta-D-galactopyranosyloxy)-6-(4-methoxyphenyl)-2-methyl-imidazol[1,2-alpha]pyrazine," Anal. Sci. (1994) 10(50:813-814.

Hawkins, et al., "Bright Light, No Lysis," Promega, 2005, pp. 10-14.

\* cited by examiner

FIG. 6a: 4412
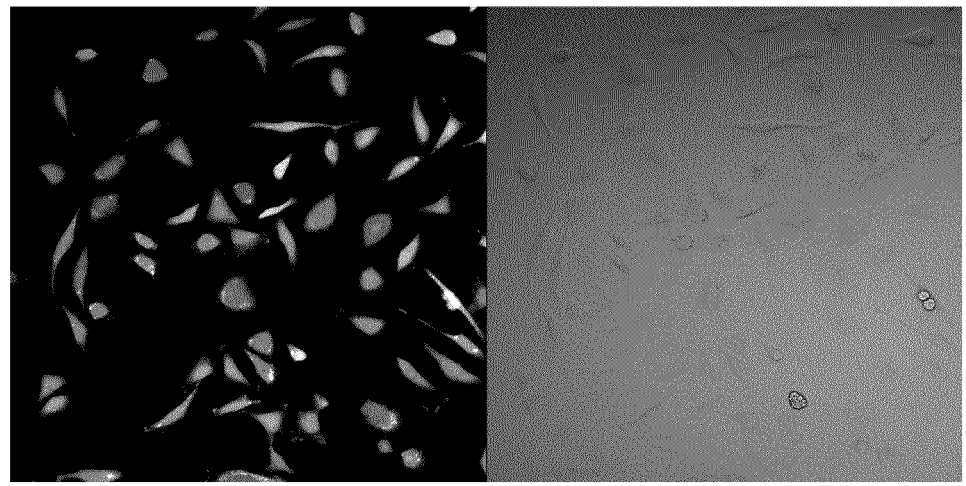
FIG. 6b: 4413
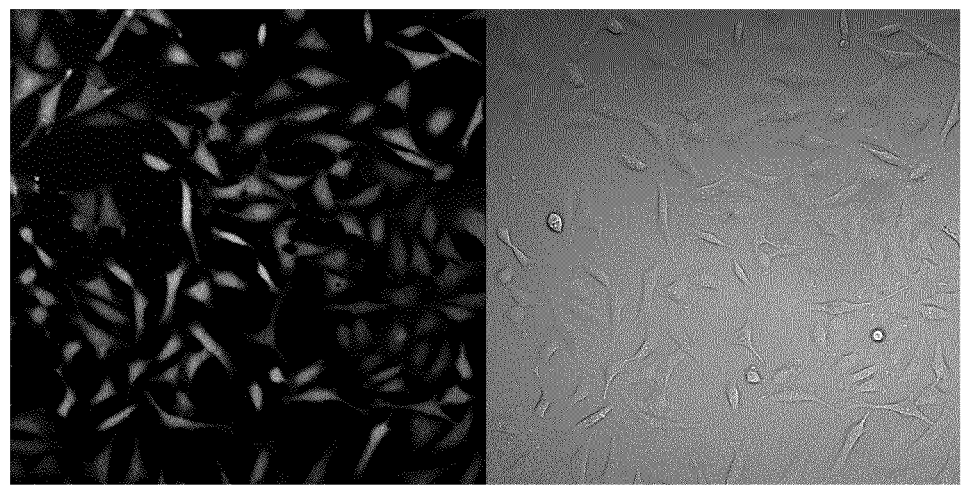

FIG. 6c: 4440
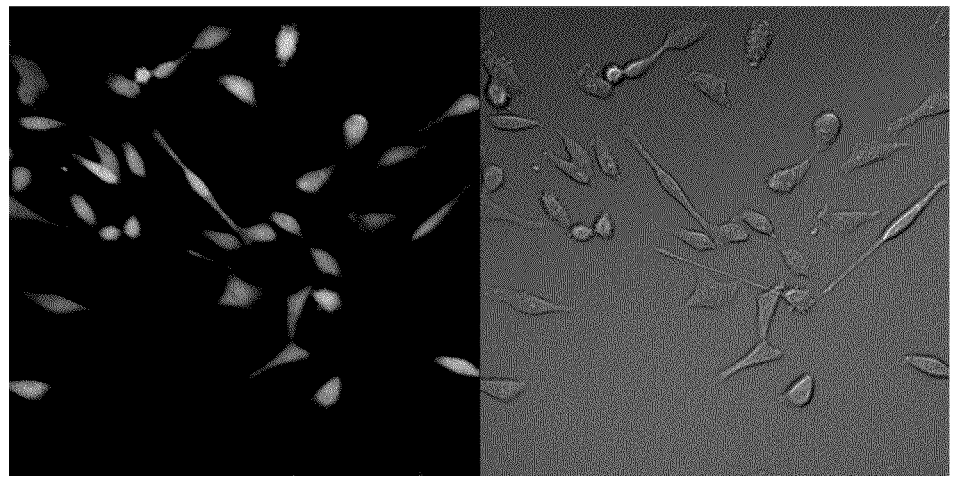
FIG. 6d: 4441
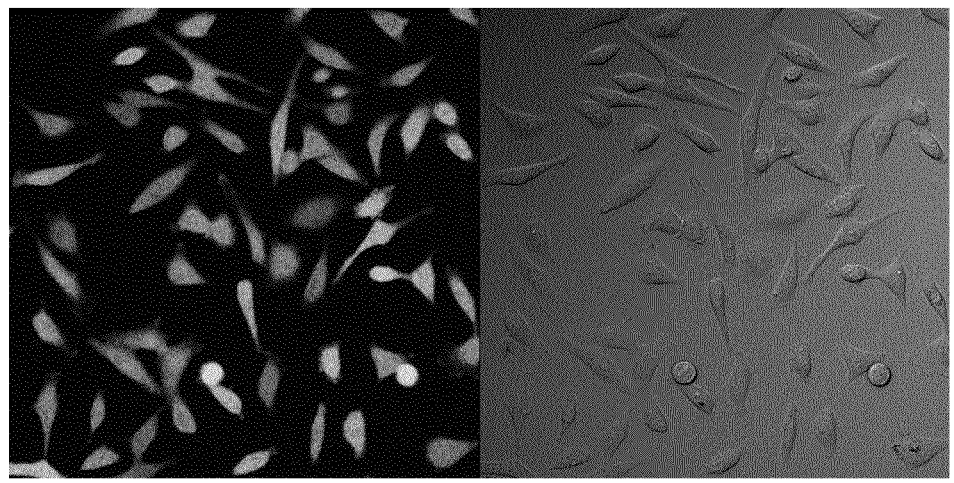

FIG. 8a-b
Control: 4543 alone
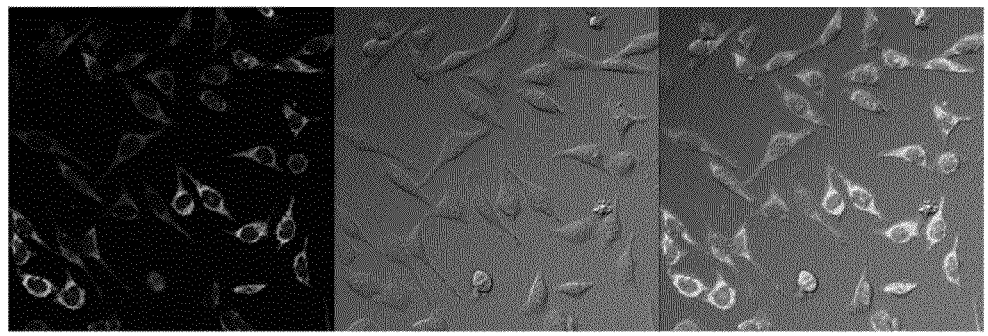
6.8mM 3-NPA added 30 minutes after 4543
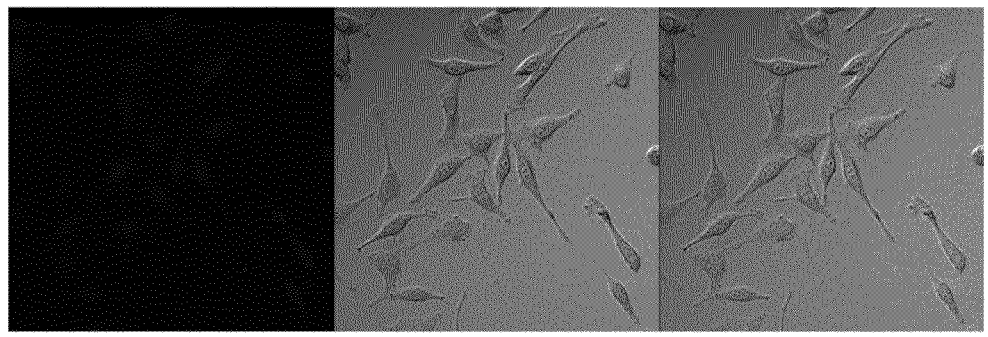

FIG. 8c-d
Control: 4547 alone
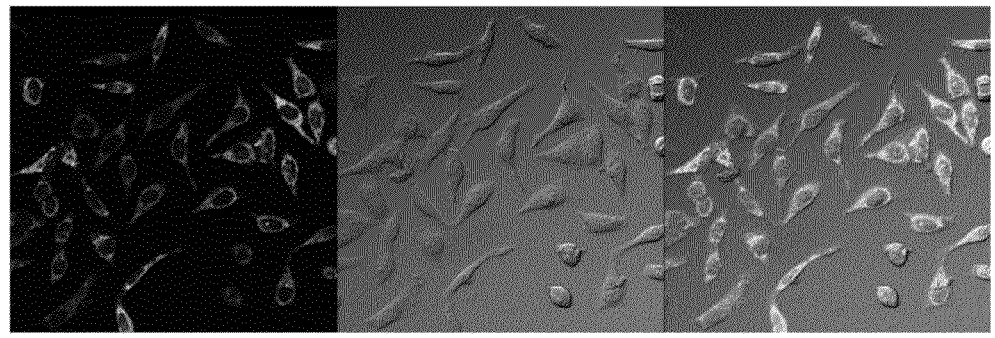
6.8mM 3-NPA added 30 minutes after 4547
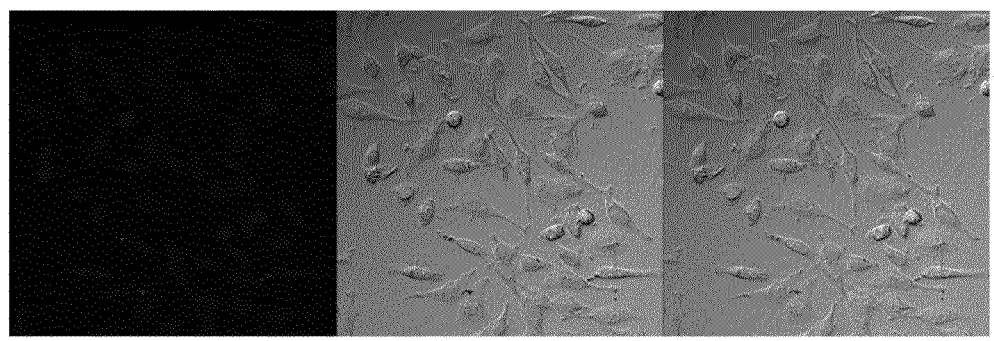

FIG. 13a(C)
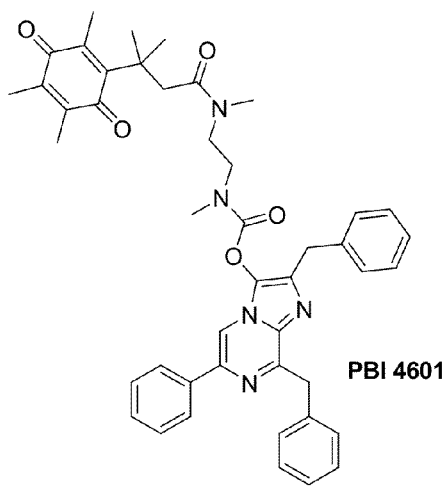
PBI 4601
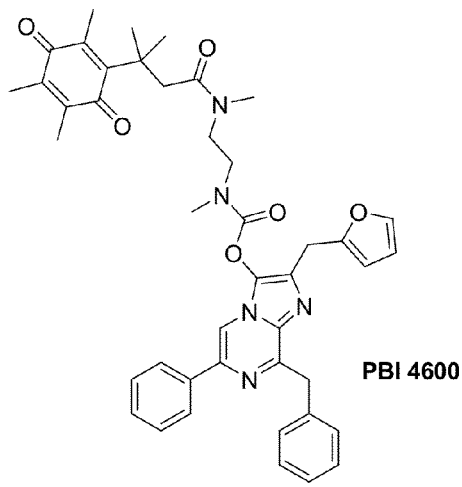
PBI 4600
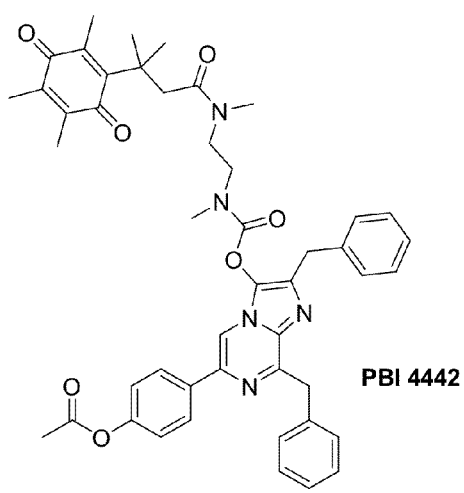
PBI 4442

FIG. 13b(B)
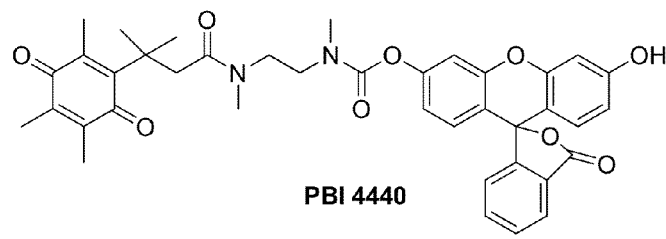
PBI 4440
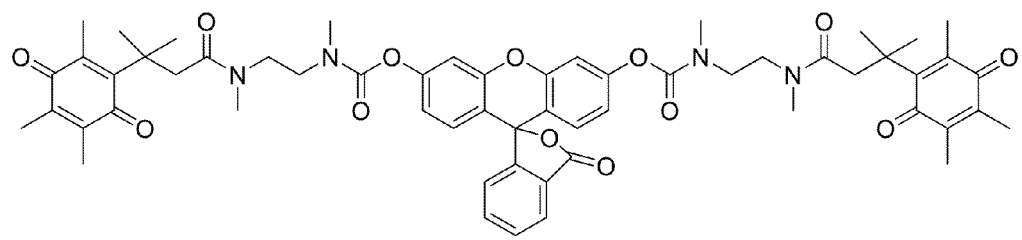
PBI 4441
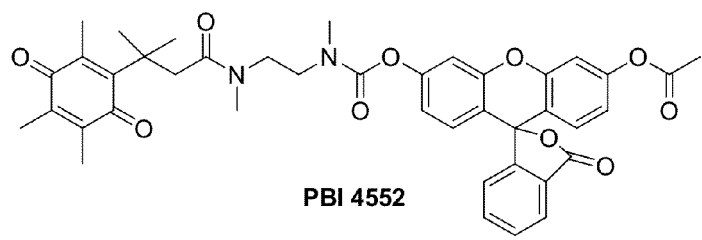
PBI 4552
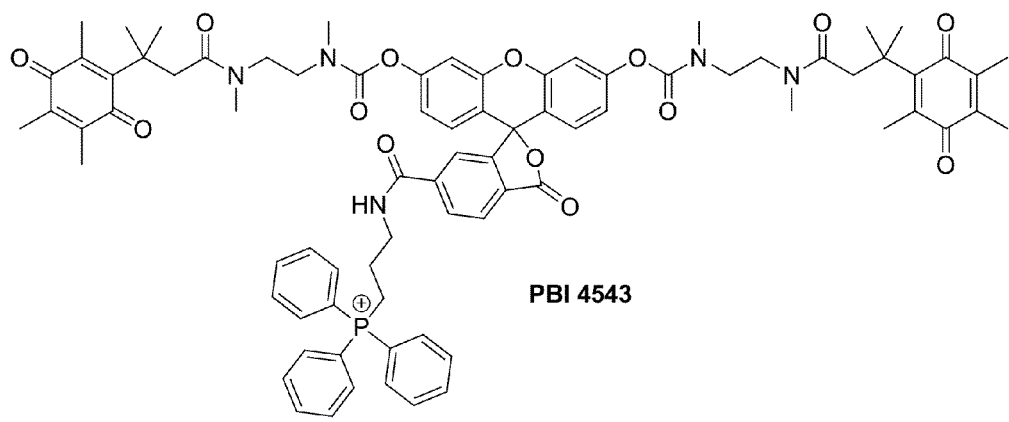
PBI 4543

FIG. 26
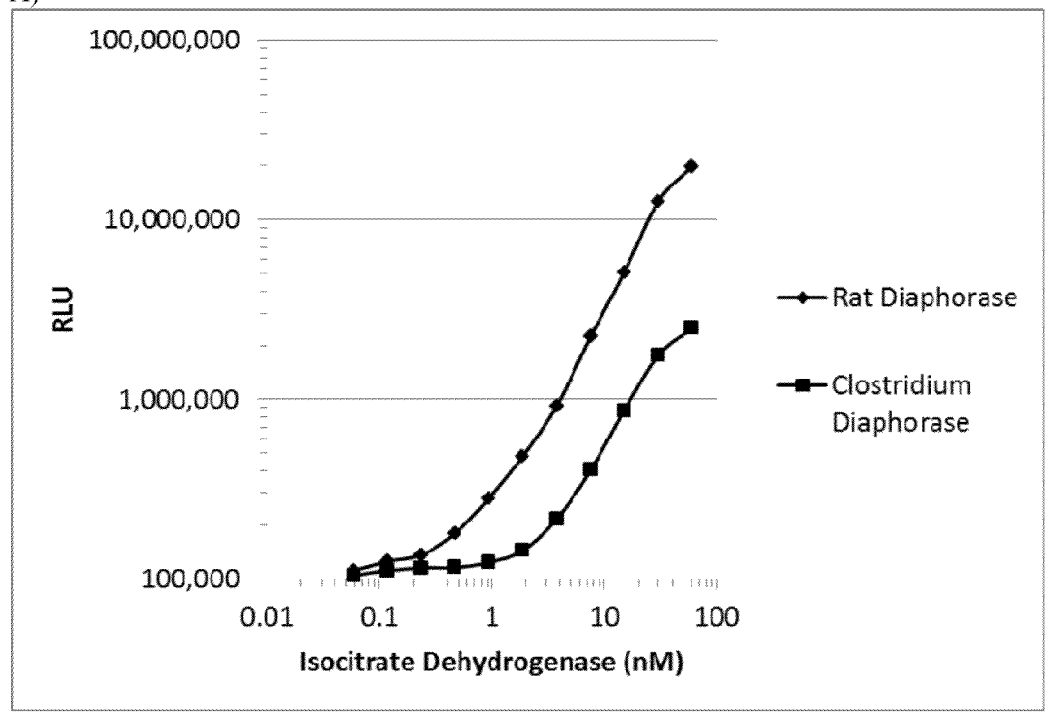
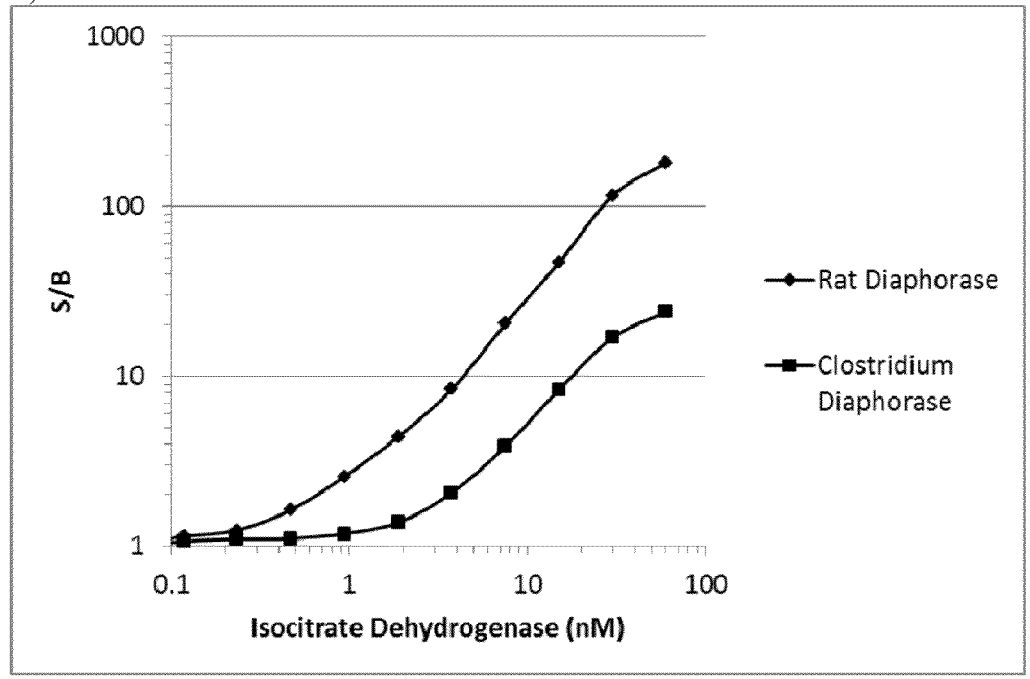

US 9,273,343 B2

COMPOUNDS AND METHODS FOR ASSAYING REDOX STATE OF METABOLICALLY ACTIVE CELLS AND METHODS FOR MEASURING NAD(P)/NAD(P)H

CROSS-REFERENCE TO RELATED APPLICATIONS

The present application claims the benefit of U.S. Provisional Application No. 61/530,559, filed Sep. 2, 2011, which is incorporated by reference herein.

FIELD OF THE INVENTION

The present invention provides compounds and methods for assaying the redox state of metabolically active cells and methods for assaying enzyme activity and/or metabolite level by coupling to redox defining co-factor NAD(P)/NAD(P)H measurement.

BACKGROUND OF THE INVENTION

Cell Viability

Cellular energy metabolism is a complex process that allows cells to generate energy through a series of enzymatic and chemical reactions. In eukaryotes, metabolism is centered at the mitochondria and involves multiple pathways including glycolysis and oxidative phosphorylation. Depending on cell status and adaptation to various stimuli, a particular metabolic pathway is activated, and the study of the enzymatic reactions and metabolites of these pathways help researchers to understand the metabolic status of the cell as well as cell viability and toxicity. One essential aspect of cellular energy metabolism is the reduction-oxidation (redox) state of the cell. During cellular energy metabolism, energy is often stored and released as part of redox reactions. Major co-factors in these metabolic reactions are the nucleotides NAD(P) and NAD(P)H. The redox state of a cell is described as the balance between the oxidized form of these nucleotides (NAD(P)) and the reduced form (NAD(P)H). The redox state is studied in order to determine the metabolic status of live cells and can be used to study enzymes and metabolites that are involved in the redox state and/or utilized directly or indirectly the NAD(P)/NAD(P)H nucleotides. Methods currently exist to study the redox state of cells, including tetrazolium salts (MTT, MTS, and XTT) and resazurin. All of these methods involve compounds that are reduced in metabolically active cells to produce either a colorimetric or fluorescent signal. These methods are limited by low sensitivity and often require labor-intensive nucleotide extraction methods and/or enzymatic cycling reactions to amplify the signal. These molecules vary structurally, and it is not known what cellular enzymes reduce each compound; consequently, the design of new molecules to study the redox state is not obvious.

The molecules NAD and NADP, and their reduced forms NADH and NADPH, are cofactors present in all organisms. They are involved in many and multiple oxidoreductase reactions critical to cell metabolism as well as function in other necessary cellular processes. Often, it is desirable to measure the levels of NAD, NADP, NADH, NADPH as an indication of cellular redox state and its perturbation by treatments.

SUMMARY

In one aspect, the present invention provides a compound according to any one of Formula (I) to (IV) described herein.

In another aspect, the present invention provides methods for analyzing the redox state of a metabolically active cellular sample using the compounds of Formulas (I) to (V) described herein.

In a further aspect, the present invention provides methods for detecting NADH or NADPH in a sample using the compounds of Formulas (I) to (V) described herein.

In yet another aspect, the present invention provides methods for detecting NAD or NADP in a sample using the compounds of Formulas (I) to (V) described herein.

Additionally, in one aspect, the present invention provides a method for detecting the presence of an enzyme that utilizes or produces NAD, NADP, NADH or NADPH in a sample using the compounds of Formulas (I) to (V) described herein.

In an additional aspect, the present invention provides a method for detecting the presence of an enzyme that does not utilize or produce NAD, NADP, NADH or NADPH in a sample using the compounds of Formulas (I) to (V) described herein.

In another aspect, the present invention provides a method for detecting cellular metabolites in a sample using the compounds of Formulas (I) to (V) described herein.

In a further aspect, the present invention provides a method of screening for a compound that affects cell toxicity, cell viability or the redox state of a cell using the compounds of Formulas (I) to (V) described herein.

In yet another aspect, the present invention provides a method of determining NAD(P):NAD(P)H ratio in a sample using the compounds of Formulas (I) to (V) described herein.

In an additional aspect, the present invention provides a method of determining total NAD(P)/NAD(P)H in a sample using the compounds of Formulas (I) to (V) described herein.

In another aspect, the present invention provides a kit containing the compounds of Formulas (I) to (IV) described herein.

FIG. 6 shows fluorescent imaging of live cells. HeLa cells were treated with PBI-4412, 4413, 4440 or 4441 and imaged.

Figure 7A:
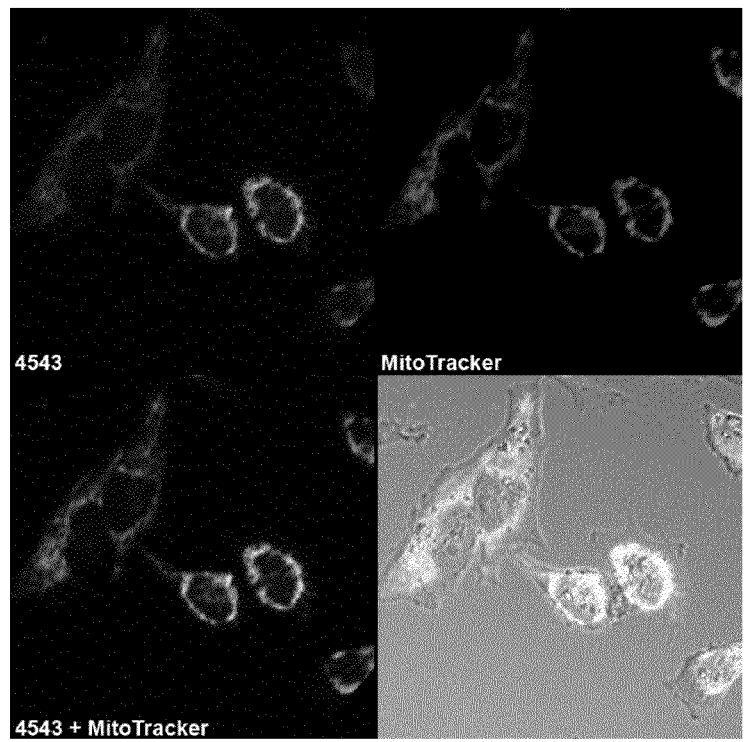
Figure 7B:
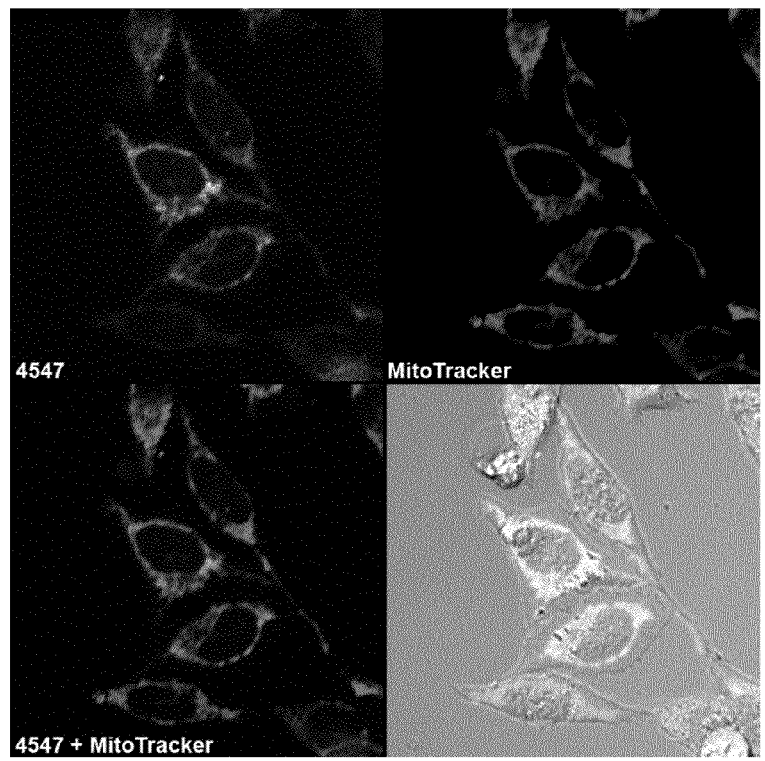

FIG. 7 shows mitochondrial targeting. HeLa cells were treated with PBI-4543 or 4547. The media was replaced with low serum media containing MitoTracker DeepRed FM and imaged.

FIG. 8 shows a cellular function assay. HeLa cells were treated with PBI-4543 or 4547 and incubated with the ETC inhibitor, 3-nitropropionic acid (3-NPA).

Figure 9:
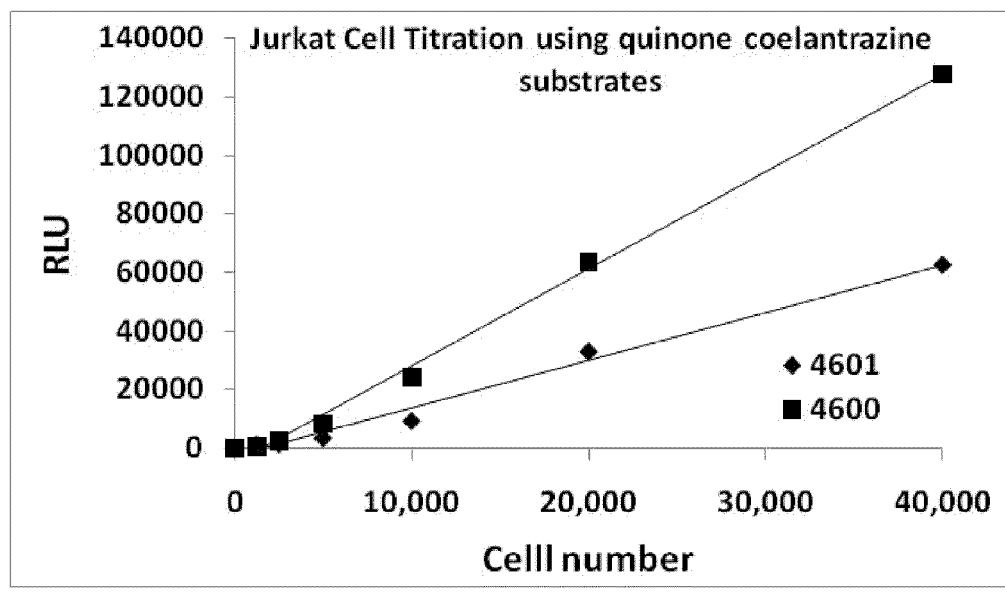

FIG. 9 shows a linear correlation between cell number and luminescence indicating a direct relationship between luminescence measured with compounds 4600 and 4601 and cell number.

Figure 10:
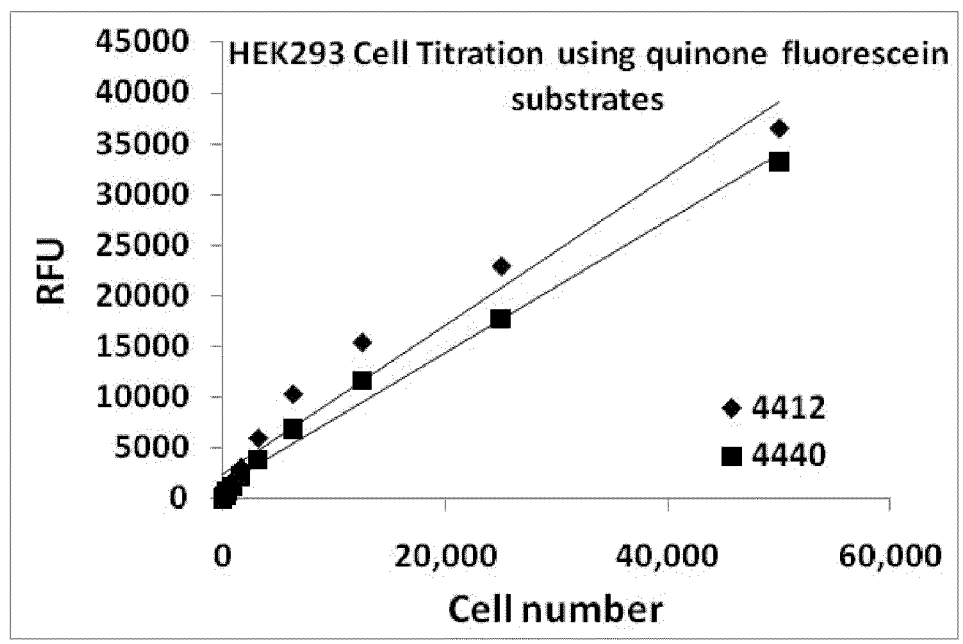

FIG. 10 shows the linear correlation between cell number and fluorescence indicating a direct relationship between fluorescence measured with compounds 4440 and 4412 and cell number.

Figure 11:
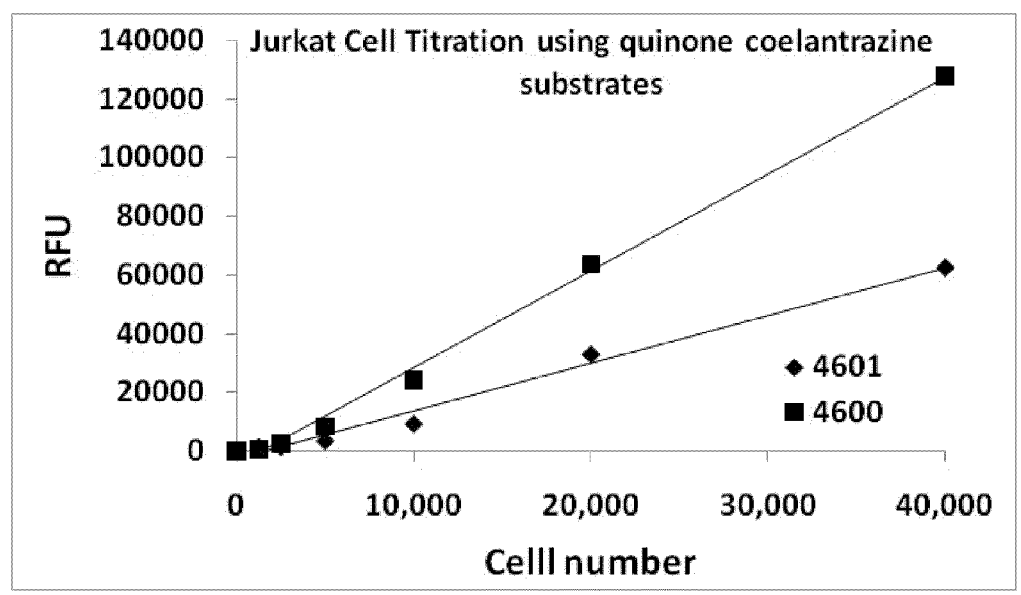

FIG. 11 shows a decrease in the fluorescence signal upon the treatment of cells with digitonin. To induce cytotoxicity, cells were treated with digitonin. The amount of viable cells after digitonin treatment was measured by incubating cells with compound 4440, and the fluorescent signal compared to the fluorescent signal measured in untreated (no digitonin) cells. More than a 90% decrease in fluorescent signal was seen after digitonin treatment illustrating the ability of 4440 compound to measure the decrease in cell viability.

Figure 12:
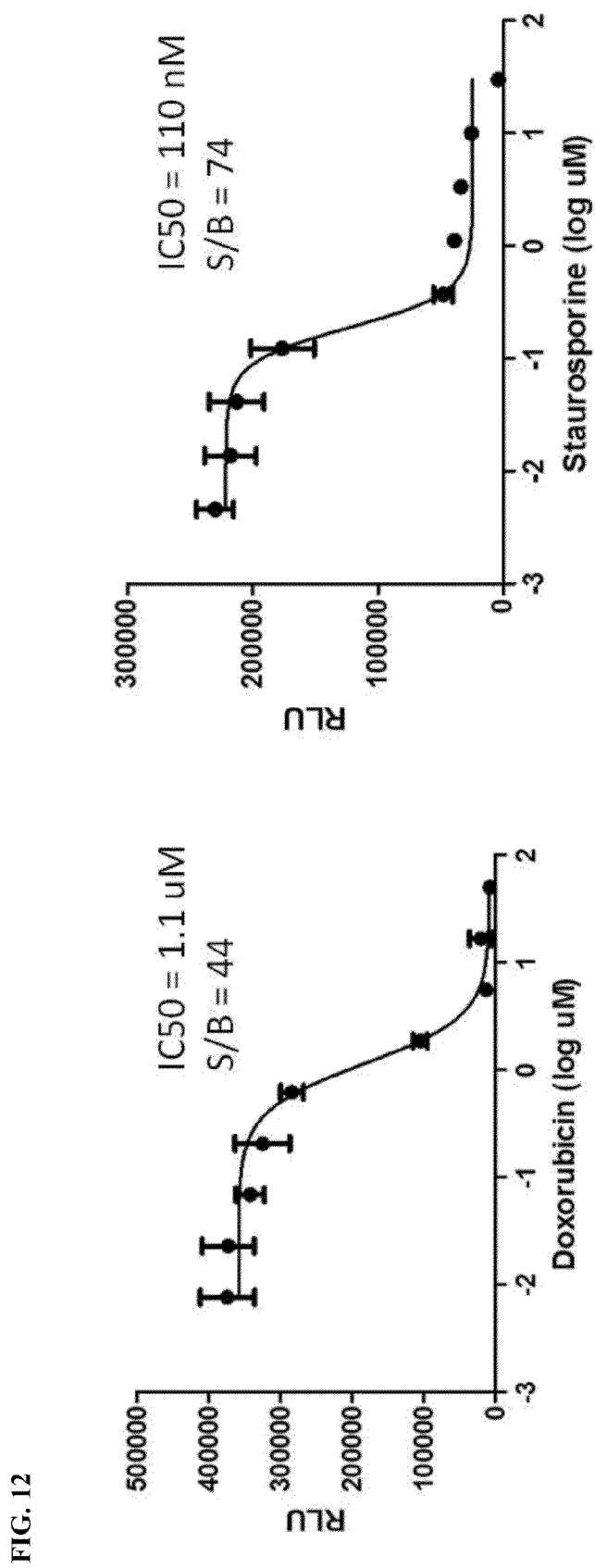

FIG. 12 shows pharmacological characterization of a compound affecting cell viability using the method described herein.

Figure 13A:
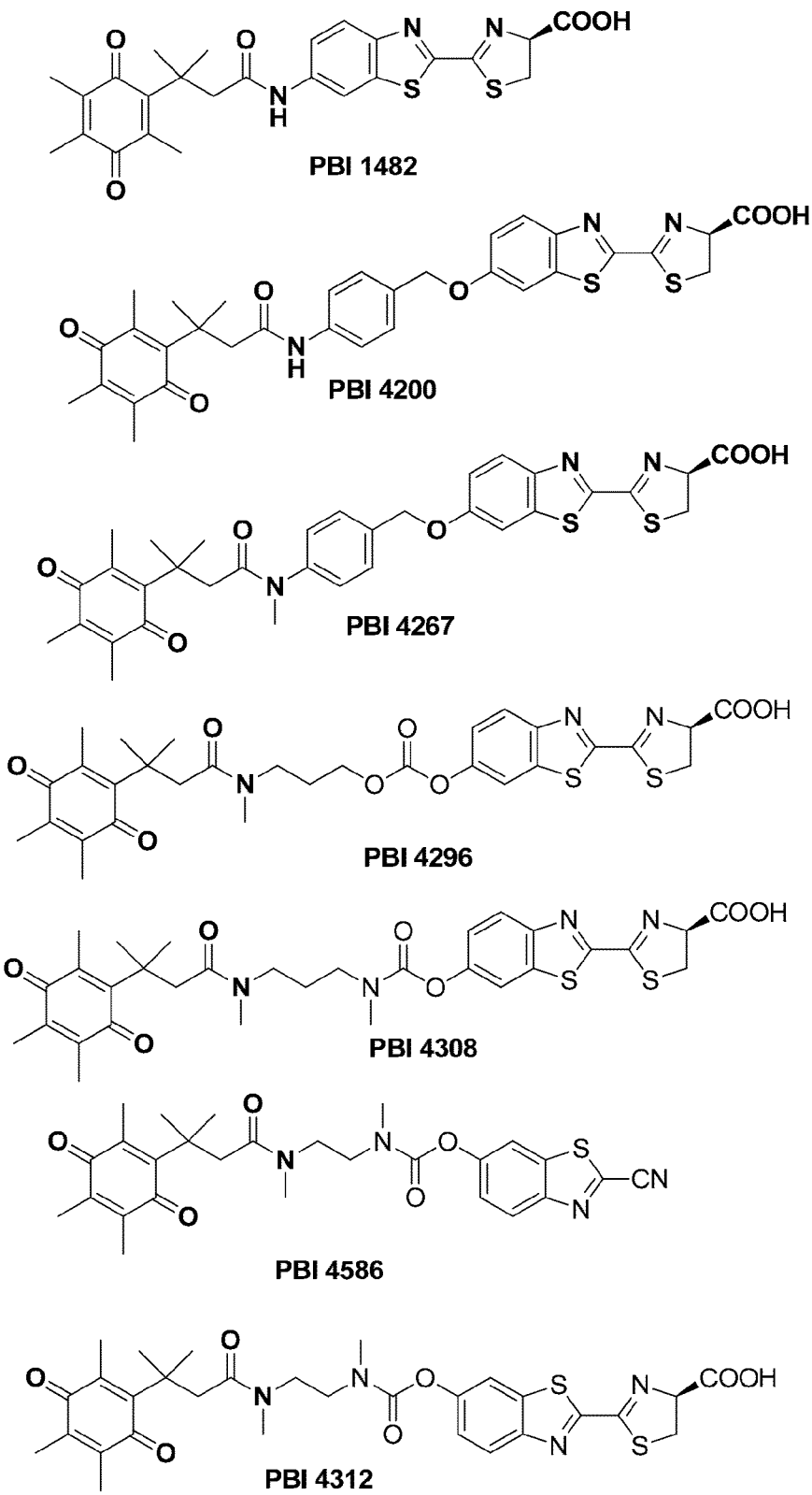
Figure 13A:
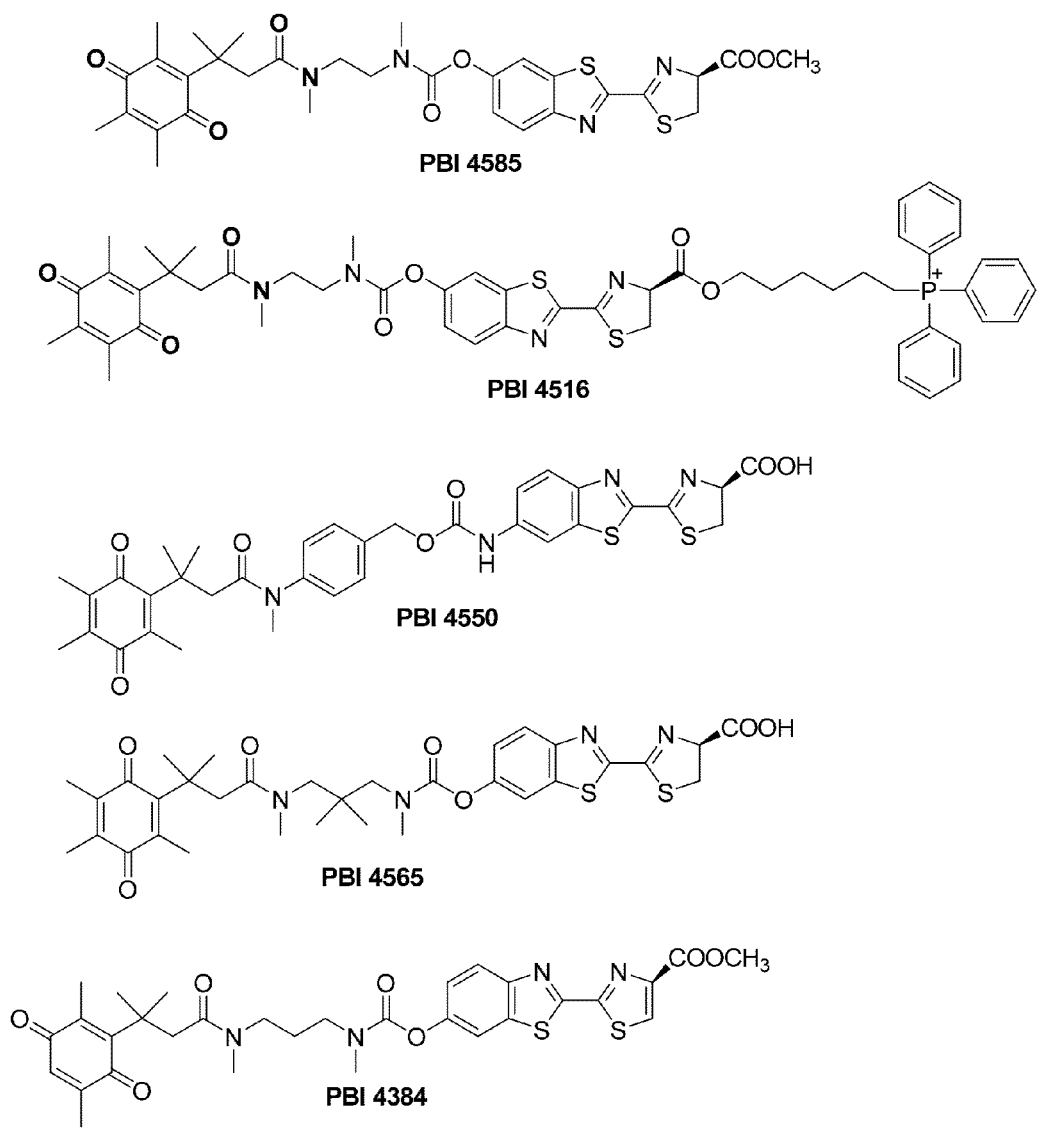

FIG. 13A shows suitable compounds according to Formula (I)-(IV).

Figure 13B:
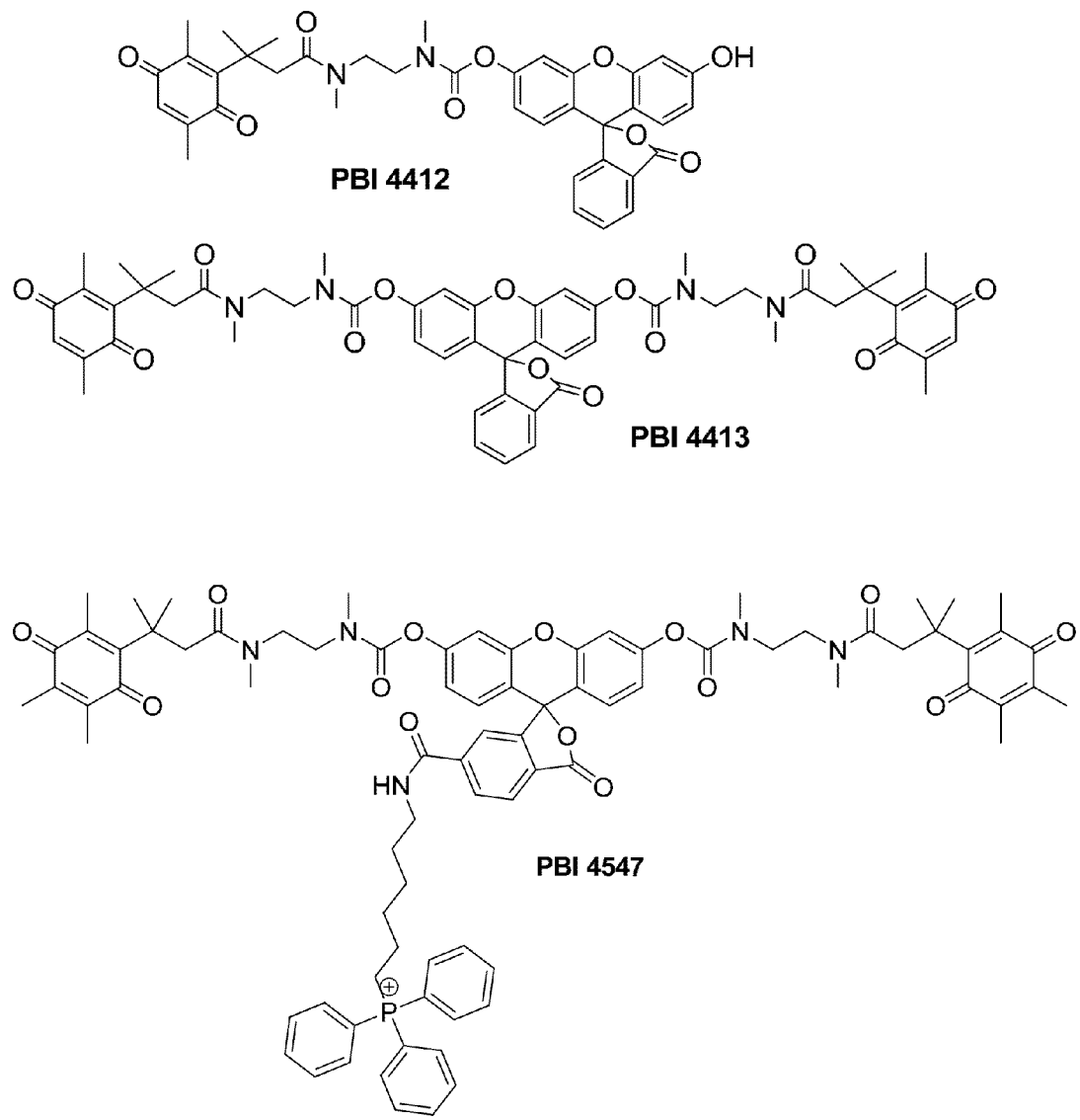

FIG. 13B shows suitable compounds according to Formula (V).

Figure 14:
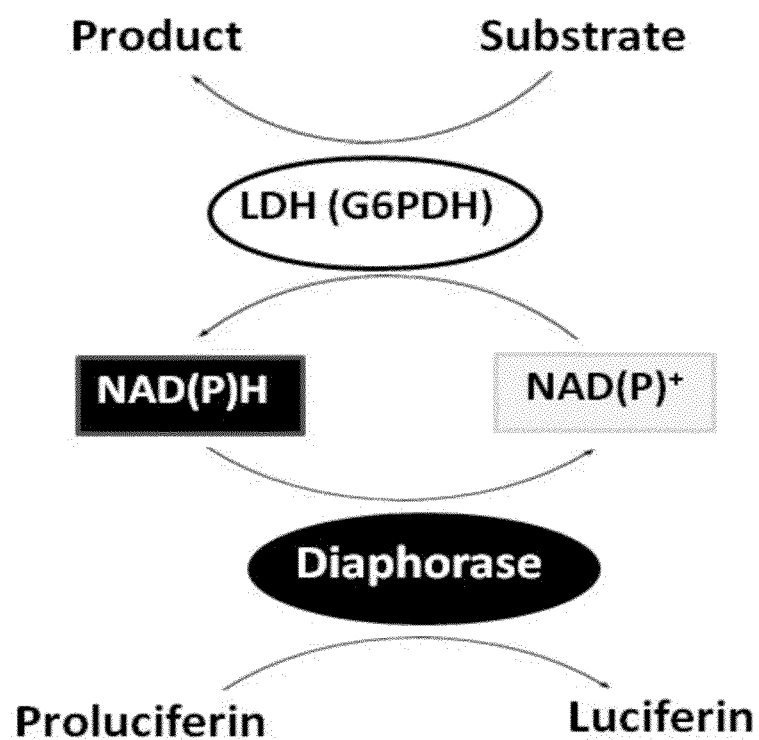

FIG. 14 shows the general scheme of the method of the present invention.

FIG. 15 shows lactate determination in Jurkat cells. a) Lysed Jurkat cells were serially diluted into a 96-well luminometer plate. A 2× reaction mix containing NAD, diaphorase, PBI-4312, lactate dehydrogenase was added, and luminescence (RLUs) detected; b) The linear correlation between cell number and luminescence output indicating a direct relationship between luminescence measured with PBI-4312 and lactate concentration.

FIG. 16 shows ethanol determination in vitro: a) Serial dilutions of 2× ethanol in 1× PBS were performed in a 96-well luminometer plate. A 2× reaction mix containing NAD, diaphorase, PBI-4312, and alcohol dehydrogenase was added, and luminescence detected (RLUs); b) Linear correlation between % ethanol and luminescence output indicating a direct relationship between luminescence generated via pro-luciferin conversion and ethanol concentration.

Figure 17:
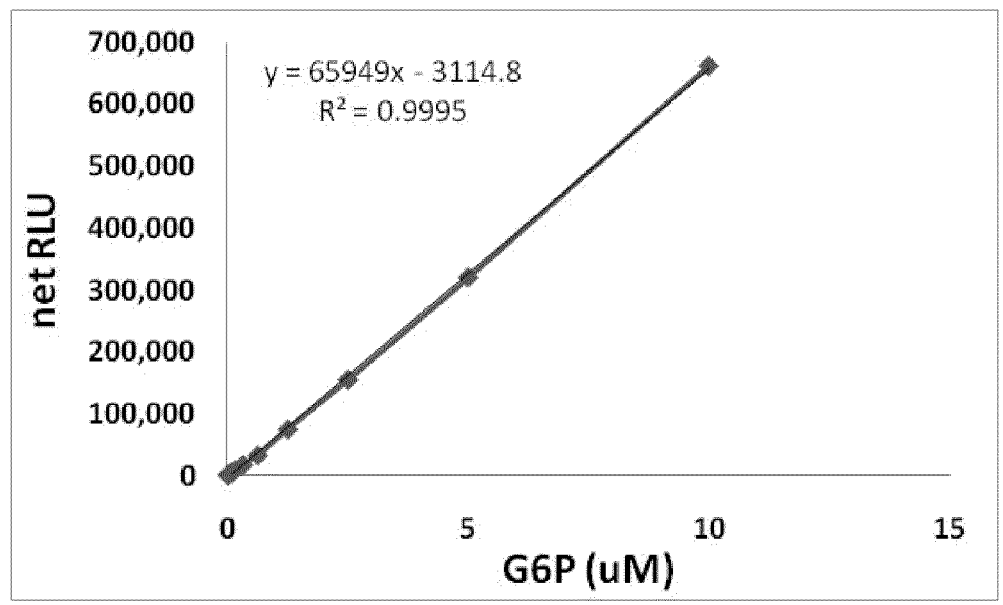

FIG. 17 shows glucose-6-phosphate determination in vitro. Serial dilutions of 2× glucose-6-phosphate (G6P) in 1×PBS were performed in a 96-well luminometer plate. A 2× reaction mix containing NADP, diaphorase, PBI-4312, and G6P-dehydrogenase was added, and luminescence detected. The graph shows linear correlation between luminescence and concentration of G6P.

Figure 18:
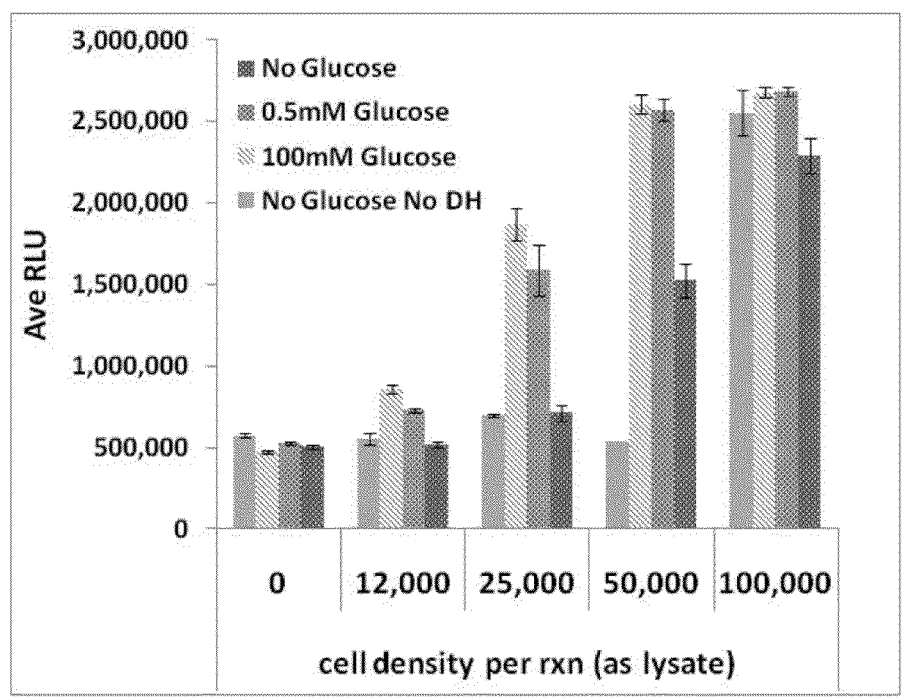

FIG. 18 shows glucokinase determination in HepG2 cells. Serial dilutions of HepG2 cells were made in a 96-well luminometer plate. A 2× reaction mix containing NADP, diaphorase, PBI-4312, and G6P-DH dehydrogenase was added, and luminescence detected. The difference between the luminescence with 100 mM glucose and 0.5 mM glucose is the glucokinase activity.

FIG. 19 shows NADH detection with rat or *Clostridium* diaphorase. A) Average RLUs and B) Signal-to-Noise ratio.

Figure 20:
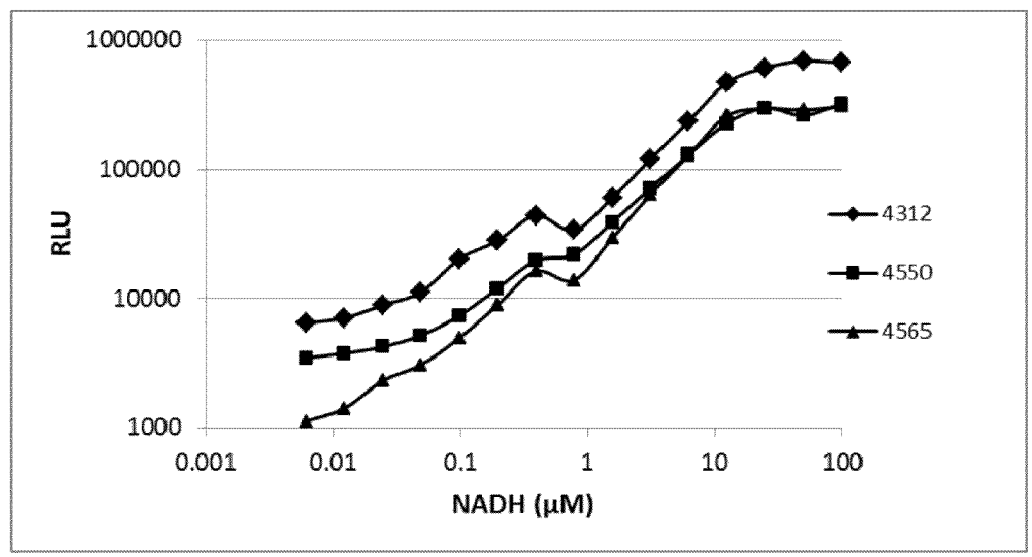

FIG. 20 shows NADH titration.

Figure 21:
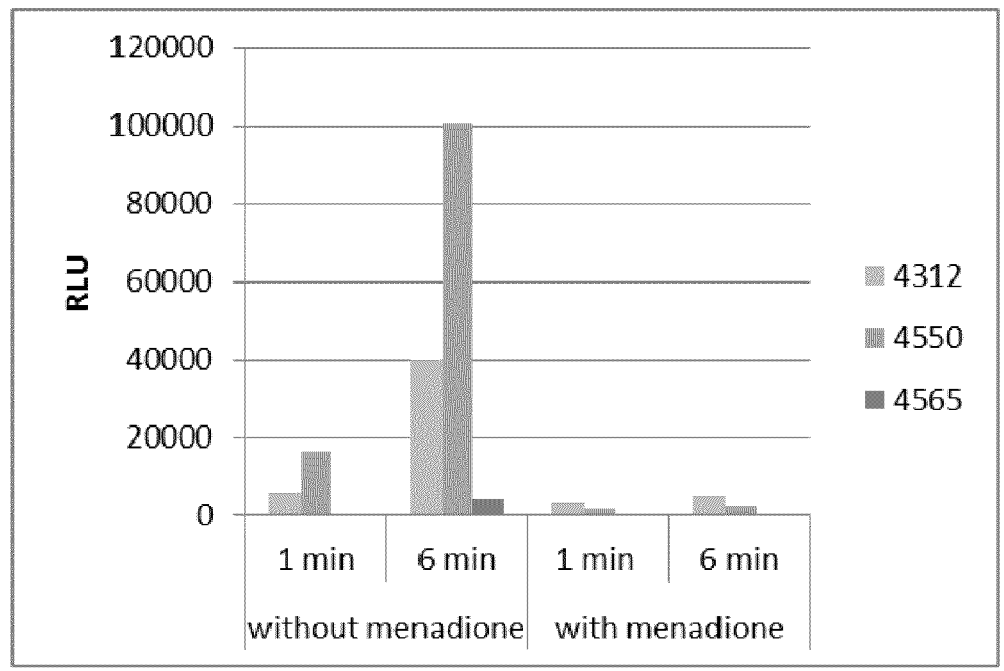

FIG. 21 shows inhibition of diaphorase reaction by menadione. PBI-4312, 4550 or 4565 was incubated with NADH and rat diaphorase with half the samples treated with menadione. Luminescence (RLUs) was detected, and sample replicates averaged.

Figure 22A:
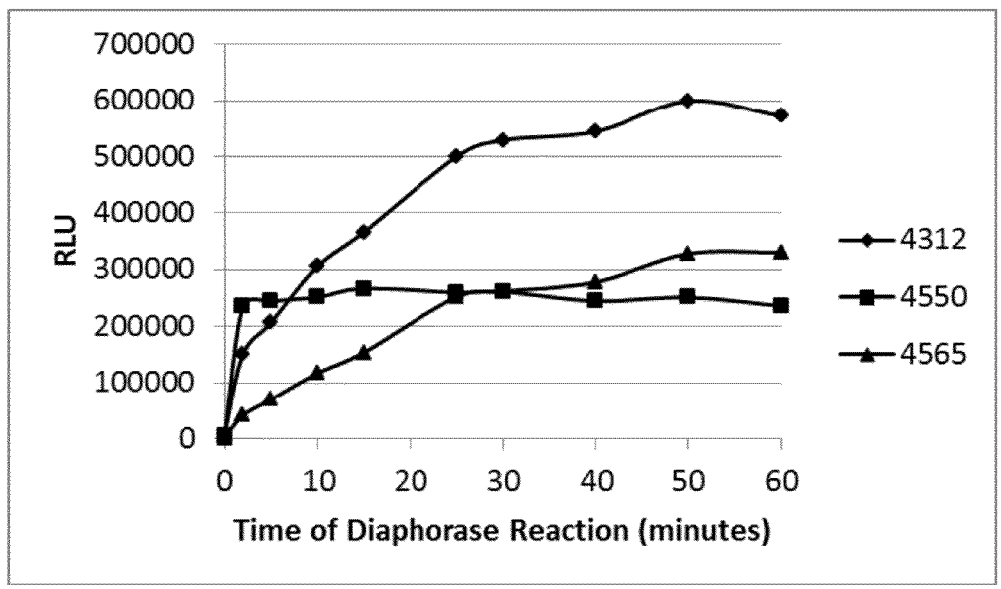

FIG. 22 shows a time course of diaphorase reaction. PBI-4312, 4550 and 4565 were incubated with NADH and rat diaphorase. Luciferase detection reagent (LDR) containing menadione was added at various timepoints, and luminescence (RLUs) detected (a). The fraction of maximum signal was also determined (b).

Figure 23:
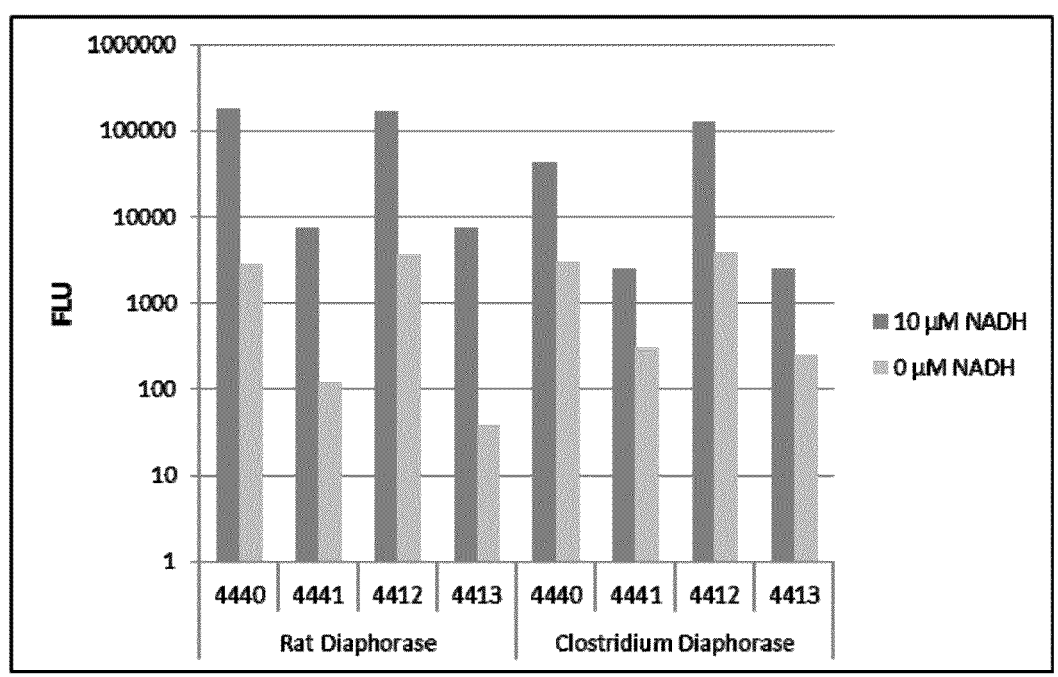

FIG. 23 shows fluorescent NADH detection. PBI-4412, 4413, 4440 and 4441 were incubated with NADH and either rat or *Clostridium* diaphorase. At 60 minutes, fluorescent signal (FLUs) increases with each compound with each diaphorase.

FIG. 24 shows reaction time course with PBI-4412, 4440, 4441, and 4413 and either rat or *Clostridium* diaphorase.

Figure 25:
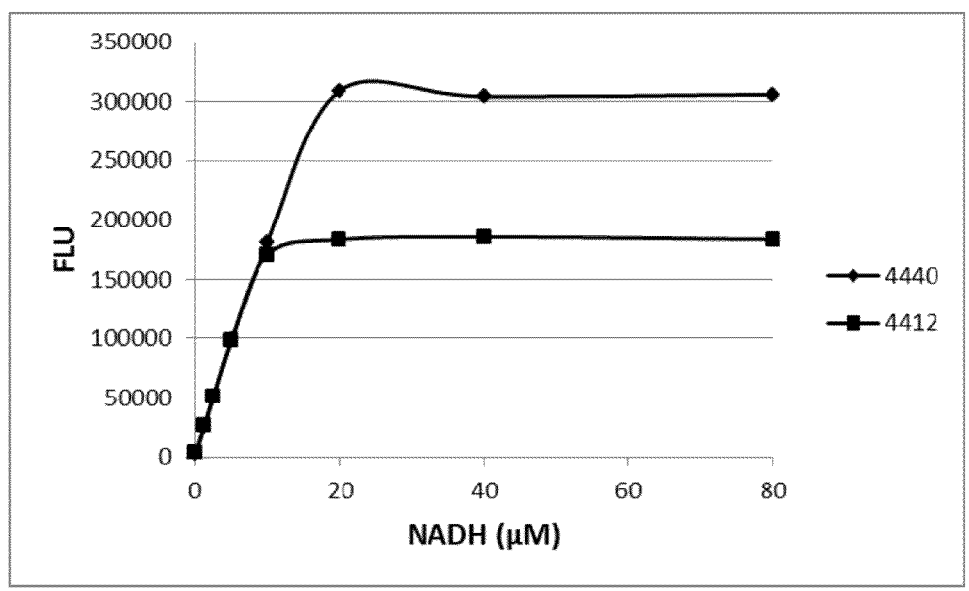

FIG. 25 shows an NADH titration at 60 minutes with PBI-4440 or 4412 and rat diaphorase.

FIG. 26 shows the detection of isocitrate dehydrogenase by measuring NADH. A) Average RLUs and B) Signal-to-Background ratio.

Figure 27:
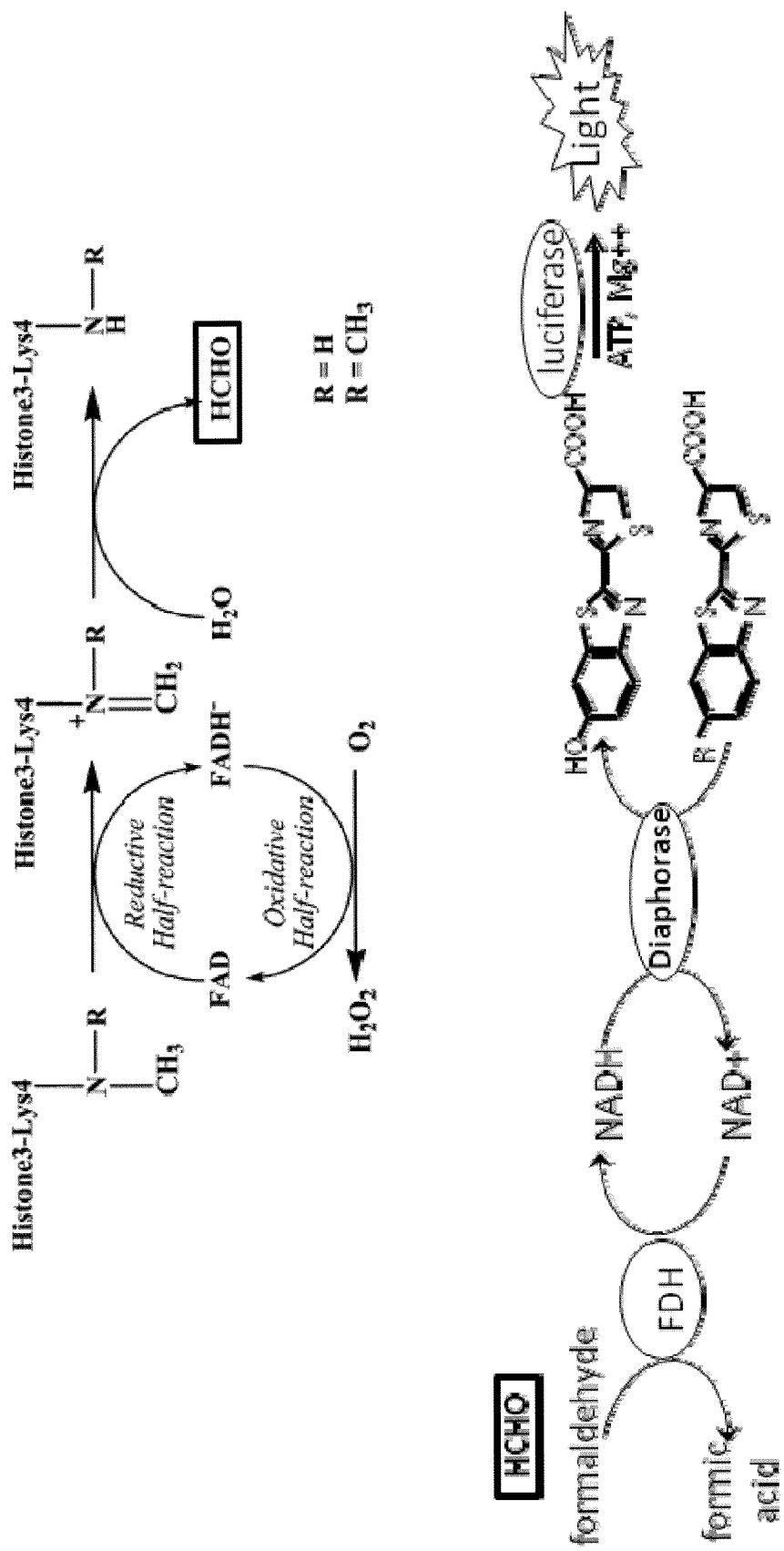

FIG. 27 shows the general scheme of demethylase detection by measuring NADH.

Figure 28:
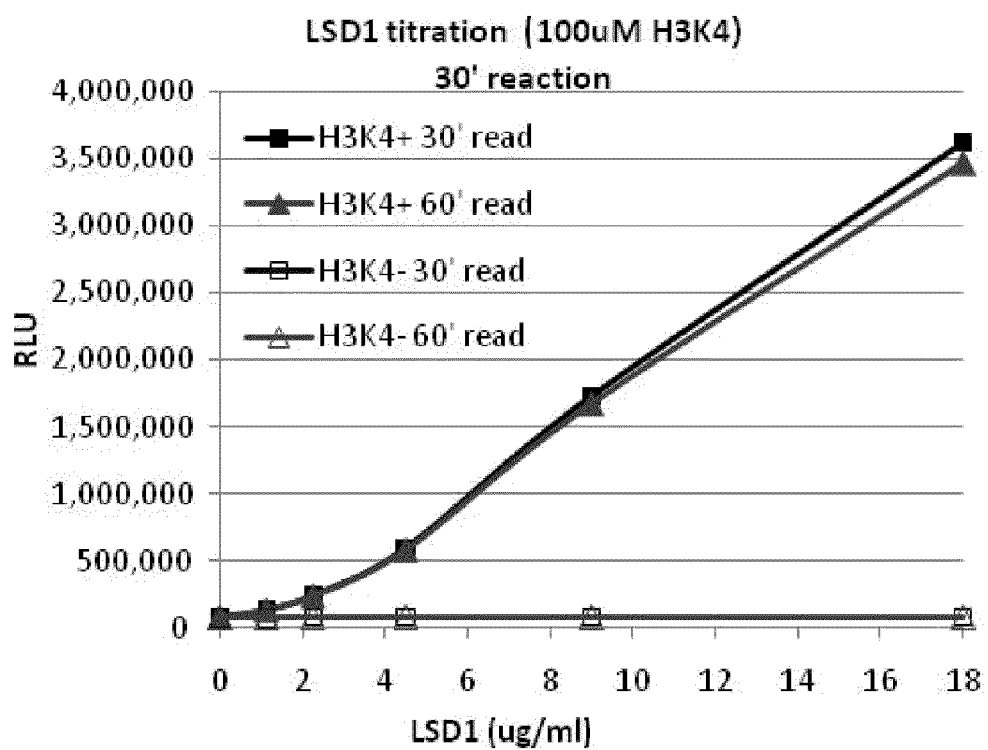

FIG. 28 shows the average RLUs at 30 and 60 minutes at various concentrations of LSD1 with or without H3K4.

Figure 29:
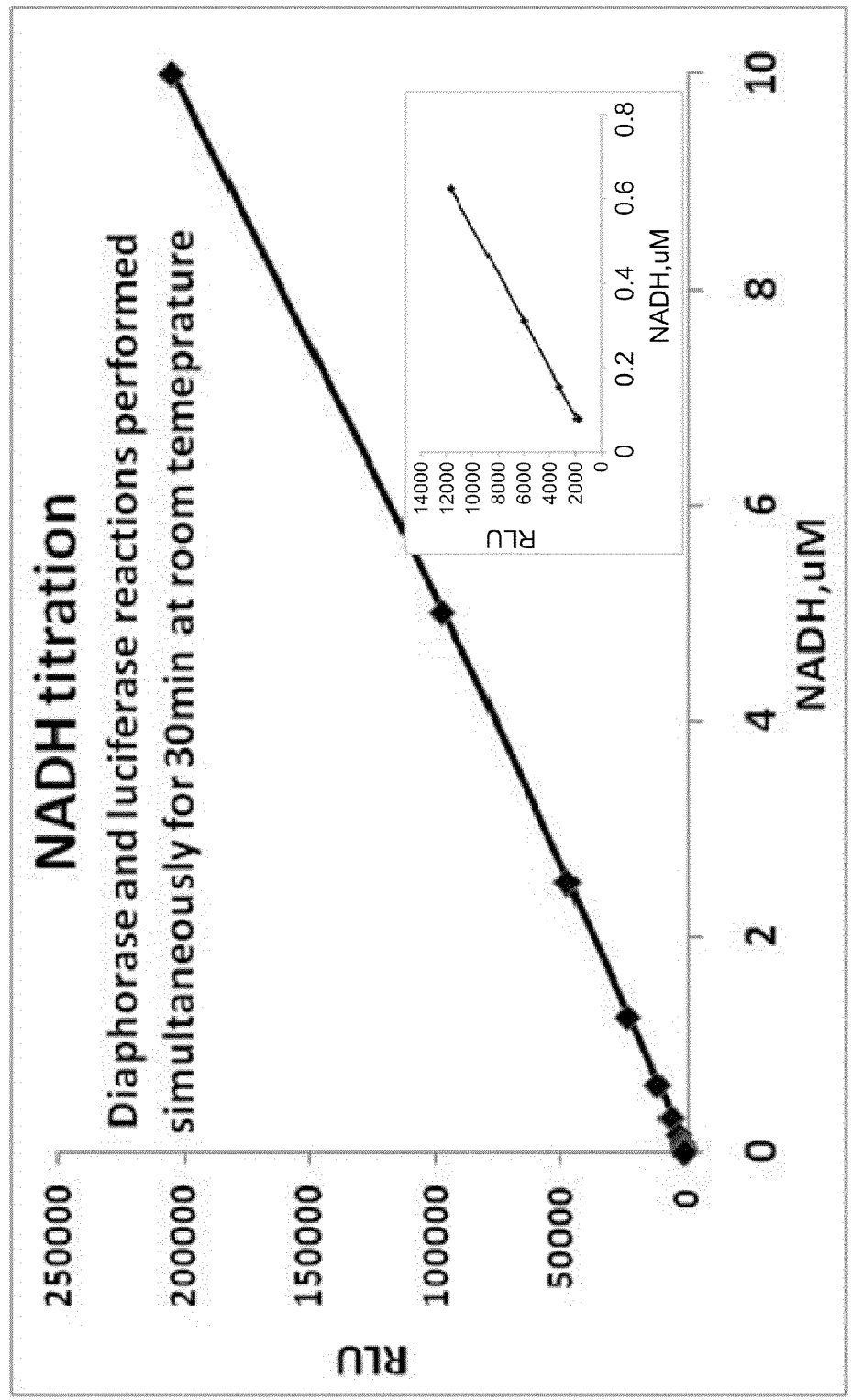

FIG. 29 shows the results of NADH titration under conditions where both luciferase and diaphorase reactions are performed simultaneously.

Figure 30A:
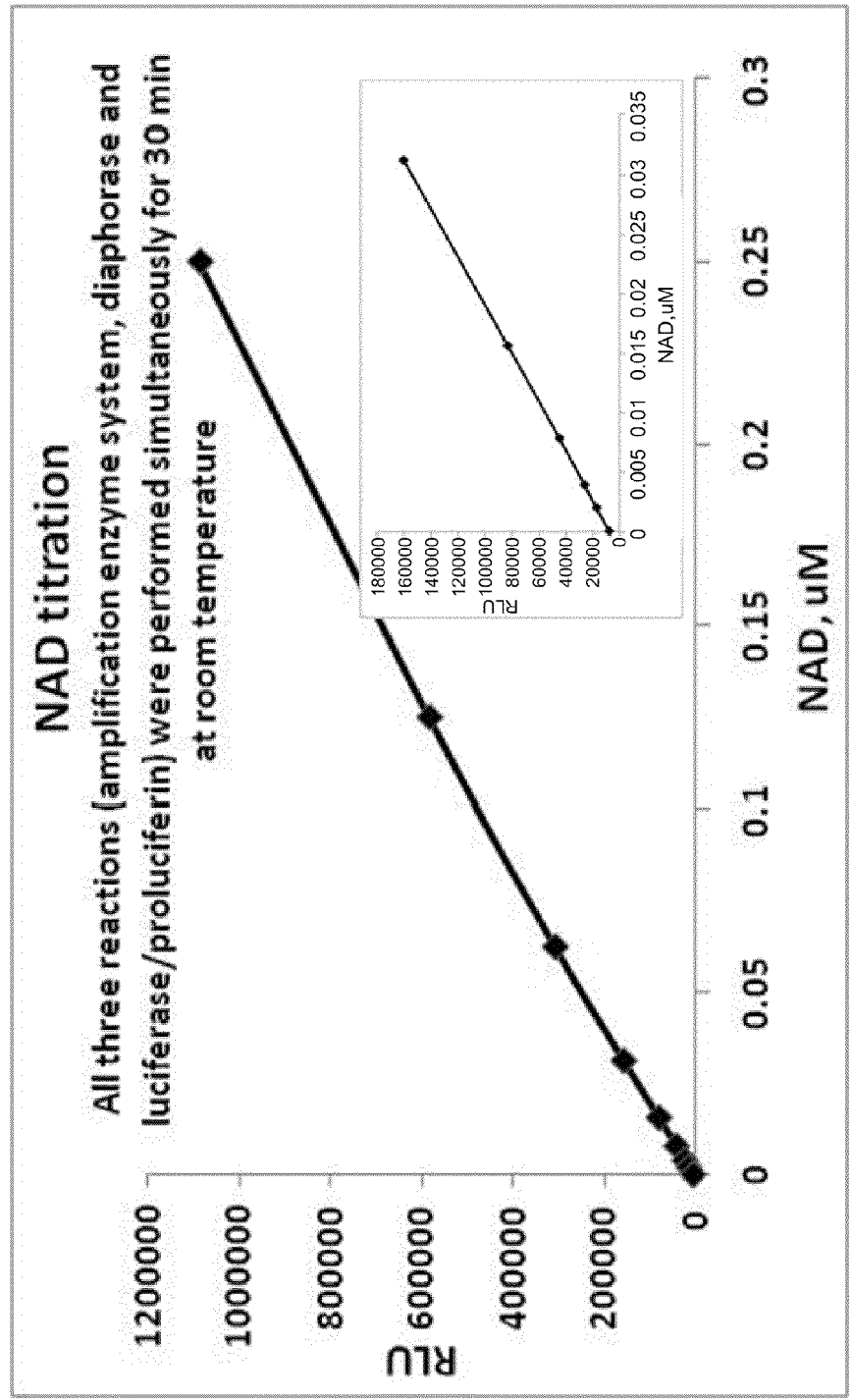

FIG. 30A shows NAD titration.

Figure 30B:
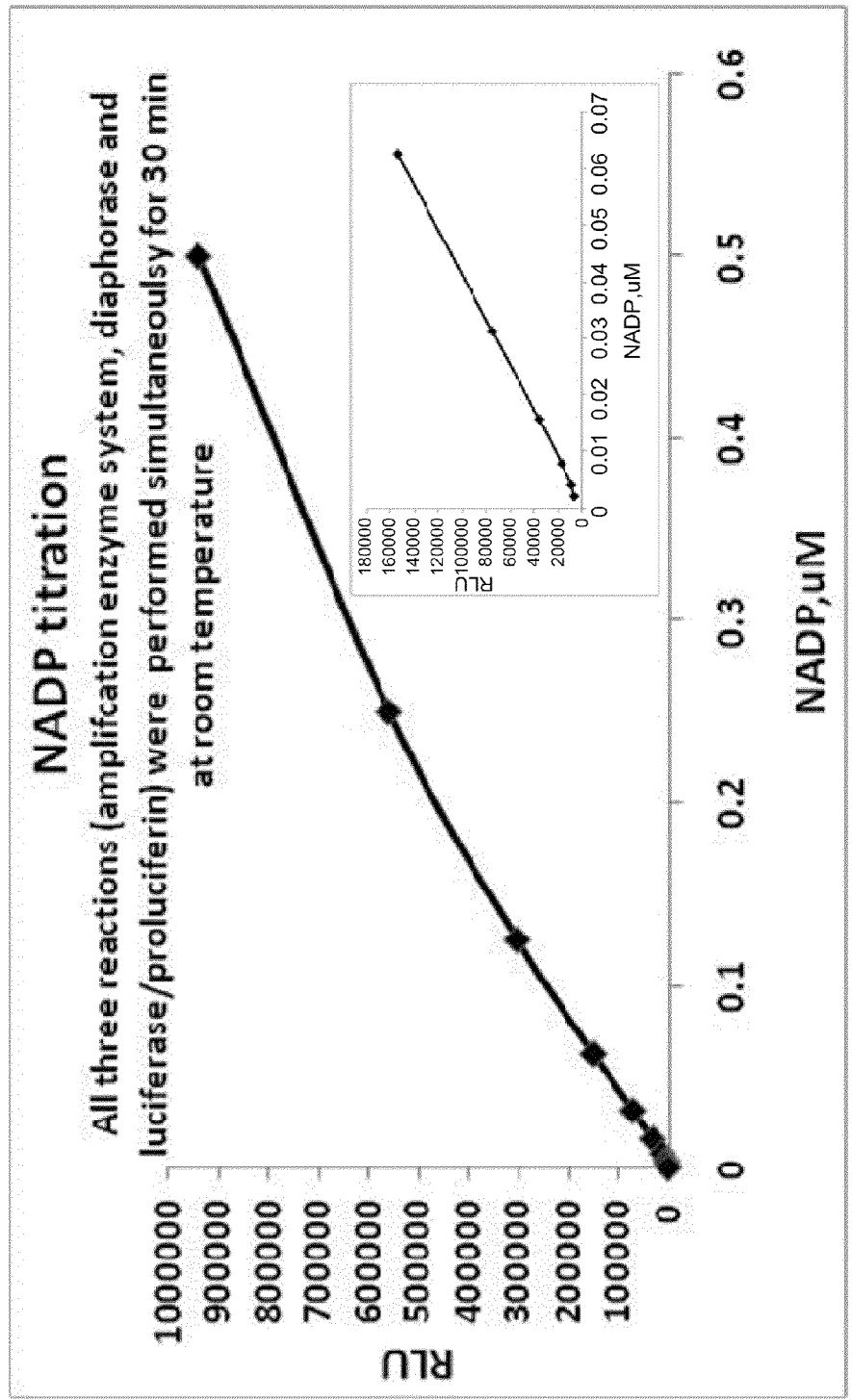

FIG. 30B shows NADP titration.

Figure 31:
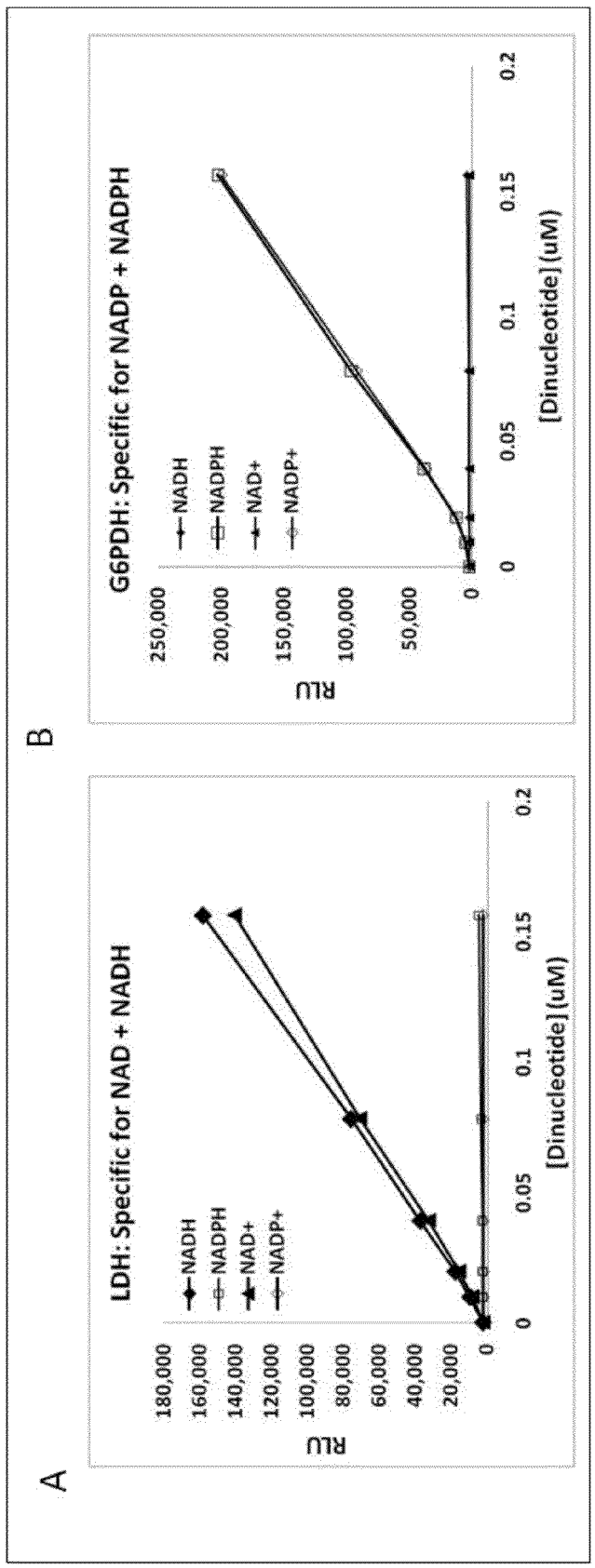

FIG. 31 shows specificity in dinucleotide detection when NAD and/or NADP specific amplification enzyme systems are coupled with the detection method described herein.

Figure 32:
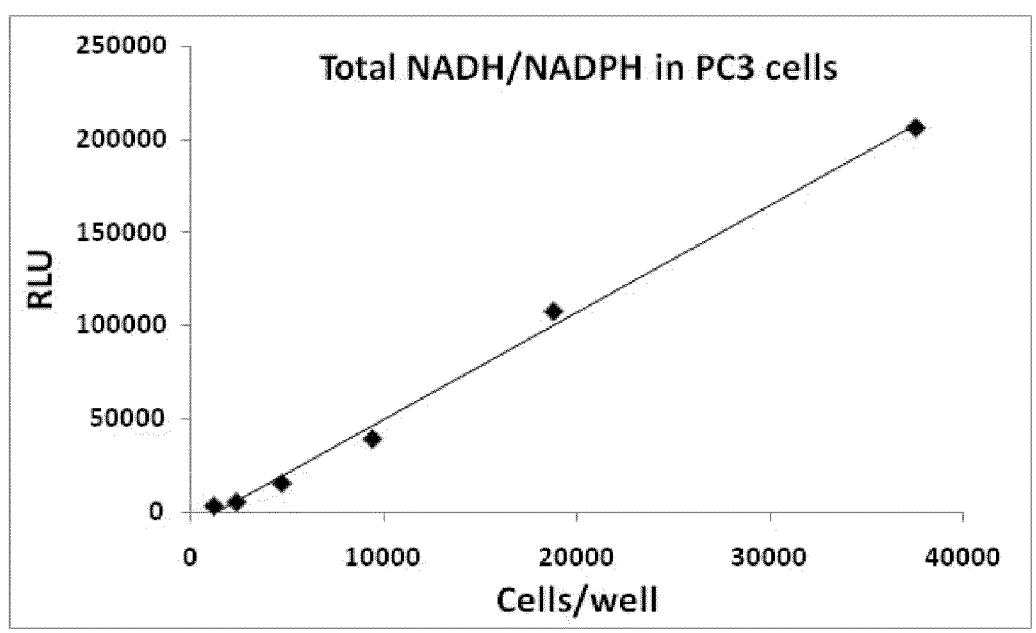

FIG. 32 shows the measurement of total amount of reduced dinucleotides NADH/NADPH present in the cells.

Figure 33:
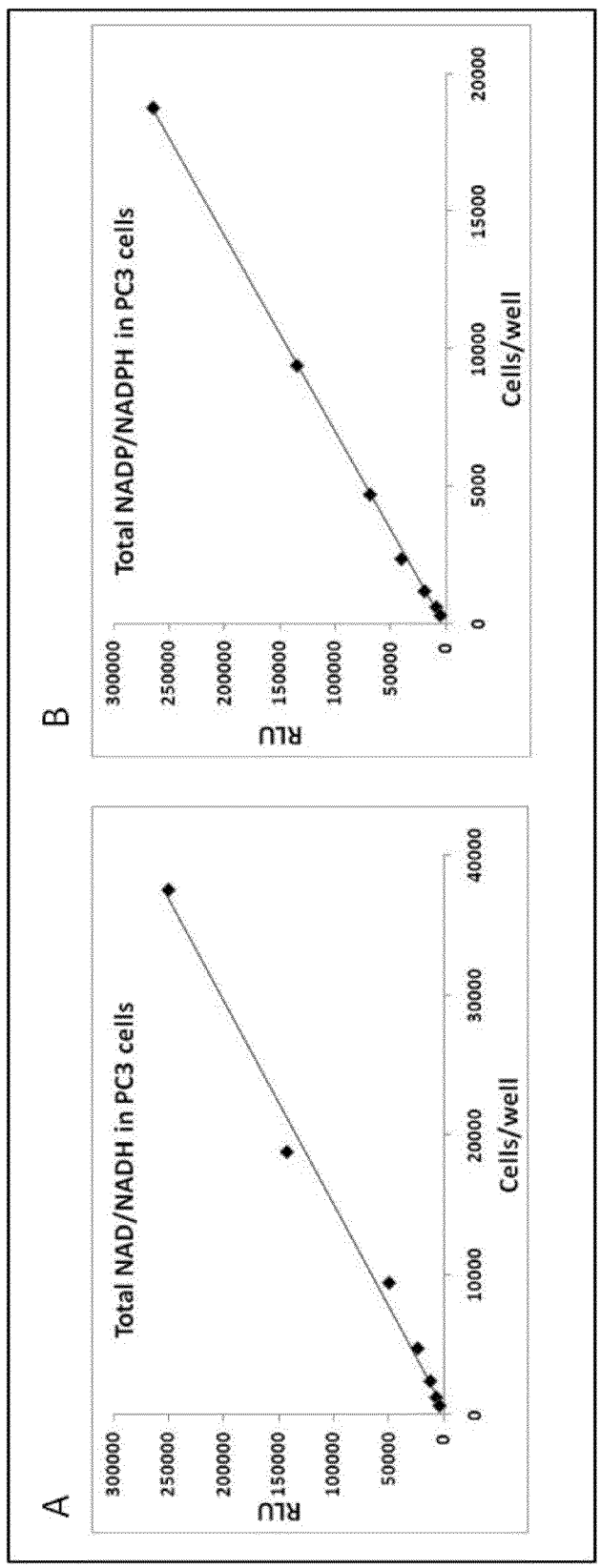

FIG. 33 shows the measurement of total dinucleotides, a) NAD/NADH and b) NADP/NADPH, present in the cells.

Figure 34:
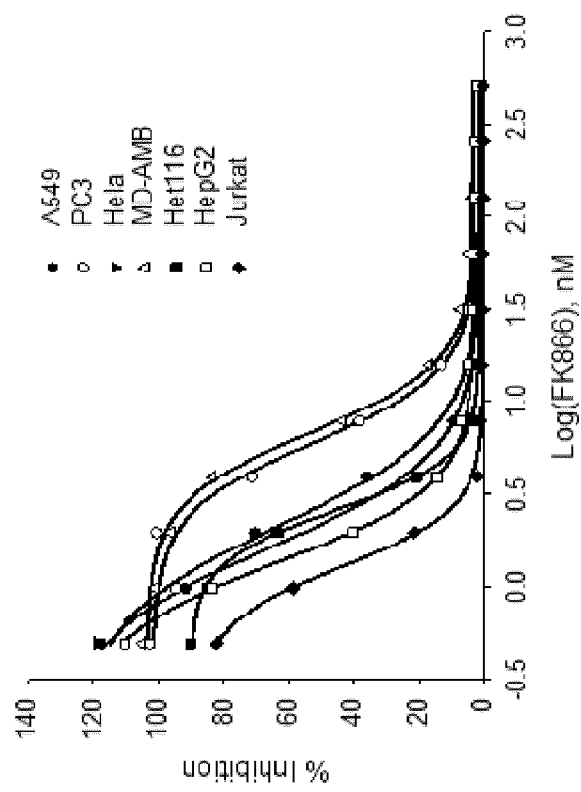

FIG. 34 shows the detection of NAD biosynthesis inhibition using the method described herein.

Figure 35:
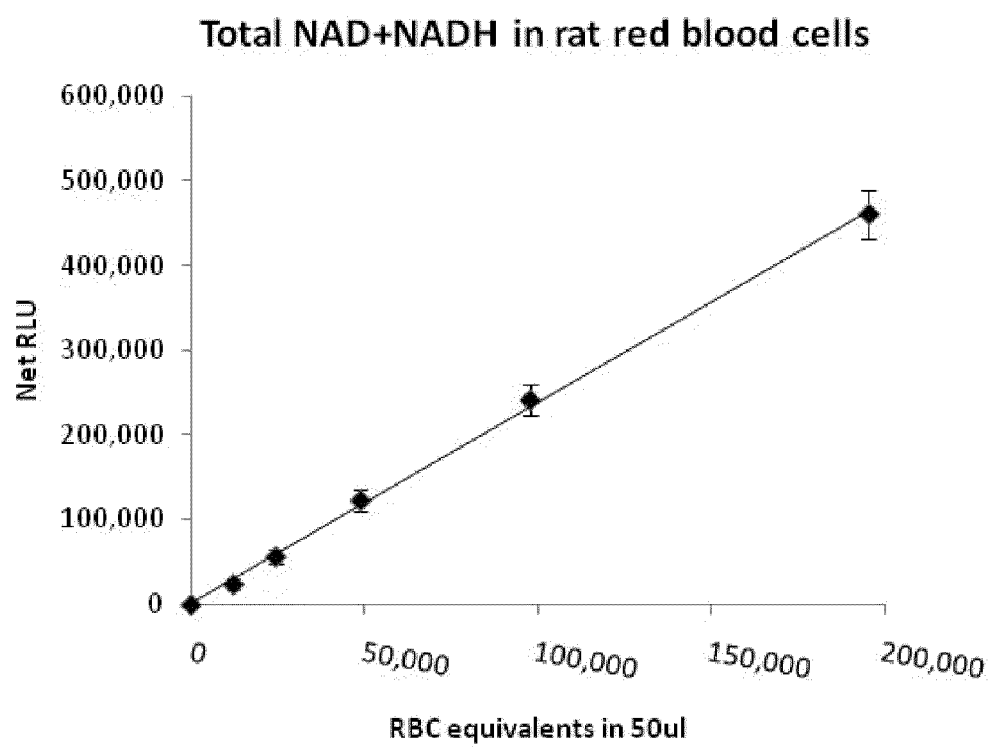

FIG. 35 shows the ability to measure total NAD/NADH in red blood cells (RBCs).

Figure 36:
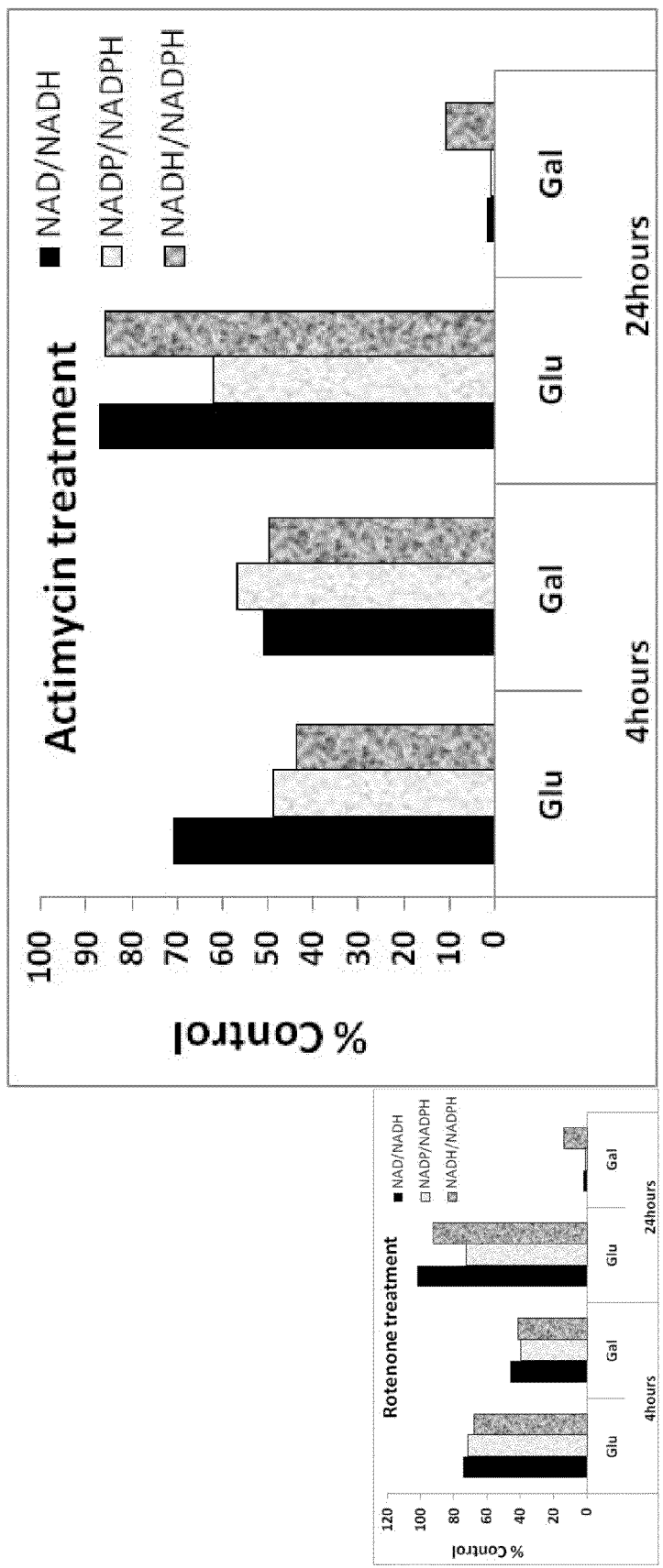

FIG. 36 shows the effect of the mitochondria toxins, rotenone and actinmycin, on total NAD(P)/NAD(P)H levels.

Figure 37:
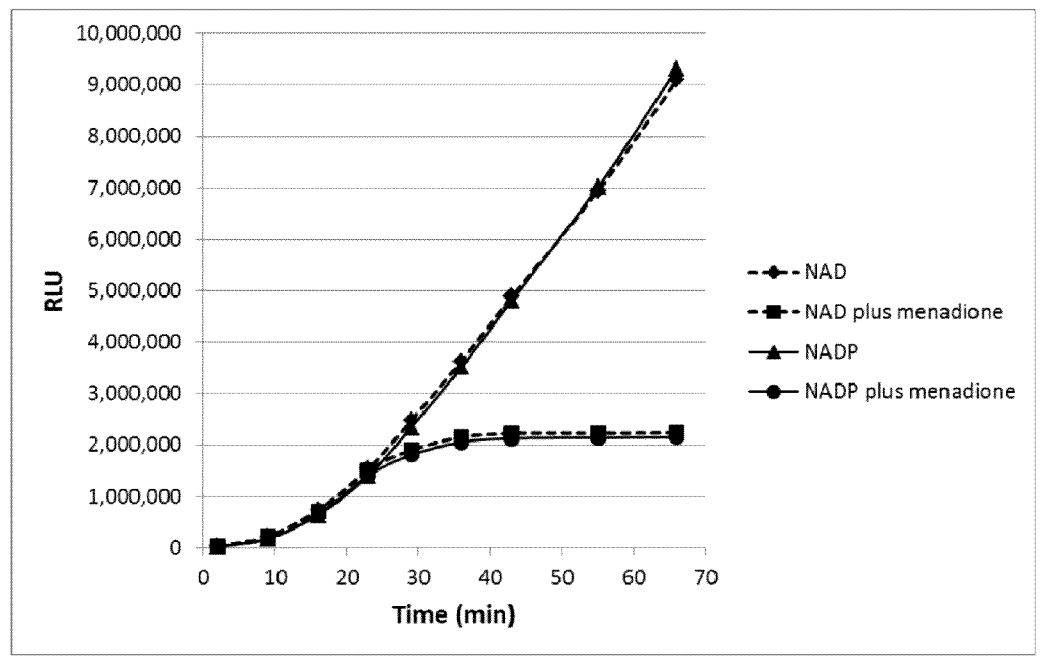

FIG. 37 shows the ability to monitor signals with time or the use of menadione to stop light signal increase, thereby allowing the light signals to be read at a later time.

Figure 38:
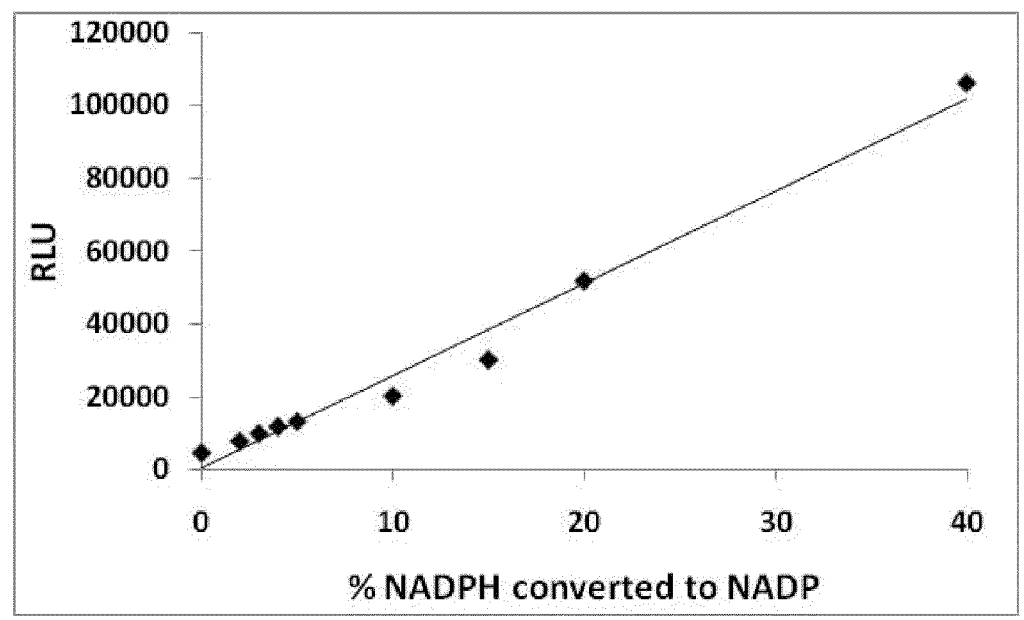

FIG. 38 shows the sensitivity of the assay to detect different concentrations of NADP in the presence of NADPH.

DETAILED DESCRIPTION OF THE INVENTION

The present invention provides compounds and methods for assaying redox state of metabolically active cells and methods for assaying enzyme activity and/or metabolite level by coupling to redox defining co-factor NAD(P)/NAD(P)H measurement.

DEFINITIONS

As used herein, the following terms and expressions have the indicated meanings. It will be appreciated that the compounds of the present invention contain asymmetrically substituted carbon atoms and may be isolated in optically active or racemic forms. It is well known in the art how to prepare optically active forms such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, the suitable indicated groups can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O)$_2$, —P(=O)(OH)$_2$, —C(=O)R, —C(=O)X, —C(S)R, —C(O)OR, —C(O)O, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is oxo (=O) or thioxo (=S), or the like, then two hydrogen atoms on the substituted atom are replaced.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings or from 3 to 7 carbon atoms or from 5 to 6 carbon atoms. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" or "Ar" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms or from 6 to 20 carbon atoms or from 6 to 12 carbon atoms or from 6 to 10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2 to 20 carbon atoms in addition to the one or more heteroatoms or 5 to 15 carbon atoms in addition to the one or more heteroatoms or 4 to 10 carbon atoms in addition to the one or more heteroatoms. Typical heteroaryl groups contain 6 to 30 ring atoms or 6 to 20 ring atoms or 6 to 12 ring atoms or 6 to 10 ring atoms. Suitably the heteroaryl contains up to 4 heteroatoms or 3 heteroatoms or 2 heteroatoms.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl.

In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (═O) or a thioxo (═S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs* (John Wiley & Sons, New York, 1950 to present), in particular Volumes 13, 14, 16, 19, and 28; and *J. Am. Chem. Soc.* 1960, 82, 5566. Typical heteroaryl groups contain 2 to 20 carbon atoms in addition to the one or more heteroatoms or 5 to 15 carbon atoms in addition to the one or more heteroatoms or 4 to 10 carbon atoms in addition to the one or more heteroatoms. Typical heteroaryl groups contain 6 to 30 ring atoms or 6 to 20 ring atoms or 6 to 12 ring atoms or 6 to 10 ring atoms. Suitably the heterocycle contains up to 4 heteroatoms. In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(═O)R, wherein R is an alkyl group as previously defined.

The term "acyloxy" or "alkylcarboxy" refers to —O—C(═O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(═O)OR (or "COOR"), wherein R is an alkyl group as previously defined.

The term "amino" refers to —NH$_2$. The amino group can be optionally substituted as defined herein for the term "substituted".

The term "alkylamino" refers to —NR$_2$, wherein at least one R is alkyl and the second R is alkyl or hydrogen.

The term "acylamino" refers to N(R)C(=O)R, wherein each R is independently hydrogen, alkyl, or aryl.

The term "interrupted" indicates that another group is inserted between two adjacent carbon atoms (and the hydrogen atoms to which they are attached (e.g., methyl (CH$_3$), methylene (CH$_2$) or methine (CH))) of a particular carbon chain being referred to in the expression using the term "interrupted, provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

The term "luciferase," unless specified otherwise, refers to a naturally occurring, recombinant or mutant luciferase. The luciferase, if naturally occurring, may be obtained easily by the skilled person from an organism. If the luciferase is one that occurs naturally or is a recombinant or mutant luciferase, e.g., one which retains activity in a luciferase-luciferin reaction of a naturally occurring luciferase, it can be obtained readily from a culture of bacteria, yeast, mammalian cells, insect cells, plant cells, or the like, transformed to express a nucleic acid encoding the luciferase. Further, the recombinant or mutant luciferase can be derived from an in vitro cell-free system using a nucleic acid encoding the luciferase. Luciferases are available from Promega Corporation, Madison, Wis.

As used herein, "bioluminescence" or "luminescence" is light produced as a result of a reaction between an enzyme and a substrate that generates light. Examples of such enzymes (bioluminescent enzymes) include firefly luciferase, e.g. *Photinus pyralis* or *Photinus pennslyvanica*, click beetle luciferase, *Renilla* luciferase, cypridina luciferase, *Oplophorus* luciferase, e.g. *Oplophorous gracilirostris*, Aequorin photoprotein, obelin photoprotein and the like.

A "bioluminescent reporter moiety" refers to a moiety that is a substrate for a luciferase. For example, the bioluminescent reporter moiety can be a luciferin, a luciferin derivative, a coelenterazine or a coelenterazine derivative.

A "luciferase reaction mixture" contains a luciferase enzyme and materials that will allow the luciferase enzyme to generate a light signal. The materials needed, and the particular concentrations and/or amounts, of the materials needed to generate a luminescent signal will vary depending on the luciferase enzyme used as well as the type of luciferase-based assay being performed. In general, for firefly luciferase, these materials can include: ATP, a magnesium (Mg$^{2+}$) salt, such as magnesium sulfate, and a firefly luciferase enzyme, e.g., a thermostable firefly luciferase. Often other materials will be added to the solution including: a buffer to maintain the reaction at the proper pH, an additive such as PRIONEX or Bovine serum albumin (BSA) to help maintain luciferase activity, reducing agents, detergents, e.g., for cell lysis, esterases, salts, amino acids, e.g. D-cysteine, etc. An example luciferase reaction mixture would contain a thermostable firefly luciferase, MgSO$_4$, ATP, Tergitol NP-9, and Tricine. An alternative example luciferase reaction mixture would include *Oplophorus* luciferase, e.g., NanoLuc luciferase, buffer, e.g., Tris-Cl or Tris base, and optionally a background reduction agent, e.g., TCEP.

The term "diaphorase" refers to a naturally occurring, recombinant or mutant diaphorase. They can be of bacterial, such as from *Clostridium kluveri* or animal origin, such as from human and rat. Diaphorases are available from Sigma Corporation, St. Louis, Mo. and Worthington Biochemical Corporation, Lakewood, N.J.

As used herein, the term "amplification enzyme system" refers to an enzyme system involved in the cycling or amplification of dinucleotide, e.g., NAD or NADP. An amplification enzyme system contains an amplification enzyme and a substrate for the enzyme. For example, NAD can be cycled or amplified into NADH by a dehydrogenase amplification enzyme, e.g., alcohol dehydrogenase, in the presence of a substrate for the amplification enzyme, e.g., ethanol. Examples of amplification enzymes include alcohol dehydrogenase (ADH), lactate dehydrogenase (LDH) and glucose-6-phosphate (G6P) dehydrogenase.

Compounds

The invention provides compounds according to Formula (I):

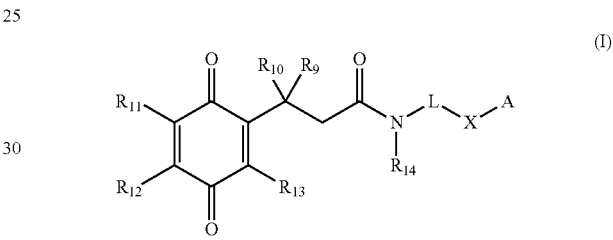

wherein A is a bioluminescent reporter moiety;
$R_{14}$ is H, $C_{1-4}$ alkyl, $C_{1-4}$ alkoxyl, $C_{2-4}$ hydroxylalkyl, $C_{2-4}$alkoxyl, $C_{2-4}$ carboxylic acid, $C_{2-4}$ amide;
$R_9$ and $R_{10}$ are independently selected from $C_{1-4}$ alkyl;
$R_{11}$, $R_{12}$ and $R_{13}$ are independently selected from H, $C_{1-4}$ alkyl, $C_{1-4}$ alkoxyl, bromo, chloro or amino, or $R_{11}$ and $R_{12}$ can form a fused phenyl ring;
X is O, NH or a direct bond;
L is a direct bond or —C$_6$(R$_{16}$)$_4$CH$_2$— or —(CH$_2$)$_m$C(R$_{17}$)$_2$(CH$_2$)$_n$—Y—C(O)—;
$R_{16}$ is independently H, halogen, CH$_3$, OCH$_3$, or NO$_2$;
$R_{17}$ is independently H, $C_{1-4}$ alkyl or both $R_{17}$ together can form an alkyl ring having from 3-7 carbons;
m is an integer from 0-2;
n is an integer from 0-2;
Y is O or NR$_{15}$; and
$R_{15}$ is H, $C_{1-4}$ alkyl, $C_{2-4}$ hydroxylalkyl, $C_{2-4}$alkoxyl, $C_{2-4}$ carboxylic acid, or $C_{2-4}$ amide.

The invention also provides compounds according to Formula (II):

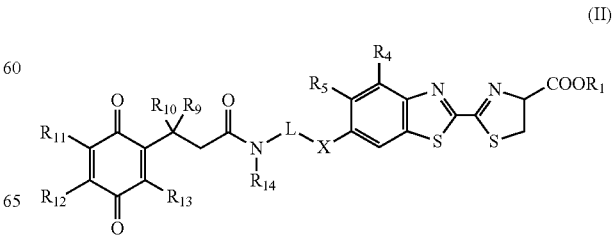

wherein $R_1$ is H, $C_{1-4}$ alkyl, $C_{1-4}$ hydroxylalkyl, $C_{3-7}$ cyclic ring, aryl, benzyl or substituted benzyl ring, heterocycle, heteroaryl and —$(CH_2)_{n'}$—$P(Ph)_3$;

$R_4$ and $R_5$ are independently selected from H, halogen, methyl, and trifluoromethyl;

$R_{14}$ is H, $C_{1-4}$ alkyl, $C_{1-4}$ alkoxyl, $C_{2-4}$ hydroxylalkyl, $C_{2-4}$alkoxyl, $C_{2-4}$ carboxylic acid, or $C_{2-4}$ amide;

$R_9$ and $R_{10}$ are independently selected from $C_{1-4}$ alkyl;

$R_{11}$, $R_{12}$ and $R_{13}$ are independently selected from H, $C_{1-4}$ alkyl, $C_{1-4}$ alkoxyl, bromo-, chloro- or amino-, or $R_{11}$ and $R_{12}$ can form a fused phenyl ring;

X is O, NH or a direct bond;

L is a direct bond or —$C_6(R_{16})_4CH_2$— or —$(CH_2)_mC(R_{17})_2(CH_2)_n$—Y—C(O)—;

$R_{16}$ is independently H, halogen, $CH_3$, $OCH_3$, or $NO_2$;

$R_{17}$ is independently H, $C_{1-4}$ alkyl or both $R_{17}$ together can form an alkyl ring having from 3-7 carbons;

m is an integer from 0-2;

n is an integer from 0-2;

Y is O or $NR_{15}$; and $R_{15}$ is H, $C_{1-4}$ alkyl, $C_{2-4}$ hydroxylalkyl, $C_{2-4}$alkoxyl, $C_{2-4}$ carboxylic acid, or $C_{2-4}$ amide;

n' is an integer from 2-7.

The invention also provides compounds according to Formula (III):

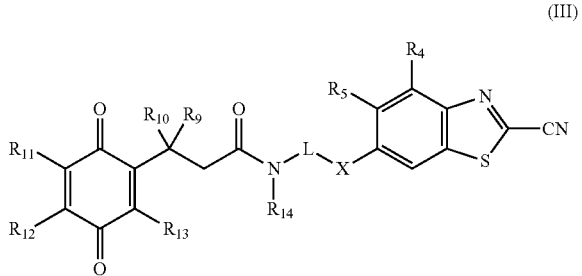

(III)

wherein $R_4$ and $R_5$ are independently selected from H, halogen, methyl, and trifluoromethyl;

$R_{14}$ is H, $C_{1-4}$ alkyl, $C_{1-4}$ alkoxyl, $C_{2-4}$ hydroxylalkyl, $C_{2-4}$alkoxyl, $C_{2-4}$ carboxylic acid, or $C_{2-4}$ amide;

$R_9$ and $R_{10}$ are independently selected from $C_{1-4}$ alkyl;

$R_{11}$, $R_{12}$ and $R_{13}$ are independently selected from H, $C_{1-4}$ alkyl, $C_{1-4}$ alkoxyl, bromo, chloro or amino, or $R_{11}$ and $R_{12}$ can form a fused phenyl ring;

X is O, NH or a direct bond;

L is a direct bond or —$C_6(R_{16})_4CH_2$— or —$(CH_2)_mC(R_{17})_2(CH_2)_n$—Y—C(O)—;

$R_{16}$ is independently H, halogen, $CH_3$, $OCH_3$, or $NO_2$;

$R_{17}$ is independently H, $C_{1-4}$ alkyl or both $R_{17}$ together can form an alkyl ring having from 3-7 carbons;

m is an integer from 0-2;

n is an integer from 0-2;

Y is O or $NR_{15}$; and $R_{15}$ is H, $C_{1-4}$ alkyl, $C_{2-4}$ hydroxylalkyl, $C_{2-4}$alkoxyl, $C_{2-4}$ carboxylic acid, or $C_{2-4}$ amide;

The invention also provides compounds according to Formula (IV):

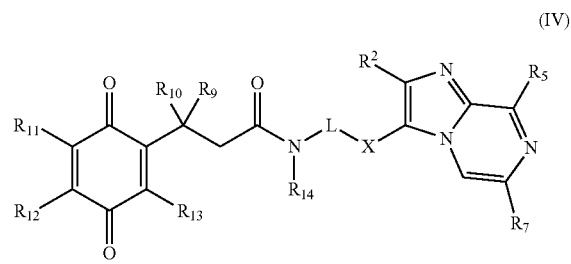

(IV)

wherein $R_2$ is selected from —$CH_2$-aryl or —$CH_2$-heteroaryl;

$R_5$ is selected from —$CH_2$-aryl or —$CH_2$-heteroaryl;

$R_7$ is selected from aryl or heteroaryl;

$R_{14}$ is H, $C_{1-4}$ alkyl, $C_{1-4}$ alkoxyl, $C_{2-4}$ hydroxylalkyl, $C_{2-4}$alkoxyl, $C_{2-4}$ carboxylic acid, or $C_{2-4}$ amide;

$R_9$ and $R_{10}$ are independently selected from $C_{1-4}$ alkyl;

$R_{11}$, $R_{12}$ and $R_{13}$ are independently selected from H, $C_{1-4}$ alkyl, $C_{1-4}$ alkoxyl, bromo, chloro or amino, or $R_{11}$ and $R_{12}$ can form a fused phenyl ring;

X is O, NH or a direct bond;

L is a direct bond or —$C_6(R_{16})_4CH_2$— or —$(CH_2)_mC(R_{17})_2(CH_2)_n$—Y—C(O)—;

$R_{16}$ is independently H, halogen, $CH_3$, $OCH_3$, or $NO_2$;

$R_{17}$ is independently H, $C_{1-4}$ alkyl or both $R_{17}$ together can form an alkyl ring having from 3-7 carbons;

m is an integer from 0-2;

n is an integer from 0-2;

Y is O or $NR_{15}$; and $R_{15}$ is H, $C_{1-4}$ alkyl, $C_{2-4}$ hydroxylalkyl, $C_{2-4}$alkoxyl, $C_{2-4}$ carboxylic acid, or $C_{2-4}$ amide.

Suitable compounds according to Formulas (I)-(IV) include those shown in FIG. 13A.

Synthesis of Compounds

Compounds described herein may be synthesized using a variety of methods. Exemplary syntheses are generalized below.

For a typical quinone benzylinker luciferin or fluorophore compound, quinone propionic acid was coupled with an aminobenzylalcohol derivative by a standard coupling method. The resulting product quinone benzylalcohol was converted to benzyl bromide. Benzyl bromide was directly coupled to a phenol-type fluorophore to give a final compound or coupled with 2-cyano-6-hydroxyl benzothiazole and reacted with D-cysteine to yield quinone benzyllinker luciferin compound (Scheme 1). A typical method for syntheses of quinone benzyllinker luciferin and fluorophore compounds is shown in Scheme 1.

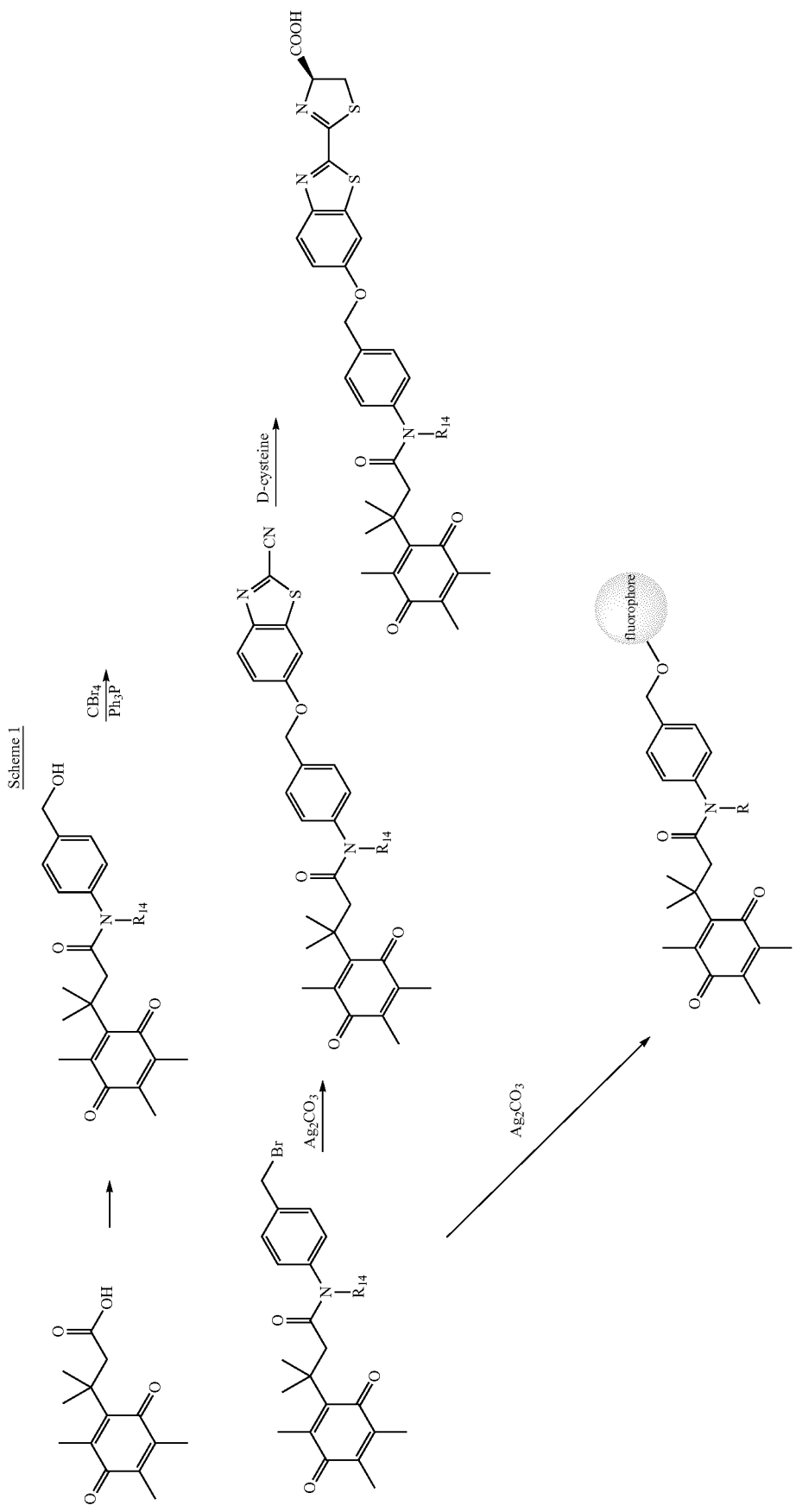
Scheme 1

For a typical diamine linker luciferin or fluorophore compound, quinone propionic acid was coupled with a suitable Boc protected diamine linker by a standard coupling method. After removal of the protecting group, the resulting quinone-amine TFA salt was then converted to carbonyl chloride by reacting with an excess phosgene. The carbonyl chloride was directly coupled to a phenol-type fluorophore or coelenterazine to give the final compound quinone-diamine-fluorophore or quinone-diamine-coelenterazine or coupled with 2-cyano-6-hydroxyl benzothiazole and reacted with D-cysteine to yield quinone diamine luciferin compound (Scheme 2). A typical method for syntheses of quinone diamine linker luciferin, coelenterazine and fluorophore compounds is shown in Scheme 2.

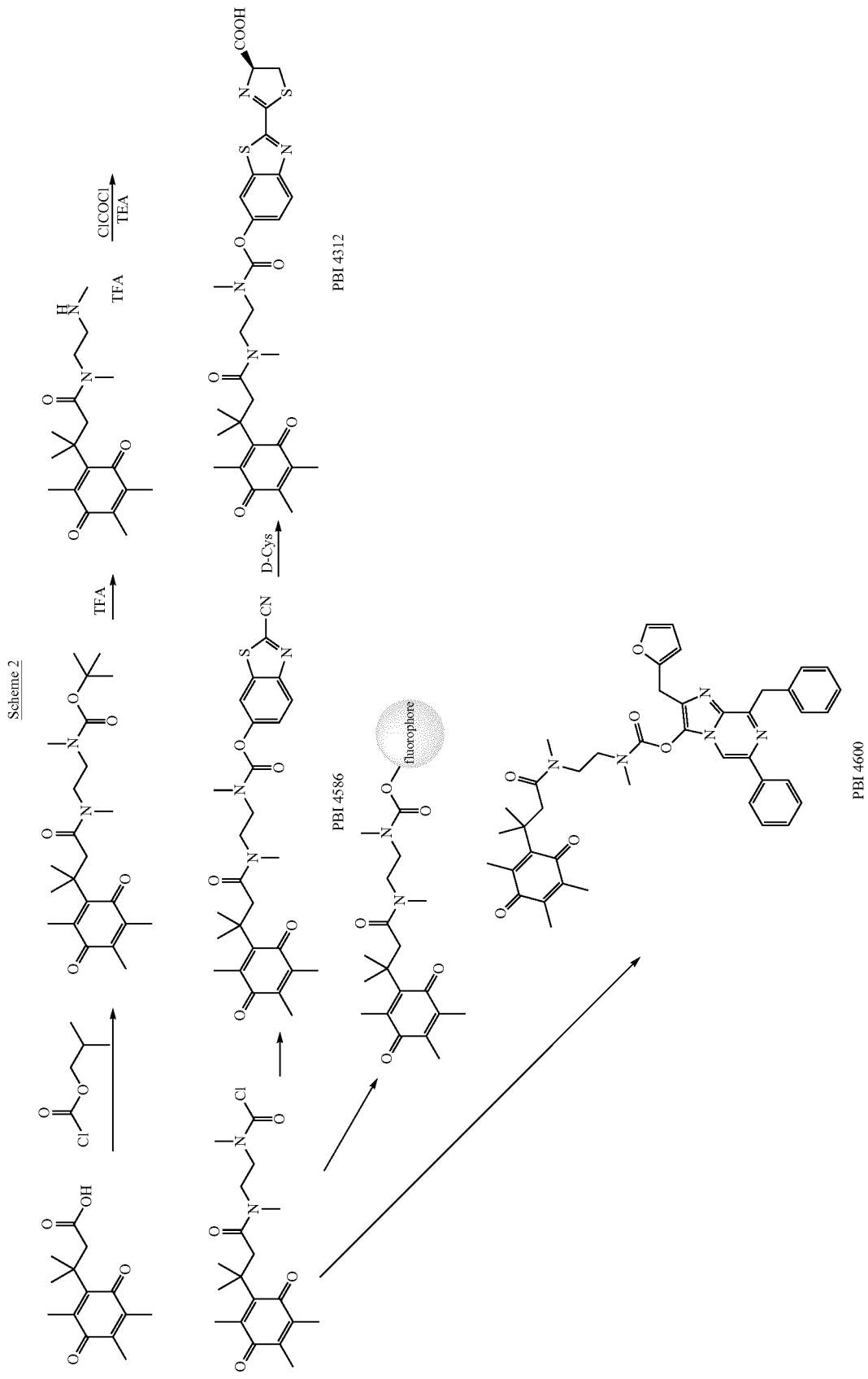

As can be appreciated by the skilled artisan, alternative methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Methods of Use

Methods for Measuring Redox State of Metabolically Active Cells

In another aspect, the invention provides various methods for analyzing the redox state of a metabolically active cellular sample. In one embodiment, a cell(s), media sample, physiological fluid, e.g., plasma, serum, urine, etc., or mitochondria or mitochondrial complex or enzyme(s) is contacted with a compound according to Formulae (I)-(IV) described herein to form a first mixture. At least a portion of the first mixture is contacted with a luciferase reaction mixture. Bioluminescence is detected. The amount of bioluminescence generated is directly proportional to redox state. In certain embodiments, D-cysteine is added to the mixture.

In another embodiment of the present invention, a cell(s), media sample, physiological fluid, e.g., plasma, serum, urine, etc., or mitochondria or mitochondrial complex(es) or enzyme(s) is contacted with a compound according to Formula (I)-(IV) described herein, a luciferase reaction mixture is added to the contacted cell(s), media sample, physiological fluid, e.g., plasma, serum, urine, etc., or mitochondria or mitochondrial complex(es) or enzyme(s), and bioluminescence is detected. The amount of bioluminescence generated is directly proportional to redox state. In certain embodiments, D-cysteine is also added to the contacted sample.

In a further embodiment, a cell(s), media sample, physiological fluid, e.g., plasma, serum, urine, etc., or mitochondria or mitochondrial complex(es) or enzyme(s) is contacted with a compound according to Formula (V), and fluorescence is detected. Fluorescence is indicative of the redox state. Only live cells are capable of reducing the compounds of the present invention, and as a result, a non-fluorescent compound is converted to a fluorescent compound in the presence of a metabolically active cell.

The methods of the present invention may also be used to measure cell viability and cell toxicity. As one of skill in the art would recognize, a metabolically active state is inevitably lost when cells are damaged.

In addition, the methods of the present invention may be used to measure mitochondria redox activity in intact cells and isolated organelles. The methods of the present invention may be used to measure redox activities of mitochondria protein complexes and to screen for compounds which affect the redox state of a cell and/or cell viability.

Methods for Measuring NAD(P)/NAD(P)H Levels and Ratios

The present invention provides methods for measuring reduced co-enzyme forms, i.e., NADH and NADPH, using diaphorase. In one embodiment, a cell lysate or purified enzyme preparation is contacted with a diaphorase and a compound according to Formula (I)-(V) described herein. The reduced co-enzyme forms are oxidized by the diaphorase, and in the same enzymatic reaction, bioluminogenic or fluorogenic quinones are oxidized to generate products that are suited for bioluminescent or fluorescent detection. The amount of NADH or NADPH can be measured quantitatively by monitoring light produced by luciferase reaction or light generated by fluorescent products.

The methods of the present invention may also be used to measure the reduced co-enzyme forms NADH or NADPH directly in a cell lysate or purified enzyme preparation. The amount of reduced co-enzymes can be determined directly in a cell lysate with no prior extraction of the reduced forms required.

Additionally, the methods of the present invention may be used to determine the presence or amount of the total reduced and oxidized co-enzyme forms present in a cell lysate or purified enzyme preparation. The total oxidized forms and reduced forms, i.e., NADP(H) and NAD(H), present are amplified with a dehydrogenase, e.g., lactate dehydrogenase (LDH) or glucose-6-phosphate dehydrogenase (G6P-DH), in the presence of a diaphorase and a compound according to Formulas (I)-(V) with no prior extraction of forms required. Other amplification enzymes can be used including any dehydrogenase enzyme, e.g., alcohol dehydrogenase (ADH).

The methods of the present invention may also be used to measure the ratio of reduced and oxidized co-enzyme forms. In this method, the oxidized and reduced forms are differentially extracted, e.g., oxidized in acid solution and reduced in basic solution with heat. An amplification enzyme is then added to each extracted sample, i.e., one containing the reduced forms and one containing the oxidized forms. A diaphorase and a compound of the present invention are then added to each extracted sample. The conversion of the compound is then detected.

In addition, the methods of the present invention may be used to detect oxidized and reduced co-enzymes in homogenous samples in a single reaction vessel. The methods of the present invention do not require extraction and separation of extracted material by spinning down cell debris, removing supernatant, neutralizing it and then measuring amount of nucleotides using enzyme cycling approach.

In addition, in some embodiments the method of the present invention reduces to one step the manipulations needed for measuring NAD(P)/NAD(P)H co-enzymes in the sample. In such a method, all the necessary components for cycling enzyme system, diaphorase reaction and luciferin/luciferase detection reaction are combined before contacting the sample.

In addition, the method of the present invention can be used to measure conversion of reduced forms to oxidized forms. The reduced forms are selectively eliminated while oxidized forms are detected using the method described herein.

Methods for Measuring Enzyme Activities

As NAD, NADP, NADH and NADPH are utilized and/or produced by many enzymes, e.g. formaldehyde dehydrogenase (the NAD utilizing enzyme) and isocitrate dehydrogenase, the above mentioned detection methods can be used to assay the presence and activities of these enzymes. These enzymes can be purified enzymes, enzymes present in protein complexes, enzymes present in isolated cellular organelles or enzymes present in cell lysates. In one embodiment, a purified enzyme preparation is reacted with its substrates and NAD or NAD(P), as appropriate. The reaction is contacted with a compound of Formula (I)-(IV), a diaphorase and luciferase reaction mixture. Bioluminescence is then detected. Bioluminescence is indicative of the presence of NAD(P)H in the sample, indicating production of the NAD(P)H, and thereby enzyme presence and/or activity.

Enzymes that themselves do not use or produce NAD, NADP, NADH or NAD(P)H can also be detected and measured if their substrate or product can be utilized by an enzyme that does. In one embodiment, an enzyme of interest is reacted with its substrate(s) to produce a product(s). At least one of those products can be utilized by another enzyme that is capable of producing NAD(P)H. The reaction is contacted with a compound of Formula (I)-(IV), a diaphorase and luciferase reaction mixture. Bioluminescence is then detected. Bioluminescence is indicative of the presence of NAD(P)H which indicates the presence and/or activity of the enzyme of interest. A compound of Formula (V) may also be used and fluorescence detected.

Methods for Measuring Cellular Metabolites

The present invention also provides a method for measuring cellular metabolites. In one embodiment, a cell lysate or other sample containing the metabolite of interest is contacted with a compound according to Formulae (I)-(V) described herein, a diaphorase, NAD(P) and a dehydrogenase enzyme, e.g. LDH, ADH, G6P-DH. If the compound is one according to Formulae (I)-(IV), a luciferase detection reagent is added, and luminescence is detected. If the compound is one according to Formulae (V), fluorescence is detected. Luminescence or fluorescence indicates the presence of the cellular metabolite of interest. In some embodiments, particularly, those using firefly luciferase, a diaphorase inhibitor is added. In some instances, even when using firefly luciferase or other bioluminescent detection methods, the diaphorase inhibitor is not needed. For example, if looking at real-time utilization of a co-enzyme, no diaphorase inhibitor is needed.

The selection of dehydrogenases depends on the analyte to be detected as the analyte must be a substrate for the dehydrogenase. Dehydrogenases catalyze analyte conversion to the product using NAD(P) as co-factor and reducing it to NAD(P)H. The NAD(P)H generated is utilized by the diaphorase in the presence of the compound according to Formulae (I)-(V).

The methods of the present invention may also be used for measuring analytes that can be detected by coupling to NAD(P)H production. Additionally, the methods of the present invention may be used for measuring major metabolites that reflect redox state balance of the cells, e.g., lactate, pyruvate, beta-hydroxybutyrate, acetoacetate.

The methods of the present invention may also be used for measuring glycolytic rate of the cells by measuring changes in lactate production. In addition, the methods of the present invention may also be used for measuring oxidative phosphorylation rate.

Further, the methods of the present invention may be used for measuring lactate/pyruvate ratio as readout of free NAD(P)/NAD(P)H ratio in the cells or other organelle specific analytes for determining free NAD(P)/NAD(P)H ratio in those organelles. The methods of the present invention may also be used for measuring glucose uptake by following glucose-6-phosphate (G6P) formation.

General Information

In any of these embodiments, the reagents may be added sequentially or simultaneously. If the reagents are added simultaneously, they may be in a single solution or multiple solutions. In some embodiments, the amplification enzyme, diaphorase, and luciferase detection reagent are provided as a single reagent composition. In some embodiments, the amplification enzyme, compound described herein, diaphorase, and luciferase detection reagent are provided as a single reagent composition.

The signal may be quantified if desired. The signal may be compared to a standard curve. The intensity of the signal is a function of the amount of NAD(P)H in the sample. The signal generated may be compared to a control. Suitable controls lack one or more of the necessary components or conditions for either the reaction between the compound and the diaphorase or the luciferase reaction. Such components or conditions include, but are not limited to, co-factors, enzymes, temperature, and inhibitors.

The methods of the present invention are useful in cells grown in culture medium, i.e., in vitro, or in cells within animals, e.g., living animals, i.e., in vivo. For research purposes, for measurements in cells in vivo, a compound according to Formula (I)-(V) described herein is administered, e.g., injected into the animal or added to an aqueous solution, e.g., water, or food consumed by the animal, to the animal. If the compound is of Formula (I)-(IV), the luciferase may be expressed in cells in the animal, e.g., whole animal imaging of a transgenic animal (e.g., mice, rats, and marmoset monkeys) or administered to the animal, e.g., injected into the animal. The methods of the present invention may be used in intact cells or in isolated organelles.

Cells may be eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may have been genetically modified via recombinant techniques. In certain aspects, the cell may be in an animal, e.g., transgenic animals, or physiological fluid, e.g., blood, plasma, urine, mucous secretions or the like. Destruction of the cells is not required as the media can be sampled.

The methods of the present invention may also use physiological fluids, e.g., blood, plasma, urine, and the like, tissue samples or DNA preparations.

In addition, for any of the assays described herein, other reagents may be added to reaction mixtures including, but not limited to, those that inhibit or prevent inactivation of luciferase, or otherwise extend or enhance the signal.

Suitable substrates include, but are not limited to, compounds of Formulas (I)-(IV) described herein. In addition, for cell-based assays, compounds of Formula (V) described herein are suitable.

Suitable substrates include, but are not limited to, compounds of Formulas (I)-(IV) described herein. In addition, for cell-based assays, compounds of Formula (V) are also suitable:

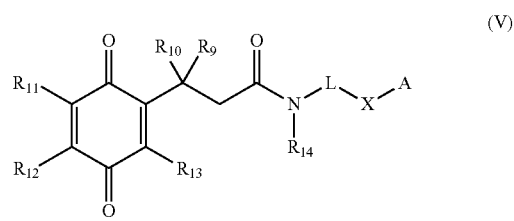

wherein A is a fluorescent reporter moiety, including but not limiting to fluorescein derivatives, Rhodamine derivatives, rhodol derivatives, resorufin, or cresyl violet;

$R_{14}$ is H, $C_{1-4}$ alkyl, $C_{1-4}$ alkoxyl, $C_{2-4}$ hydroxylalkyl, $C_{2-4}$ alkoxyl, $C_{2-4}$ carboxylic acid, or $C_{2-4}$ amide;

$R_9$ and $R_{10}$ are independently selected from $C_{1-4}$ alkyl;

$R_{11}$, $R_{12}$ and $R_{13}$ are independently selected from H, $C_{1-4}$ alkyl, $C_{1-4}$ alkoxyl, bromo, chloro or amino, or $R_{11}$ and $R_{12}$ can form a fused phenyl ring;

X is O, NH or a direct bond;

L is a direct bond or —$(C_6H_4)CH_2$— or —$(CH_2)_m C(R_{17})_2$ $(CH_2)_n$—Y—C(O)—;

$R_{16}$ is independently H, halogen, $CH_3$, $OCH_3$, or $NO_2$;

$R_{17}$ is independently H, $C_{1-4}$ alkyl or both $R_{17}$ together can form an alkyl ring having from 3-7 carbons;

Y is O or $NR_{15}$ $R_{15}$ is H, $C_{1-4}$ alkyl, $C_{2-4}$ hydroxylalkyl, $C_{2-4}$ alkoxyl, $C_{2-4}$ carboxylic acid, or $C_{2-4}$ amide;

m is an integer from 0 to 2; and n is an integer from 0 to 2.

Suitable compounds according to Formula (V) are shown in FIG. 13B.

Certain substrates may be particularly advantageous for use in various embodiments of this invention. For example, certain substrates may be better suited to use in vitro, and others may be better suited to use in vivo. As would be recognized by one of ordinary skill in the art, not all borates would be suitable for use in the methods of the present invention.

The invention is further described by the following non-limiting examples.

EXAMPLES

Example 1

Synthesis of PBI 1482

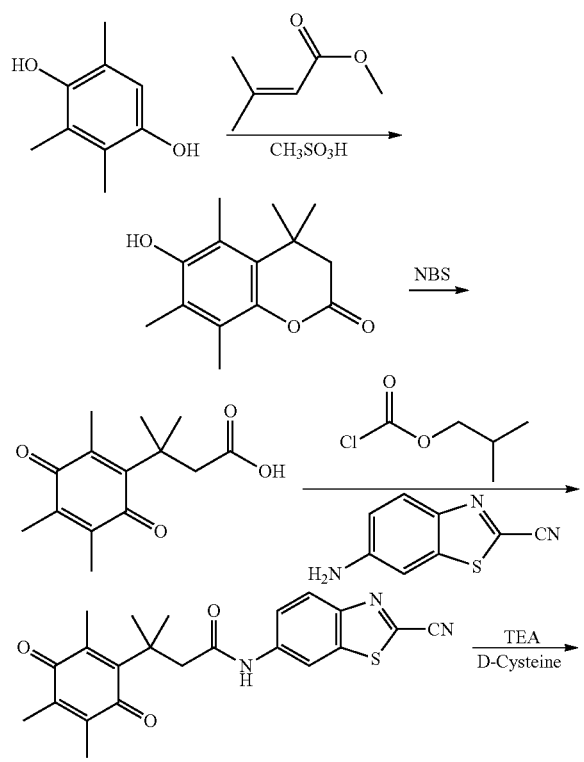

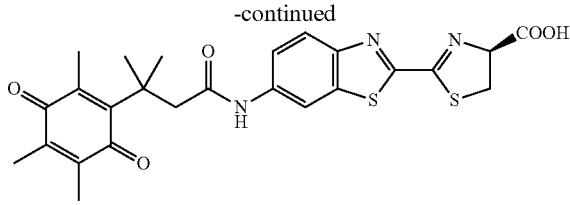

PBI 1482

6-hydroxy-4,4,5,7,8-pentamethylchroman-2-one

A mixture of 2,3,5-trimethyl hydroquinone (10 g, 0.0657 mol) and methyl 1,1-dimethylacrylate (7.5 g, 0.0657) in 50 ml of methanesulfonic acid was heated to 70° C. for 2 hours. Upon cooling to room temperature, the mixture was poured into 100 ml of ice-cold water. The resulting mixture was extracted three times with ethyl acetate, and the combined organic layers were washed with water and dried over sodium sulfate. After removal of the majority of ethyl acetate, the mixture was cooled –20° C. The pale white solid was collected by filtration, washed with cold ethyl acetate and dried under vacuum oven. The yield was 75%. $^1$H NMR (300 MHz, $CD_2Cl_2$) δ ppm: 4.69 (s, 1H, OH), 2.59 (s, 2H, CH2), 2.53 (s, 3H, CH3), 2.35 (s, 3H, CH3), 2.20 (s, 3H, CH3), 1.57 (s, 3H, CH3), 1.44 (s, 3H, CH3); MS (m/e): 235 ($M^+$).

3-Methyl-3-(2,4,5-trimethyl-3,6-dioxocyclohexa-1,4-dien-1-yl)butanoic acid

To the solution of 6-hydroxy-4,4,5,7,8-pentamethylchroman-2-one (15 g, 0.064 mol) in a mixture of acetonitrile (600 ml), acetone (50 ml) and water (300 ml), NBS (11.4 g, 0.064 mol) was added. The resultant mixture was stirred for 30 minutes at room temperature. After removing most of the organic solvent, the yellow solid was collected by filtration, washed by water and dried over vacuum to afford a yield of 96%. $^1$H NMR (300 MHz, $CD_2Cl_2$) δ 3.0 (s, 2H, CH2), 2.13 (s, 3H, $CH_3$), 1.94 (s, 3H, CH3), 1.92 (s, 3H, CH3), 1.44 (s, 6H, CH3); MS (m/e): 251 ($M^+$).

N-(2-Cyanobenzo[d]thiazol-6-yl)-3-methyl-3-(2,4,5-trimethyl-3,6-dioxocyclohexa-1,4-dien-1-yl)butanamide To the solution of 3-methyl-3-(2,4,5-trimethyl-3,6-dioxocyclohexa-1,4-dien-1-yl)butanoic acid (0.72 g, 3.09 mmol) and isobutyl chloroformate (0.44 g, 3.24 mmol) in 10 ml of dry THF, N-methyl morphorline (0.34 ml) was added at 0° C. The resultant mixture was stirred for 30 minutes at 0° C., and 6-amino-2-cyanobenzothiazole (0.36 g, 2.06 mmol) added. The resultant mixture was stirred overnight. The compound was directly purified with flash silica column using heptane and ethyl acetate as eluent to give a yield 10%. $^1$H NMR (300 MHz, $CD_2Cl_2$) δ 8.57 (d, J=2.0, 2H), 8.06 (d, J=9.0, 2H), 7.67 (s, 1H), 7.40 (dd, J=2.1, 8.9, 1H), 3.08 (s, 2H, CH2), 2.22 (s, 3H, CH3), 2.22 (s, 3H, CH3), 1.99 (s, 3H, CH3), 1.97 (s, 3H, CH3), 1.50 (s, 6H, CH3). MS (m/e): 408 ($M^+$).

Quinone-trimethyllock-aminoluciferin (PBI 1482)

To the solution of N-(2-cyanobenzo[d]thiazol-6-yl)-3-methyl-3-(2,4,5-trimethyl-3,6-dioxocyclohexa-1,4-dien-1-yl) butanamide (0.05 g, 0.128 mmol) in $MeOH/CH_2Cl_2$ (10 ml), D-cysteine (0.45 g, 0.256 mmol) and TEA (0.070 ml) in 3 ml water was added. The mixture was stirred for 10 minutes, and the pH adjusted to pH 6 with acetic acid. After removal of $CH_2Cl_2$, the compound was purified with HPLC using 0.1%

TFA/acetonitrile as eluent. ¹H NMR (300 MHz, CD₃CN) δ 8.67 (s, br, 1H, NH), 8.38 (s, 1H), 7.95 (d, J=8.9, 1H), 7.48 (d, J=8.9, 1H), 5.37 (t, J=9.2, 1H), 3.74 (d, J=9.2, 2H, SCH₂), 3.08 (s, 2H, CH2), 2.12 (s, 3H, CH3), 1.94 (s, 6H, CH3), 1.48 (s, 6H, CH3); MS (m/e): 512.3 (M⁺); HPLC purity: 97% at 330 nm.

Example 2

Synthesis of PBI 4200

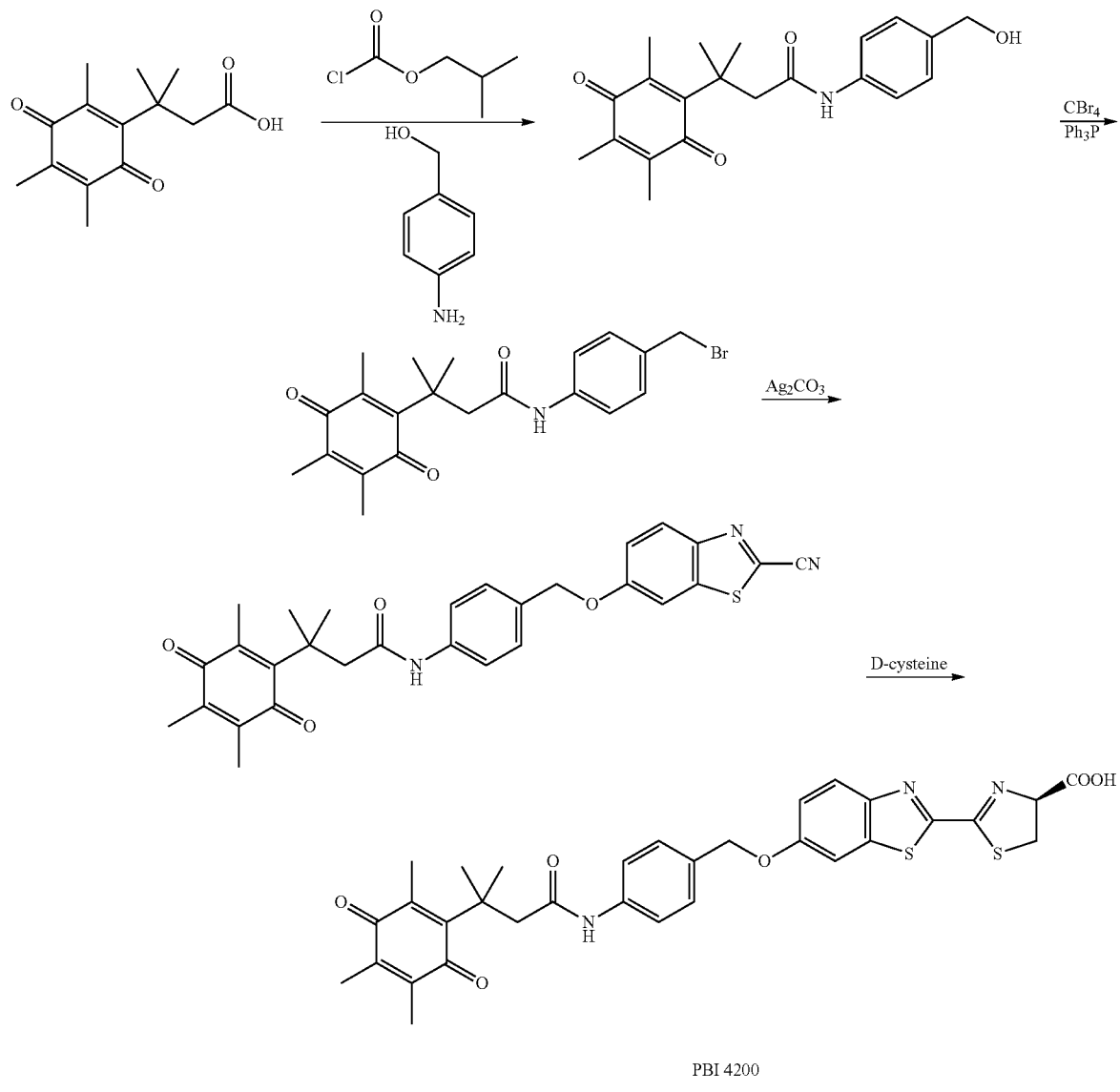

PBI 4200

N-(4-(Hydroxymethyl)phenyl)-3-methyl-3-(2,4,5-trimethyl-3,6-dioxocyclohexa-1,4-dien-1-yl)butanamide To a solution of 3-methyl-3-(2,4,5-trimethyl-3,6-dioxocyclohexa-1,4-dien-1-yl)butanoic acid (1.75 g, 7.46 mmol) and isobutyl chloroformate (1.11 g, 8.12 mmol) in 20 ml of dry THF, N-methyl morpholine (0.82 ml) was added at 0° C. The resultant mixture was stirred for 30 minutes at 0° C., 4-aminobenzylalcohol (1.38 g, 11.2 mmol) added, and the resultant mixture stirred overnight. After removal of the solid by filtration, the compound was directly purified with silica chromatography using heptane and ethyl acetate as eluent to give a yield of 74%. ¹H NMR (300 MHz, CD₂Cl₂) δ 7.40 (d, J=9, 2H), 7.28 (d, J=9, 2H), 7.19 (s, br, 1H, NH), 4.61 (s, 2H, CH2O), 2.99 (s, 2H, CH2), 2.14 (s, 3H, CH3), 1.97 (s, 6H, CH3), 1.55 (s, 3H, CH3), 1.48 (s, 3H, CH3). MS (m/e): 356 (M⁺).

N-(4-(Bromomethyl)phenyl)-3-methyl-3-(2,4,5-trimethyl-3,6-dioxocyclohexa-1,4-dien-1-yl)butanamide To a mixture of N-(4-(hydroxymethyl)phenyl)-3-methyl-3-(2,4,5-trimethyl-3,6-dioxocyclohexa-1,4-dien-1-yl)butanamide (1.35 g, 3.98 mmol) and carbon tetrabromide (3.96 g, 11.9 mmol) in methylene chloride (30 ml), Ph₃P (1.30 g, 4.77 mmol) was added at 0° C. The mixture was stirred for 3 hours at room temperature. The compound was directly purified with silica chromatography using heptane/ethyl acetate as eluent to give a yield of 31%. ¹H NMR (300 MHz, CD₂Cl₂) δ 7.41 (d, J=8.7, 2H), 7.32 (d, J=8.7, 2H), 7.25 (s, br, 1H, NH), 4.50 (s, 2H, CH₂Br), 3.00 (s, 2H, CH2), 2.14 (s, 3H, CH3), 1.95 (d, 6H, CH3), 1.48 (s, 6H, CH3). MS (m/e): 418, 420 (1:1, M⁺).

N-(4-(((2-cyanobenzo[d]thiazol-6-yl)oxy)methyl)phenyl)-3-methyl-3-(2,4,5-trimethyl-3,6-dioxocyclohexa-1,4-dien-1-yl)butanamide A mixture of N-(4-(bromomethyl)phenyl)-3-methyl-3-(2,4,5-trimethyl-3,6-dioxocyclohexa-1,4-dien-1-yl)butanamide (0.23 g, 0.57 mmol), 6-hydroxy-2-cyanobenzothiazole (0.15 g, 0.86 mmol), 2,4,6-collidine (0.125 ml) and Ag₂CO₃ (0.24 g, 0.86 mmol) in 15 ml of dry THF was stirred at room temperature over night. After removal of solid by filtration, the compound was purified by silica chromatography using heptane and ethyl acetate as eluent to give a yield of 40%. The product was further purified by HPLC to remove small contamination of 2-cyano-6-hydroxybenzothiazole. ¹H NMR (300 MHz, CD₂Cl₂) δ 7.4-7.5 (m, 3H), 7.35-7.42 (m, 2H), 7.32 (dd, 1H), 7.25 (s, br, 1H, NH), 7.18 (dd, 1H), 5.15 (s, 2H, CH2O), 2.99 (s, 2H, CH2), 2.14 (s, 3H, CH3), 1.92 (s, 6H, CH3), 1.47 (s, 6H, CH3). MS (m/e): 514.2 (M⁺).

Quinonetrimethyllock benzyl luciferin (PBI 4200)

To a solution of N-(4-(((2-cyanobenzo[d]thiazol-6-yl)oxy)methyl)phenyl)-3-methyl-3-(2,4,5-trimethyl-3,6-dioxocyclohexa-1,4-dien-1-yl)butanamide (0.052 g, 0.101 mmol) in 10 ml of CH₂Cl₂/MeOH, D-cysteine (0.0354 g, 0.202 mmol) and TEA (0.041 g, 0.0405 mmol) in 3 ml of water was added. The mixture was stirred for 10 minutes and then acidified to pH 6 with acetic acid. The compound was purified by HPLC using 0.1% formic acid and acetonitrile as eluent. ¹H NMR (300 MHz, CD₂Cl₂) δ 7.99 (d, J=8.9, 1H), 7.54-7.28 (m, 6H), 7.19 (d, J=9.0, 1H), 5.41 (t, J=9.4, 1H, CH), 5.07 (s, 2H, CH2O), 3.78 (d, J=9.6, 2H, CH2S), 3.01 (s, 2H, CH2), 2.14 (s, 3H), 1.95 (s, 6H), 1.48 (s, 6H, CH3). MS (m/e): 618.3 (M⁺); HPLC purity: 98.3% at 330 nm.

Example 3

Synthesis of PBI 4267

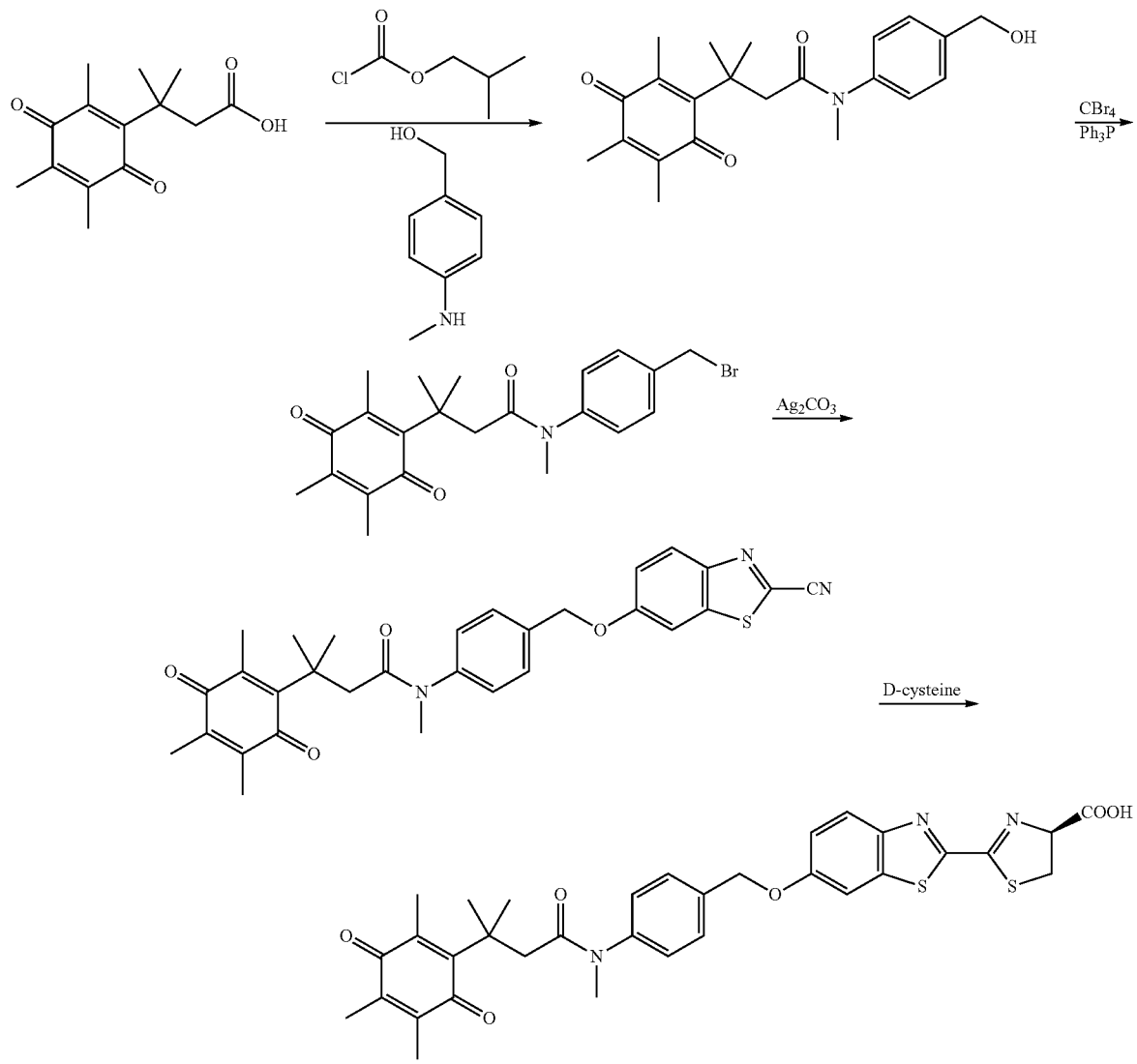

PBI 4267

PBI 4267 was prepared by employing the similar procedures for the synthesis of PBI 4200 (Example 2).

Quinone-trimethyllock-N-methyl-benzylalcohol $^1$H NMR (300 MHz, CD$_2$Cl$_2$) δ 7.44 (d, J=8.0, 2H), 7.20 (d, J=8.1, 2H), 4.73 (s, 2H, CH2O), 3.13 (s, 3H, NCH3), 2.72 (s, 2H, CH2), 2.08 (s, 3H, CH3), 1.99 (s, 3H, CH3), 1.96 (s, 3H, CH3), 1.29 (s, 6H, CH3). MS (m/e): 370.1 (M$^+$).

Quinone-trimethyllock-N-methyl-benzylbromide $^1$H NMR (300 MHz, CD$_2$Cl$_2$) δ 7.48 (d, J=8.2, 2H), 7.19 (d, J=8.3, 2H), 4.56 (s, 2H, CH2Br), 3.14 (s, 3H, NCH3), 2.74 (s, 2H, CH$_2$), 2.09 (s, 3H, CH3), 1.98 (d, 3H, CH3), 1.96 (s, 3H, CH3), 1.30 (s, 6H, CH3). MS (m/e): 432.1, 434 (1:1, M$^+$).

Quinone-trimethyllock-N-methyl-benzyl-2-cyanobenzothiazole $^1$H NMR (300 MHz, CD$_2$Cl$_2$) δ 8.14 (d, J=9.5, 1H), 7.62-7.46 (m, 3H), 7.37 (d, J=8.7, 1H), 7.27 (d, J=9.5, 2H), 5.22 (s, 2H, —OCH2), 3.15 (s, 3H, —NCH3), 2.75 (s, 2H, CH2), 2.09 (s, 3H, CH3), 1.98 (s, 3H, CH3), 1.96 (s, 3H, CH3), 1.31 (s, br, 6H, CH3). MS (m/e): 528 (M$^+$).

Quinonetrimethyllock N-methyl benzyl luciferin (PBI 4267)

$^1$H NMR (300 MHz, CD$_2$Cl$_2$) δ 8.05 (d, J=9.0, 1H), 7.64-7.45 (m, 3H), 7.27 (d, br, 3H), 5.44 (t, J=9.4, 1H, CH), 5.20 (s, 2H, OCH2), 3.79 (d, J=9.7, 2H, SCH2), 3.16 (s, 3H, NCH3), 2.76 (s, 2H, CH2), 2.09 (s, 3H, CH3), 1.98 (s, 3H, CH3), 1.96 (s, 3H, CH3), 1.31 (s, br, 6H, CH3); MS (m/e): 632.4 (M$^+$); HPLC purity: 98.8% at 330 nm.

Example 4

Synthesis of PBI 4296

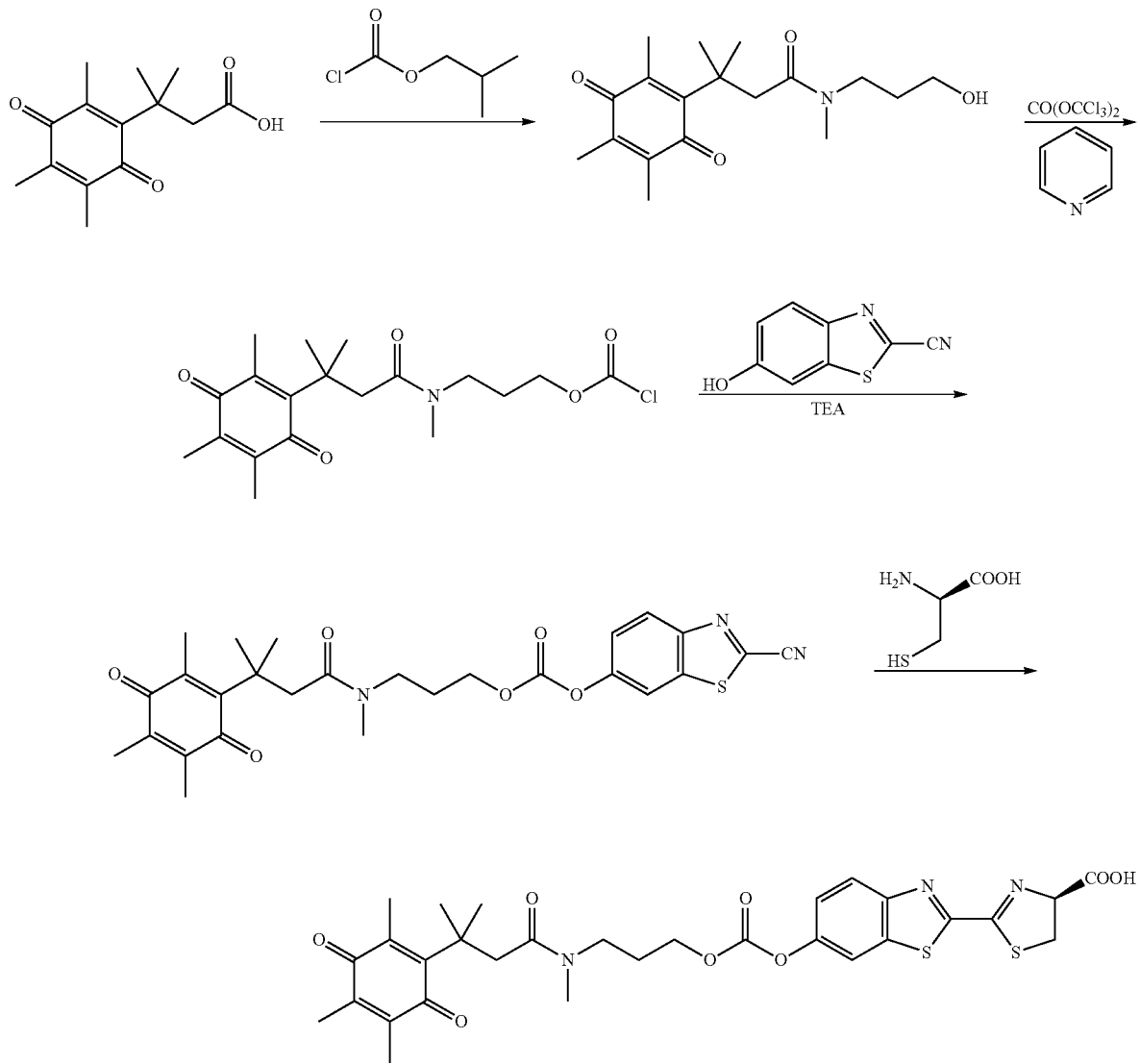

PBI 4296

N-(3-hydroxypropyl)-N,3-dimethyl-3-(2,4,5-trimethyl-3,6-dioxocyclohexa-1,4-dien-1-yl)butanamide To a solution of 3-methyl-3-(2,4,5-trimethyl-3,6-dioxocyclohexa-1,4-dien-1-yl)butanoic acid (2.0 g, 7.99 mmol) and isobutyl chloroformate (1.2 g, 8.79 mmol) in 50 ml dry THF, N-methyl morphorline (0.88 ml) was added at 0° C. The resultant mixture was stirred for 30 minutes at 0° C., and 3-N-methylpropanol (0.85 g, 9.59 mmol) added. The resultant mixture was stirred at room temperature overnight. The compound was directly purified by silica chromatography using heptane and ethyl acetate as eluent to give a yield of 100%. $^1$H NMR (300 MHz, CD$_2$Cl$_2$) δ 3.2-3.6 (m, 4H, NCH2+CH2O), 2.8-3.1 (m, 5H, NCH3+CH$_2$), 2.12 (s, 3H, CH3), 2.93 (s, 6H, CH3), 1.5-1.7 (m, 2H, CH2), 1.42 (s, 6H, CH3); MS (m/e): 322.1.

2-Cyanobenzo[d]thiazol-6-yl (3-(N,3-dimethyl-3-(2,4,5-trimethyl-3,6-dioxocyclohexa-1,4-dien-1-yl)butanamido)propyl)carbonate To a solution of N-(3-hydroxypropyl)-N,3-dimethyl-3-(2,4,5-trimethyl-3,6-dioxocyclohexa-1,4-dien-1-yl)butanamide (1.0 g, 3.11 mmol) and triphosgene (0.34 g, 1.09 mmol) in 20 ml of dry CH$_2$Cl$_2$, pyridine (0.25 g, 3.11 mmol) was added at 0° C., and the resultant mixture stirred for 30 minutes at room temperature. After removal of solvent under vacuum, the residue was dissolved in dry THF (20 ml), and 2-cyano-6-hydroxybenzothiazole (0.55 g, 3.11 mmol) and TEA (0.433 ml) in 10 ml of THF added at 0° C. The mixture was stirred for 2 hours at room temperature. The compound was purified by silica chromatography using heptane/ethyl acetate as eluent to give a yield of 38%. The compound might exist as two rotomers (7:3) due to non-free rotation caused by steric effects of trimethyl groups. Rotomer 1 (major): $^1$H NMR (300 MHz, CD$_2$Cl$_2$) δ 8.21 (d, J=9.0, 1H), 7.90 (d, J=2.3, 1H), 7.50 (dd, J=9.0, J=2.5, 1H), 4.21 (t, J=6, 2H, OCH2), 3.41 (t, J=6, 2H, NCH2), 2.9-3.1 (m, 5H, NCH3+CH$_2$), 2.12 (s, 3H, CH3), 1.8-2.0 (m, 8H, 2CH3+CH$_2$), 1.42 (s, 6H, CH3). Rotomer 2 (minor): $^1$H NMR (300 MHz, CD$_2$Cl$_2$) δ 8.25 (d, J=9.0, 1H), 7.92 (d, J=2.3, 1H), 7.53 (dd, J=9.0, J=2.5, 1H), 4.35 (t, J=6, 2H, OCH2), 3.47 (t, J=6, 2H, NCH2), 2.9-3.1 (m, 5H, NCH3+CH$_2$), 2.11 (s, 3H, CH3), 1.8-2.0 (m, 8H, 2CH3+CH$_2$), 1.42 (s, 6H, CH3). MS (m/e): 524 (M$^+$).

Quinone trimethyllock-C3-carbnate luciferin (PBI 4296)

To 2-Cyanobenzo[d]thiazol-6-yl (3-(N,3-dimethyl-3-(2,4,5-trimethyl-3,6-dioxocyclohexa-1,4-dien-1-yl)butanamido)propyl) carbonate (0.23 g, 0.44 mmol) in 10 ml of CH$_2$Cl$_2$/MeOH, D-cysteine (0.115 g, 0.66 mmol) and TEA (0.133 g, 1.31 mmol) in 5 ml of water was added. The mixture was stirred for 10 minutes and then acidified to pH 6 with acetic acid. The compound was purified by HPLC using 0.1% of formic acid and acetonitrile as eluent. The compound might exist as two rotomers (7:3). Rotomer 1 (major): $^1$H NMR (300 MHz, CD$_2$Cl$_2$) δ 8.12 (d, J=9.0, 1H), 7.85 (d, J=3.0, 1H), 7.38 (dd, J=9.0, J=3.0, 1H), 5.46 (t, J=9, 1H, CH), 4.23 (t, J=6, 2H, OCH2), 3.84 (d, J=9, 2H, SCH2), 3.42 (t, J=6, 2H, NCH2), 2.9-3.1 (m, 5H, NCH3+CH$_2$), 2.11 (s, 3H, CH3), 1.8-2.0 (m, 6H, CH3), 1.43 (s, 6H, CH3). Rotomer 2 (minor): $^1$H NMR (300 MHz, CD$_2$Cl$_2$) δ 8.15 (d, J=9.0, 1H), 7.86 (d, J=2.3, 1H), 7.41 (dd, J=9.0, J=2.5, 1H), 5.46 (t, J=9, 1H, CH), 4.36 (t, J=6, 2H, OCH2), 3.84 (d, J=9, 2H, SCH2), 3.47 (t, J=6, 2H, NCH2), 2.9-3.1 (m, 5H, NCH3+CH$_2$), 2.11 (s, 3H, CH3), 1.8-2.0 (m, 8H, 2CH3+CH$_2$), 1.43 (s, 6H, CH3). MS (m/e): 628.2 (M$^+$), 650.1 (MNa+); HPLC purity: 99.5% at 295 nm (two rotomers cannot be separated).

Example 5

Synthesis of PBI 4308

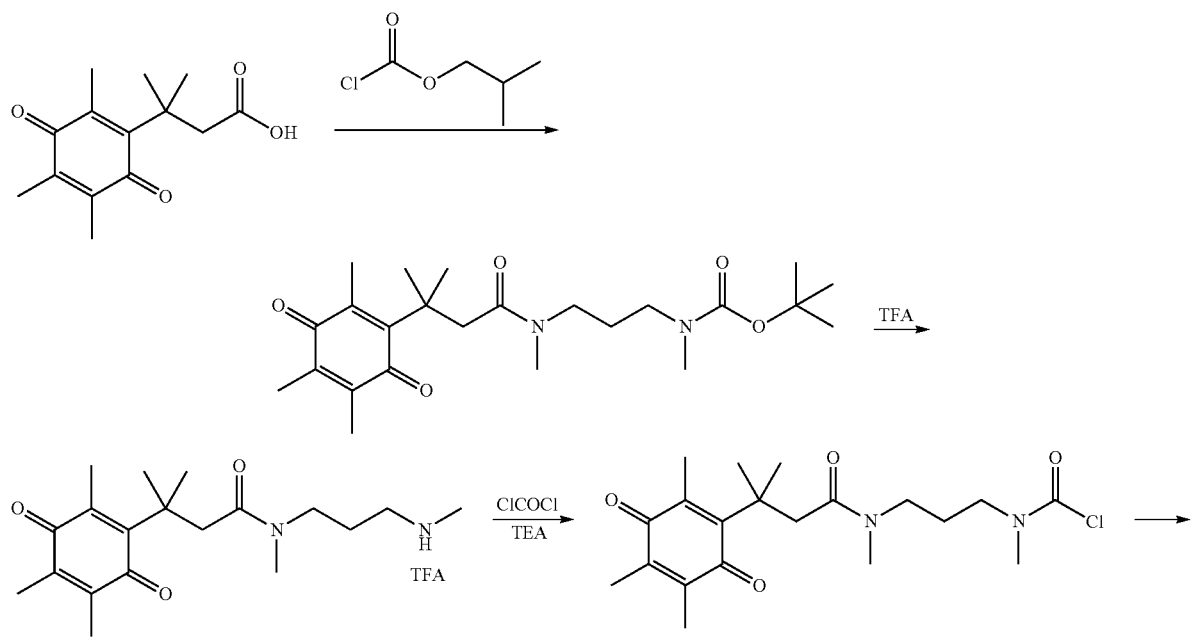

-continued

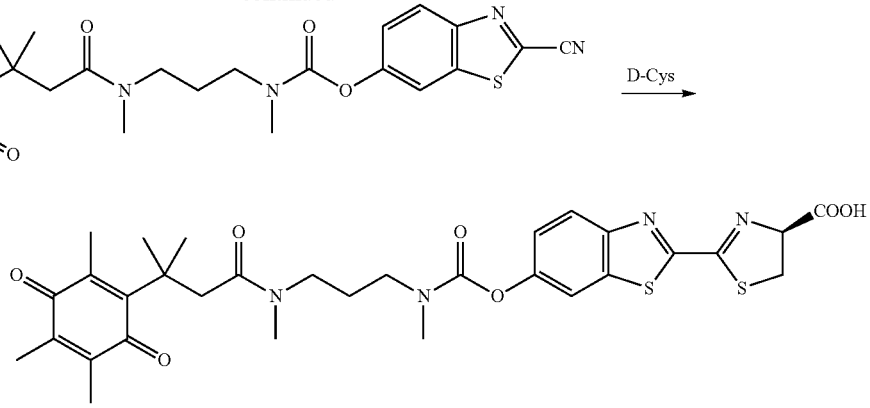

PBI 4308

Quinone-trimethyllock-C3-diamine-Boc

To a solution of 3-methyl-3-(2,4,5-trimethyl-3,6-dioxocyclohexa-1,4-dien-1-yl)butanoic acid (1.5 g, 5.99 mmol) and isobutyl chloroformate (0.90 g, 6.59 mmol) in 30 ml of dry THF, N-methyl morpholine (0.67 g, 6.59 mmol) was added at 0° C. The resultant mixture was stirred 30 minutes at 0° C., mono BOC—N,N'-dimethyl propanediamine (1.45 g, 7.19 mmol) added, and the resultant mixture stirred at room temperature overnight. The compound was directly purified by silica chromatography using heptane and ethyl acetate as eluent to give a yield of 91%. $^1$H NMR (300 MHz, CD$_2$Cl$_2$) δ 3-3.3 (m, 4H, NCH2), 2.95 (m, 3H, NCH3), 2.80 (m, 3H, NCH3), 2.10 (s, 2H, CH2), 1.8-2.0 (m, 3H, Ch3), 1.35-1.5 (m, 15H). MS (m/e): 355 (M$^+$-Boc).

Quinone-trimethyllock-C3-diamine TFA salt

To a solution of quinone-trimethyllock-C3-diamine-Boc (1.0 g, 2.30 mmol) in 10 ml of methylene dichloride, triisopropylsilane (0.1 ml) followed by 10 ml of TFA was added. The mixture was stirred for 2 hours at room temperature. After removal of the solvent, the product was dried under a vacuum and used directly in next step without purification.

Quinone-trimethyllock-C3-diamine carbonyl chloride

To a solution of quinone-trimethyllock-C3-diamine TFA salt (0.33 g, 0.74 mmol) in 20 ml of dry methylene chloride, phosgene solution in toluene (20%, 9.1 g) was added. TEA (0.148 g, 1.48 mmol) was then added dropwise at 0° C. (more TEA is needed if the solution is too acidic). The mixture was stirred for 30 minutes at 0° C., and TLC performed to verify that no starting material remained. The solid was carefully removed by filtration using butylamine as the phosgene trapping reagent in a vacuum trap. The residue was purified by silica chromatography using heptane and ethyl acetate as eluent to give a yield of 0.292 g (100%).

Quinone-trimethyllock-C3-diamine 2-cyanobenzothiazole carbamate

To a solution of quinone-trimethyllock-C3-diamine carbonyl chloride (0.292 g, 0.736 mmol) in 10 ml of dry methylene chloride, 2-cyano-6-hydroxybenzothiazole (0.194 g, 1.10 mmol), TEA (0.112 g, 1.1 mmol) and DMAP (0.134 g, 1.1 mmol) was added. The resultant mixture was stirred overnight. The compound was directly purified by silica chromatography using heptane/ethyl acetate as eluent to give a yield of 0.233 g (59%). The compound might exist as two rotomers (7:3). $^1$H NMR (300 MHz, CD$_2$Cl$_2$) δ 8.15-8.26 (d1d2 (3:7), J=9.0, 1H), 7.85 (d1d2 (3:7), J=3.0, 1H), 7.4-7.5 (dd1,dd2 (3:7), J=9, J=3, 1H), 3.25-3.50 (m, 4H, 2NCH2), 2.7-3.2 (m, 8H, 2NCH3+COCH2), 2.11 (s, 3H, CH3), 1.6-1.9 (m, 8H, 2CH3+CH$_2$), 1.42 (s, 6H, CH3). MS (m/e): 537 (M$^+$).

Quinone trimethyllock-C3-carbamate luciferin (PBI 4308)

To a solution of quinone-trimethyllock-C3-diamine 2-cyanobenzothiazole carbamate (0.177 g, 0.317 mmol) in 20 ml of CH$_2$Cl$_2$/MeOH, D-cysteine (0.144 g, 0.819 mmol) and TEA (0.164 g, 1.63 mmol) in 5 ml of water was added. The mixture was stirred for 10 minutes and then acidified to pH 6 with acetic acid. After removal of methylene chloride, the compound was purified by HPLC using 0.1% formic acid and acetonitrile as eluents. The compound might exist as two rotomers (7:3). $^1$H NMR (300 MHz, CD$_2$Cl$_2$) δ 8.11 (dd (7:3), J=9.0, 1H), 7.85 (dd (7:3), J=3.0, 1H), 7.38 (m, 1H), 5.45 (t, J=9, 1 H, CH), 3.81 (d, J=9, 2H, SCH2), 3.42 (t, J=6, 2H, NCH2), 3.25-3.50 (m, 4H, 2NCH2), 2.7-3.2 (m, 8H, 2NCH3+COCH2), 2.11 (ss (7:3), 3H, CH3), 1.7-1.9 (m, 8H, 2CH3+CH$_2$), 1.42 (s, 6H, CH3). MS (m/e): 641 (M$^+$). HPLC purity on C18 column: 98.5% at 330 nm; isomer ratio on chiral column (31%:69%).

Example 6

Synthesis of PBI 4586

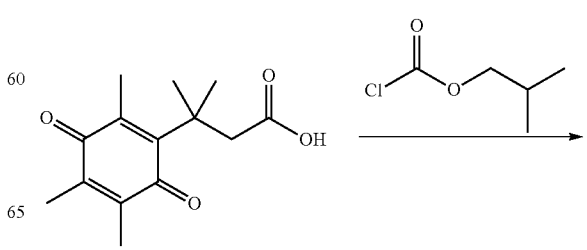

-continued

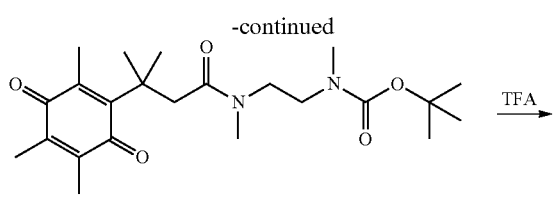

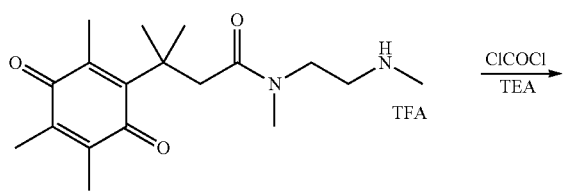

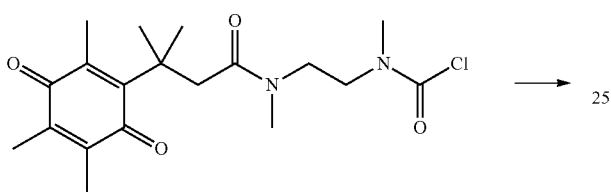

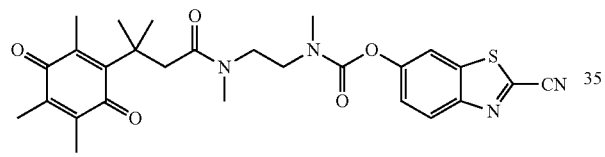

PBI 4586

PBI 4586 was prepared by employing the similar procedures for the synthesis of PBI 4308 (Example 5).

Quinone-trimethyllock-C2-diamine-Boc $^1$H NMR (300 MHz, CD$_2$Cl$_2$) δ 3-3.3 (m, 4H, NCH2), 2.7-3.1 (m, 8H, 2×NCH3+CH$_2$), 2.10 (s, 3H, CH3), 1.8-2.0 (m, 6H, CH3), 1.3-1.5 (m, 15H, 2×CH3+3CH3). MS (m/e): 421 (M+), 321 (M$^+$-Boc).

Quinone-trimethyllock-C2-diamine carbonyl chloride $^1$H NMR (300 MHz, CD$_2$Cl$_2$) δ 3.4-3.6 (m, 4H, NCH2), 2.7-3.2 (m, 8H, 2×NCH3+CH$_2$), 2.12 (s, 3H, CH3), 1.94 (s, 3H, CH3), 1.90 (s, 3H, CH3), 1.3-1.5 (m, 6H, 2×CH$_3$). MS (m/e): 383, 385 (M+, 3:1).

Quinone-trimethyllock-C2-diamine 2-cyanobenzothiazole carbamate (PBI 4586)

$^1$H NMR (300 MHz, CD$_2$Cl$_2$) δ 8.15-8.26 (d, 1H), 7.86 (s, 1H), 7.4-7.5 (m, 1H), 3.3-3.7 (m, 4H, 2NCH2), 2.7-3.2 (m, 8H, 2NCH3+COCH2), 1.7-2.2 (m, 9H, 3CH3), 1.3-1.5 (m, 6H, CH3). MS (m/e): 523 (M$^+$).

Example 7

Synthesis of PBI 4312

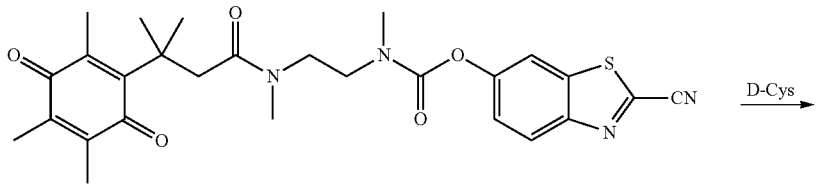

PBI 4586

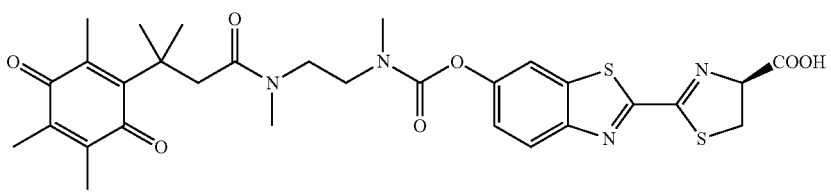

PBI 4312

PBI 4312 was prepared by cyclization of PBI 4586 (Example 6) and D-cysteine using the similar method described for the synthesis of PBI 4308 (Example 5). $^1$H NMR (300 MHz, CD$_2$Cl$_2$) δ 8.0-8.2 (m, 1H), 7.7-7.9 (m, 1H), 7.3-7.5 (m, 1H), 5.42 (t, J=9, 1H, CH), 4.18 (d, J=9, 2 H, SCH2), 3.3-3.7 (m, 4H, 2NCH2), 2.7-3.2 (m, 8H, 2NCH3+COCH2), 1.7-2.2 (m, 9H, 3CH3), 1.3-1.5 (m, 6H, CH3). MS (m/e): 627 (MH$^+$).

HPLC purity on C18-column: 97.7% at 330 nm; isomer ratio on chiral column: 15.3%:84.7%.

Example 8

Synthesis of PBI 4585

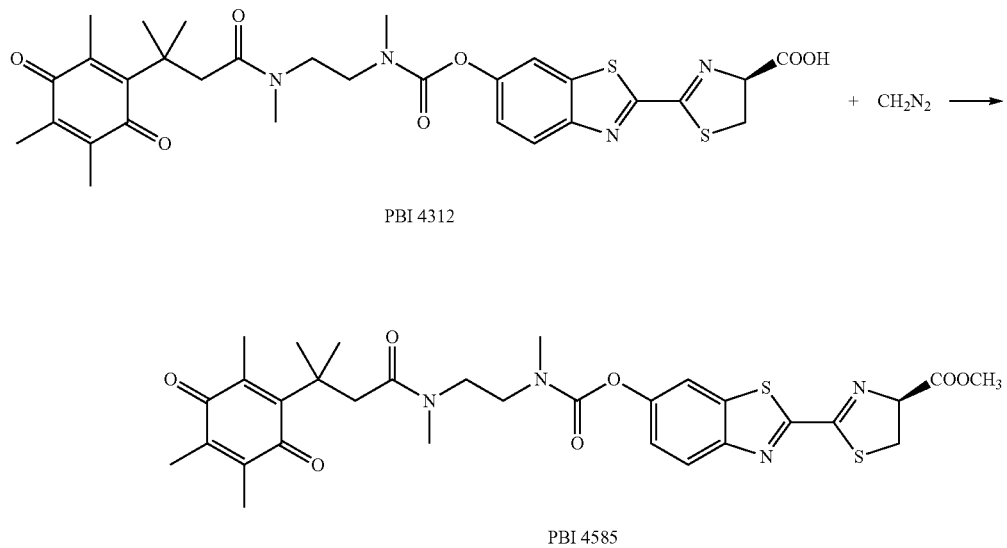

To a mixture of KOH (40%, 6 ml) and ether (40 ml), N-methyl-N-urea (4.0 g, 0.0194 mmol) was added at 0° C. The mixture was stirred at 0° C. until the white solid disappeared. The ether layer was decanted to another flask and dried over KOH at 0° C. The ether solution (~10 ml) was then added to quinone trimethyllock-C2-diamine luciferin (PBI 4312) (0.20 g, 0.311 mmol) in 15 ml of THF and stopped once the starting material was completely consumed as verified by TLC. The reaction was quenched by adding acetic acid. The compound was purified by silica chromatography using heptane and ethyl acetate as eluents to give a yield of 84% (0.17 g). $^1$H NMR (300 MHz, CD$_2$Cl$_2$) δ 8.10 (d, 1H), 7.77 (s, 1H), 7.33 (d, 1H), 5.37 (t, J=9, 1H, CH), 3.84 (s, 3H, OCH3), 3.76 (t, J=9, 2 H, SCH2), 3.4-3.6 (m, 4H, 2NCH2), 2.7-3.2 (m, 8H, 2NCH3+COCH2), 1.7-2.2 (m, 9H, CH3), 1.3-1.5 (m, 6H, CH3). MS (m/e): 641 (MH$^+$), 663 (MNa+). HPLC purity: 88.4% at 330 nm

Example 9

Synthesis of PBI 4516

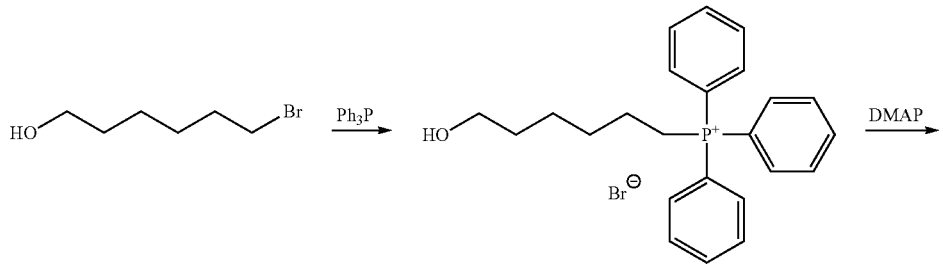

-continued

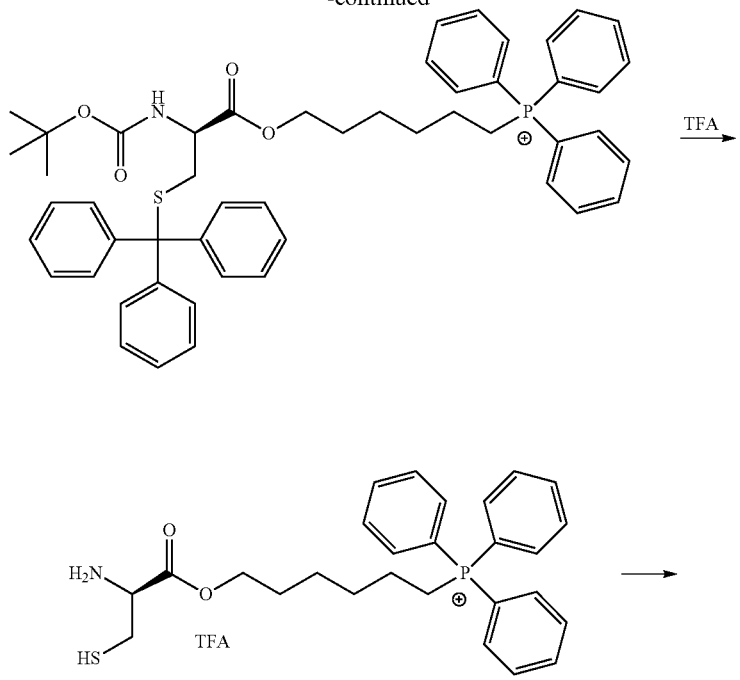

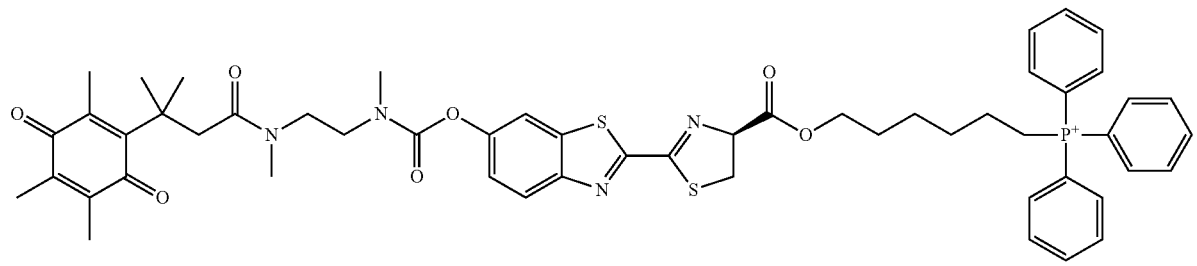

PBI 4516

(6-hydroxyhexyl)triphenylphosphonium bromide

A mixture of 6-hydroxyhexyl bromide (10.36 g, 0.057 mol) and triphenylphosphine (5 g, 0.019 mol) in 100 ml of acetonitrile was refluxed for 2 days. After removal of the solvent, the residue was washed three times with ether. The solid was purified by silica chromatography using heptane/ethyl acetate and methylene chloride/MeOH as eluent to give viscous pale white material.

(S)-(6-((2-((tert-butoxycarbonyl)amino)-3-(tritylthio) propanoyl)oxy)-hexyl)triphenyl phosphonium To a solution of Boc-Trityl-D-cys (1.67 g, 3.61 mmol), DCC (2.98 g, 14.44 mmol), DMAP (0.881 g, 7.22 mmol) and (6-hydroxyhexyl)-triphenylphosphonium bromide (1.60 g, 3.61 mmol) were added at 0° C. The mixture was stirred overnight at room temperature. After removal insoluble solid, the compound was purified by silica chromatography using methylene chloride/MeOH as an eluent to give a yield of 93% (2.78 g). $^1$H NMR (300 MHz, $CD_2Cl_2$) δ 8.17 (dd, J=1.6, 5.0, 2H), 7.93-7.64 (m, 13H), 7.46-7.15 (m, 13H), 6.51 (dd, J=1.6, 5.0, 2H), 5.33 (m, 1H), 4.06 (td, J=3.0, 6.5, 2H, OCH2), 3.57 (m, 2H, SCH2), 2.55 (d, J=5.1, 2H, PGH2), 1.5-2.0 (m, 8H, CH2), 1.40 (s, 9H, CH3). MS (m/e): 808 (M$^+$).

(S)-(6-((2-amino-3-mercaptopropanoyl)oxy)hexyl) triphenylphosphonium

To a solution of (S)-(6-((2-((tert-butoxycarbonyl)amino)-3-(tritylthio)propanoyl)oxy)hexyl)-triphenyl phosphonium (0.315 g, 0.68 mmol) in 10 ml of methylene dichloride, triisopropylsilane (0.1 ml) followed by 10 ml of TFA was added. The mixture was stirred for 2 hours at room temperature. After removal of solvent under high vacuum, the product was directly used in next step without further purification.

Quinone-trimethyllock-C2-diamine-luciferin-C6-triphenylphosphonium (PBI 4516)

The above residue was dissolved in DMF. Quinone-trimethyllock-C2-diamine 2-cyanobenzothiazole carbamate (PBI 4586) (0.10 g, 0.191 mmol) was added, and the pH of the solution adjusted to pH 8 with TEA. The resultant mixture was stirred at room temperature for 30 minutes. The compound was directly purified with HPLC using formic acid (0.1%)/acetonitrile as an eluent. MS (m/e): 971 (M$^+$).

Example 10

Synthesis of PBI 4550

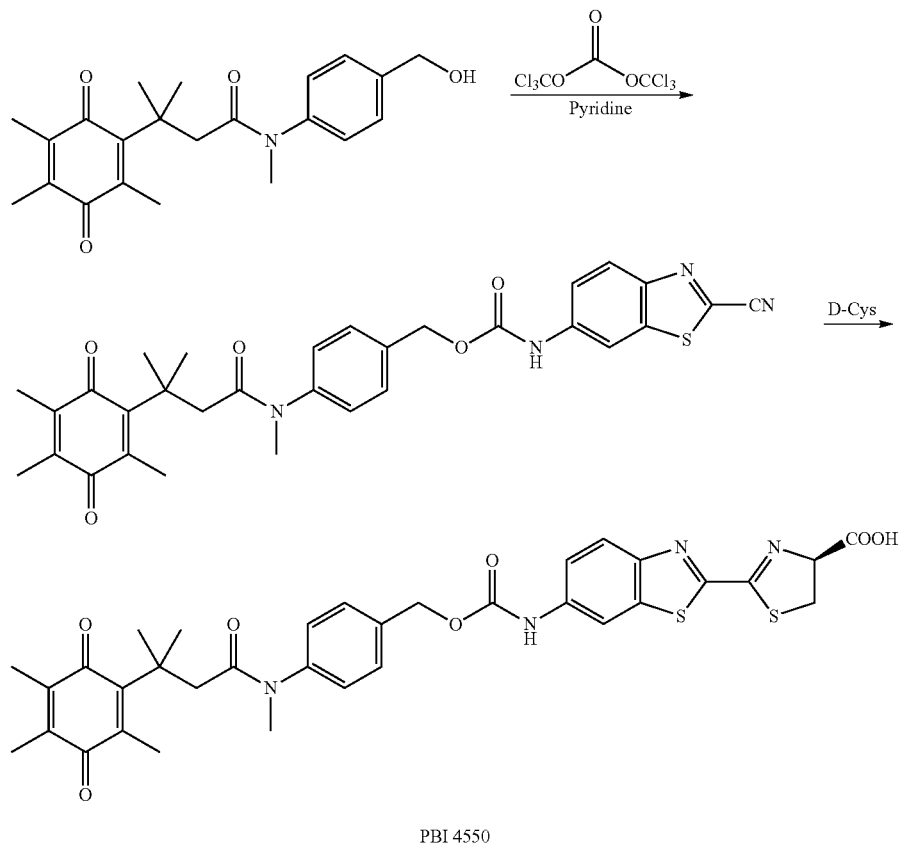

PBI 4550

Quinone-trimethyllock-N-methyl-benzylalcohol 2-cyano-6-aminobenzothiazole carbamate To a solution of quinone-trimethyllock-N-methylbenzylalcohol (0.53 g, 1.43 mmol) and triphosgene (0.153 g, 0.516 mmol) in 10 ml of methylene, pyridine (0.17 g, 2.15 mmol) was added at 0° C., and the mixture stirred for 30 minutes at 0° C. 2-cyano-6-aminobenzothiazole (0.377 g, 2.15 mmol) and TEA (0.3 ml) were added, and the resultant mixture was stirred overnight at room temperature. After removal of insoluble solid by filtration, the compound was directly purified with silica chromatography using heptane and ethyl acetate as eluents to give a yield of 22% (0.18 g). $^1$H NMR (300 MHz, CD$_2$Cl$_2$) δ 8.45 (d, J=2.3, 1H), 8.13 (d, J=8.9, 1H), 7.50 (d, J=8.0, 2H), 7.45 (dd, J=8.9, 2.7, 2H), 7.24 (d, J=7.9, 2H), 5.29 (s, 2H, OCH2), 3.97 (s, 3H, NCH3), 2.74 (s, 2H, CH2), 2.09 (s, 3H, CH3), 1.98 (s, 3H, CH3), 1.95 (s, 3H, CH3), 1.30 (s, br, 6H). MS (m/e): 571 (MH$^+$).

Quinone trimethyllock-N-methyl-luciferin carbamate (PBI 4550)

To a solution of quinone-trimethyllock-N-methyl-benzylalcohol 2-cyano-6-aminobenzothiazole carbamate (0.10 g, 0.175 mmol) in 20 ml of CH$_2$Cl$_2$/MeOH, D-cysteine (0.046 g, 0.262 mmol) and TEA (0.053 g, 0.52 mmol) in 3 ml of water was added. The mixture was stirred for 10 minutes, and then acidified to pH 6 with acetic acid. After removal of methylene chloride, the compound was purified by HPLC using 0.1% formic acid and acetonitrile as eluents. $^1$H NMR (300 MHz, CD$_2$Cl$_2$) δ 8.35 (d, J=2.2, 1H), 8.25 (s, 1H, NH), 8.01 (d, J=8.9, 1H), 7.5-7.7 (m, 3H), 7.29 (d, J=7.9, 2H), 5.41 (t, J=9, 1H, CH), 5.27 (s, 2H, OCH2), 3.77 (d, J=9, 2H, SCH2), 3.12 (s, br, 3H, NCH3), 2.72 (s, br, 2H, CH2), 2.07 (s, 3H, CH3), 1.96 (s, 3H, CH3), 1.94 (s, 3H, CH3), 1.30 (s, br, 6H). MS (m/e): 675 (M$^+$). HPLC purity: 96.6% at 330 nm.

Example 11

Synthesis of PBI 4565

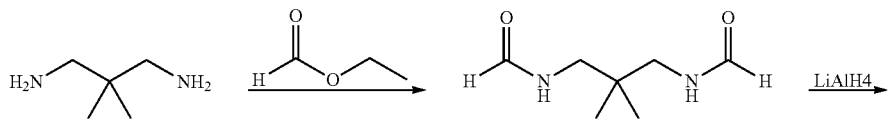

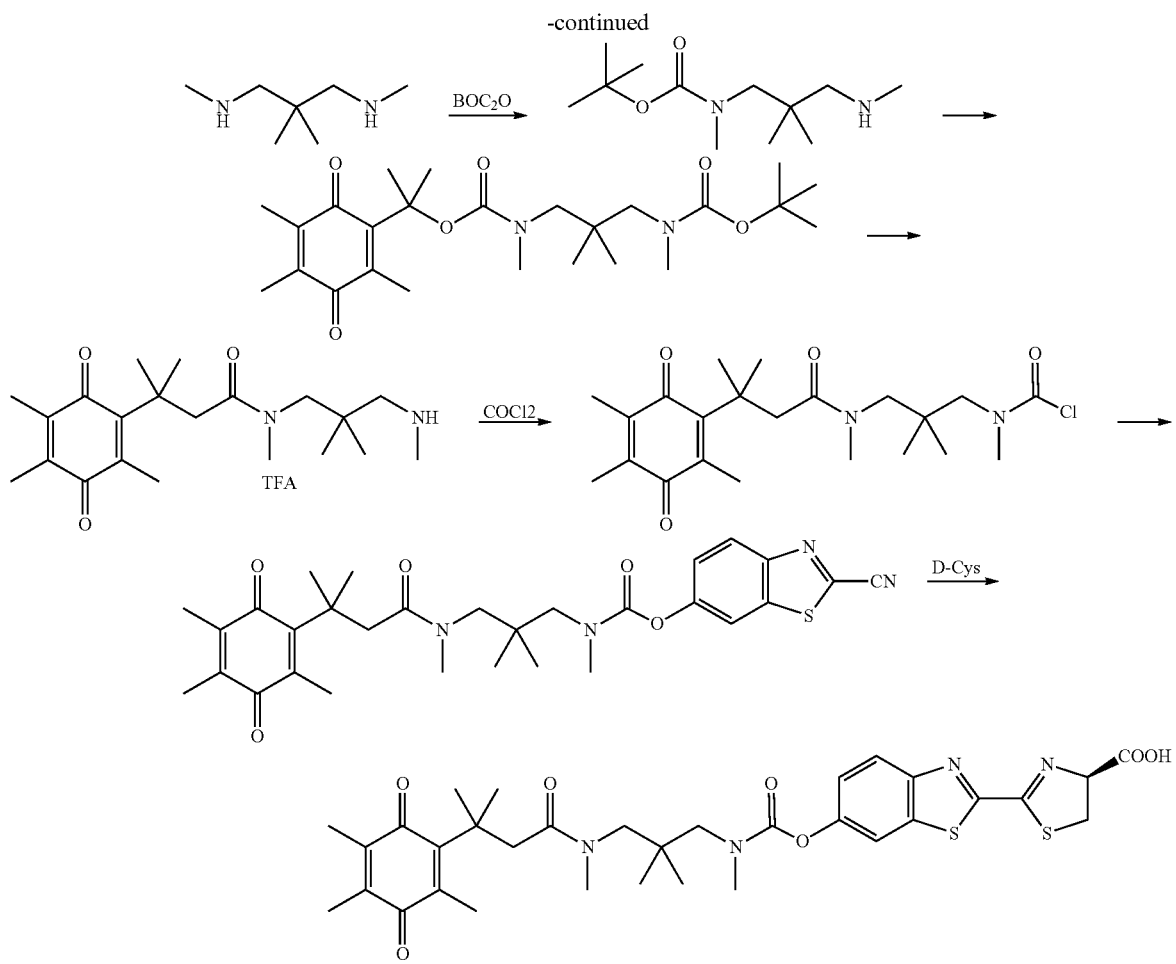

PBI 4565

N,N'-diformyl-2,2-dimethylpropane-1,3-diaminne

A mixture of 2,2-dimethylpropanyl diamine (25 g, 0.245 mmol) in 200 ml of ethyl formate was heated to reflux over two days. After removal of solvent under a vacuum, the compound was purified by silica chromatography using heptane/ethyl acetate as eluent to give a yield 50% (19 g). $^1$H NMR (300 MHz, $CD_2Cl_2$) δ 8.20 (s, 1H), 6.68 (s, br, 1H, NH), 3.05 (d, J=6, 4H, CH2), 0.9 (s, 6H, CH3). MS (m/e): 159 ($M^+$).

N,N',2,2-tetramethylpropane-1,3-diamine

To a mixture of 250 mL of ether and 10 g of $LiAlH_4$ (95%) at 0° C., 9.88 g (62.5 mmol) N,N'-diformyl-2,2-dimethylpropane-1,3-diamine was added in small portions. After the addition, the reaction mixture was stirred at room temperature for 20 h. The mixture was then hydrolyzed with ether and water, the white solid removed by filtration through Celite, and the filtrate dried over anhydrous $Na_2SO_4$. After removal of the solvent, the product was obtained as a colorless oil. MS (m/e): 131 ($M^+$).

Mono-Boc-N,N',2,2-tetramethylpropane-1,3-diamine

To a solution of N,N',2,2-tetramethylpropane-1,3-diamine (1.32 g, 10.14 mmol) and TEA (2.83 ml) in 30 ml of methylene chloride, a solution of Boc-anhydride (1.10 g, 5.04 mmol) was added at 0° C., and the resulting mixture stirred overnight at room temperature. The solution was washed with water and dried over anhydrous sodium sulfate. After removal of the solvent, the compound was used in the next step without further purification.

Quinone trimethyllock Boc-N,N',2,2-tetramethylpropane-1,3-diamine

To a solution of 3-methyl-3-(2,4,5-trimethyl-3,6-dioxocyclohexa-1,4-dien-1-yl)butanoic acid (1.09 g, 4.34 mmol) and isobutyl chloroformate (0.592 g, 4.34 mmol) in 30 ml of dry THF, N-methyl morphorline (0.44 g, 4.34 mmol) was added at 0° C. The resultant mixture was stirred for 30 minutes at 0° C., mono Boc-N,N',2,2-tetramethyl propanediamine (1.0 g, 4.34 mmol) added, and the resultant mixture stirred at room temperature overnight. The compound was directly purified by silica chromatography using heptane and ethyl acetate as eluents to give a yield of 52% (1.02 g). MS (m/e): 463 ($M^+$).

Quinone trimethyllock N,N',2,2-tetramethylpropane-1,3-diamine TFA salt

To a solution of quinone trimethyllock Boc-N,N',2,2-tetramethylpropane-1,3-diamine (0.87 g, 1.88 mmol) in 10 ml of methylene dichloride, triisopropylsilane (0.1 ml) followed by 10 ml of TFA was added. The mixture was stirred for 2 hours at room temperature. After removal of the solvent, the product was directly used in next step without purification. MS (m/e): 463 (M+).

Quinone trimethyllock N,N',2,2-tetramethylpropane-1,3-diamine carbonyl chloride To a solution of quinone-trimethyllock N,N',2,2-tetramethylpropane diamine TFA salt (0.894 g, 1.88 mmol) in methylene chloride (20 ml), a phosgene solution in toluene (20%, 14 g) was added followed by dropwise addition of TEA (0.57 g, 5.64 mmol) at 0° C. (more TEA is needed if the solution is too acidic). The mixture was stirred for 30 minutes, and TLC performed to verify that no starting material remained. The solid was carefully removed by filtration using butylamine as a phosgene trapping reagent in a vacuum trap. The residue was purified by silica chromatography using heptane and ethyl acetate as eluents to give a yield of 0.422 g (53%).

Quinone trimethyllock N,N,2,2-tetramethylpropanediamine-2-cyanobenzothiazole carbamate To a solution of quinone-trimethyllock N,N',2,2-tetramethylpropane diamine carbonyl chloride (0.42 g, 0.988 mmol) in 10 ml of dry methylene chloride, 2-cyano-6-hydroxybenzothiazole (0.26 g, 1.48 mmol), TEA (0.206 ml) and DMAP (0.18 g, 1.47 mmol) was added. The resultant mixture was stirred overnight. The compound was directly purified by silica chromatography using heptane/ethyl acetate as an eluent to give a yield of 0.177 g (32%). $^1$H NMR (300 MHz, CD$_2$Cl$_2$) δ 8.19 (d, J=8.7, 1H), 7.87-7.75 (m, 1H), 7.42 (d, J=9.0, 1H), 3.37-2.97 (m, 12H, 2NCH3+2NCH2+CH$_2$), 1.7-2.2 (m, 9H, 3CH3), 1.41 (s, 3H, CH3), 1.42 (s. 3H, CH3), 1.14 (s, 3H, CH3), 1.09 (s, 3H, CH3). MS (m/e): 565 (M$^+$), 587 (MNa+).

Quinone trimethyllock-N,N',2,2-tetramethylpropanediamine carbamate luciferin (PBI 4565)

To a solution of quinone trimethyllock N,N,2,2-tetramethylpropanediamine 2-cyanobenzothiazole carbamate (0.020 g, 0.046 mmol) in 5 ml of MeOH, D-cysteine (0.016 g, 0.092 mmol) and TEA (0.018 g, 0.184 mmol) in 2 ml of water was added. The mixture was stirred for 10 minutes, and then acidified to pH 6 with acetic acid. The compound was purified by HPLC using 0.1% of formic acid and acetonitrile as eluent. $^1$H NMR (300 MHz, CD$_2$Cl$_2$) δ 8.02 (dd, J=6.0, 8.9, 1H), 7.70 (s, 1H), 7.26 (dd, J=2.3, 8.9, 1H), 5.31 (t, J=9.6, 1H, CH), 3.70 (d, J=11.9, 2H, SCH2), 3.1-3.4 (m, 6H, 2NCH2+CH2), 3.06 (s, 3H, CH3), 3.03 (s, 3H, CH3), 1.82-2.2 (m, 9H, CH3), 1.42 (s, 3H, CH3), 1.41 (s, 3H, CH3), 1.01 (s, 3H, CH3), 0.96 (s, 3H, CH3). MS (m/e): 669 (MH$^+$). HPLC purity: 98.5% at 330 nm.

Example 12

Synthesis of PBI 4384

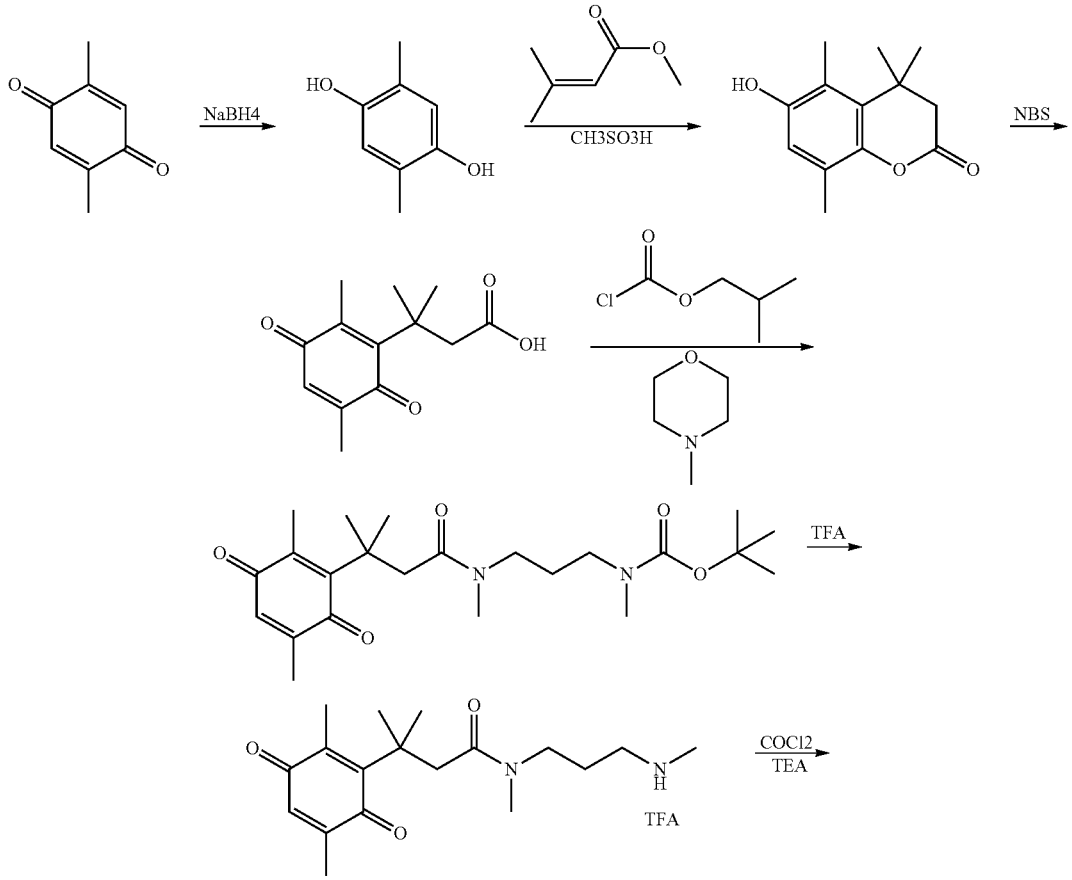

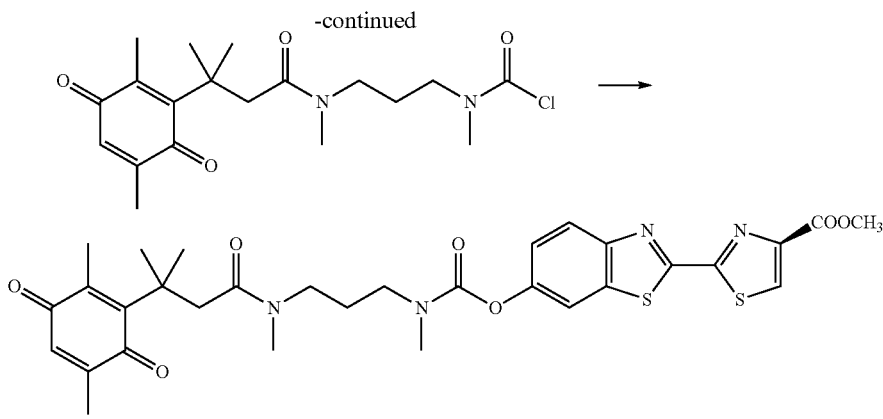

PBI 4384

2,5-dimethyl-1,4-bisphenol

To a solution of 2,5-dimethyl cyclohexa-2,5-diene-1,4-dione (10 g, 73.45 mmol) in ether/water (400 ml/200 ml), NaBH$_4$ (11.12 g, 0.293 mol) was added at 0° C. The mixture was shaken until the yellow color disappeared. The mixture was then acidified with acetic acid, extracted three times with ether, and the combined organic layers dried over Na$_2$SO$_4$. After removal of the solvent, the compound was directly used in the next step.

2,5-dimethylcyclohexa-2,5-diene-1,4-dione

To the above crude 2,5-dimethyl bisphenol methyl methacrylate (8.38 g, 73.45 mmol) and methanesulfonic acid (100 ml) was added. The mixture was heated up to 90° C. for 2 hours. Upon cooling to room temperature, the mixture was poured into ice-cold water and extracted three times with ethyl acetate, and the combined organic layers were dried over Na$_2$SO$_4$ and purified by silica chromatography using ethyl acetate and heptane as eluents. $^1$H NMR (300 MHz, CD$_2$Cl$_2$) δ 4.84 (s, 1H), 2.55 (s, 2H, CH$_2$), 2.32 (s, 3H, CH3), 2.21 (s, 3H, CH3), 1.46 (s, 6H, CH3). MS (m/e): 221 (M+).

The following two compounds were made by the similar procedures described in Example 5.

3-(2,5-dimethyl-3,6-dioxocyclohexa-1,4-dien-1-yl)-3-methylbutanoic acid $^1$H NMR (300 MHz, CD$_2$Cl$_2$) δ 6.7-7.1 (m, 1H), 2.58 (s, 2H, CH2), 2.47 (s, 3H, CH3), 2.25 (s, 3H, CH3), 1.44 (s, 6H, CH3). MS (m/e): 235 (M).

(3-(3-(2,5-dimethyl-3,6-dioxocyclohexa-1,4-dien-1-yl)-N,3-dimethylbutanamido) propyl)(methyl)carbamic chloride (Yield: 83%). $^1$H NMR (300 MHz, CD$_2$Cl$_2$) δ 6.37 (s, 1H), 3.22-3.38 (m, 4H, NCH2), 2.7-3.2 (m, 8H, NCH3+CH$_2$), 1.8-2.2 (m, 6H, 2CH3), 1.7-1.9 (m, 2H, CH$_2$), 1.42 (s, 9H, CH3). MS (m/e): 383 (M+)

Quinone trimethyllock dehydroluciferin methyl ester (PBI 4384)

To a solution of quinone-trimethyllock-C3-diamine carbonyl chloride (0.44 g, 1.15 mmol) in 15 ml of dry methylene chloride luciferin methyl ester (0.37 g, 1.26 mmol), TEA (0.127 g, 1.26 mmol) and DMAP (0.18 g, 1.47 mmol) was added. The resultant mixture was stirred overnight. The compound was purified by silica chromatography using heptane/ethyl acetate as an eluent. $^1$H NMR (300 MHz, CD$_2$Cl$_2$) δ 8.35 (s, 1H), 8.01-8.15 (m, 1H), 7.7-7.9 (m, 1H), 7.3-7.4 (m, 1H), 6.37 (s, 1H), 3.97n (s, 3H, OCH3), 3.25-3.5 (m, 4H, NCH2), 2.7-3.25 (m, 8H, NCH3+CH$_2$), 1.8-2.2 (m, 6H, 2CH3), 1.7-1.9 (m, 2H, CH2), 1.42 (s, 9H, CH3). MS (m/e): 639 (M+). (NMR and MS confirmed the product was dehydroluciferin).

Example 13

Synthesis of PBI 4412

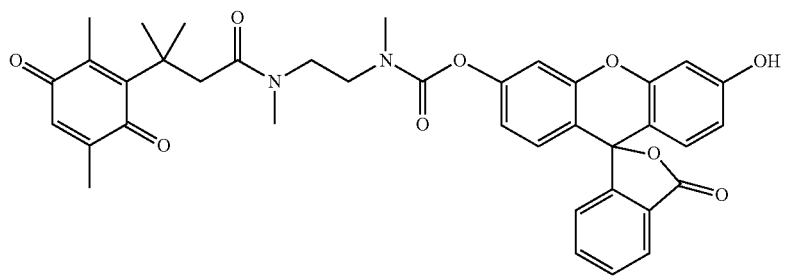

PBI 4412

Mono-quinone trimethyllock diamine fluorescein (PBI 4412) was made from 3-(3-(2,5-dimethyl-3,6-dioxocyclohexa-1,4-dien-1-yl)-N,3-dimethylbutanamido) propyl) carbonyl chloride and fluorescein by employing the similar procedure described in Example 5. $^1$H NMR (300 MHz, CD$_2$Cl$_2$) δ 8.02 (d, J=6.9, 1H), 7.95 (s, 1H), 7.83-7.65 (m, 2H), 7.33-7.07 (m, 2H), 6.94-6.52 (m, 5H), 6.35 (s, 1H), 3.3-3.7 (m, 4H, NCH2), 3.1-2.7 (m, 8H), 2.2-1.7 (m, 6H, CH3), 1.46-1.33 (m, 6H). MS (m/e): 665 (M+).

Example 14

Synthesis of PBI 4413

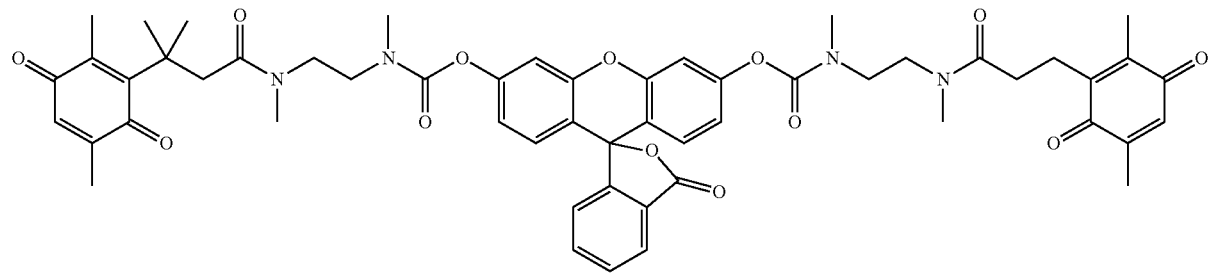

PBI 4413

Bis-quinone trimethyllock diamine fluorescein (PBI 4413) was isolated from the reaction of 3-(3-(2,5-dimethyl-3,6-dioxocyclohexa-1,4-dien-1-yl)-N,3-dimethylbutanamido) propyl) carbonyl chloride used in making PBI 4412 (Example 13). $^1$H NMR (300 MHz, CD$_2$Cl$_2$) δ 8.02 (d, J=6.9, 1H), 7.95 (s, 1H), 7.83-7.65 (m, 2H), 7.4-7.1 (m, 3H), 7.0-6.6 (m, 4H), 6.35 (s, 1H), 3.2-3.7 (m, 8H, NCH2), 3.1-2.7 (m, 16H), 2.2-1.7 (m, 12H, CH3), 1.46-1.33 (m, 12H). MS (m/e): 997.6 (M+).

Example 15

Synthesis of PBI 4440

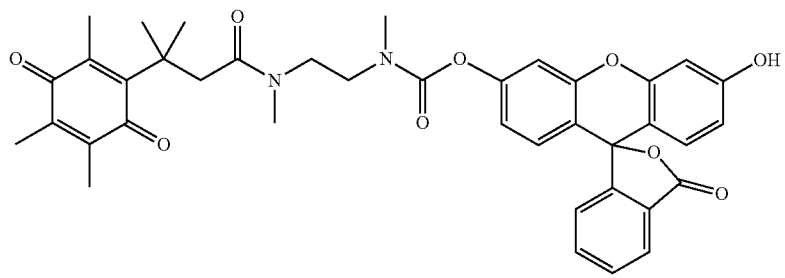

PBI 4440

Mono-quinone trimethyllock diamine fluorescein (PBI 4440) was made from quinone-trimethyllock-C2-diamine carbonyl chloride and fluorescein by employing the similar method described in Example 5. $^1$H NMR (300 MHz, CD$_2$Cl$_2$) δ 7.89 (d, J=6.9, 1H), 7.3-7.6 (m, 3H), 7.0-7.4 (m, 2H), 6.6-6.8 (m, 3H), 6.3-6.6 (m, 3H), 3.2-3.6 (m, 4H, NCH2), 3.2-2.7 (m, 8H), 2.2-1.6 (m, 9H, CH3), 1.45-1.30 (m, 6H, CH3). MS (m/e): 679.4 (M+).

Example 16

Synthesis of PBI 4441

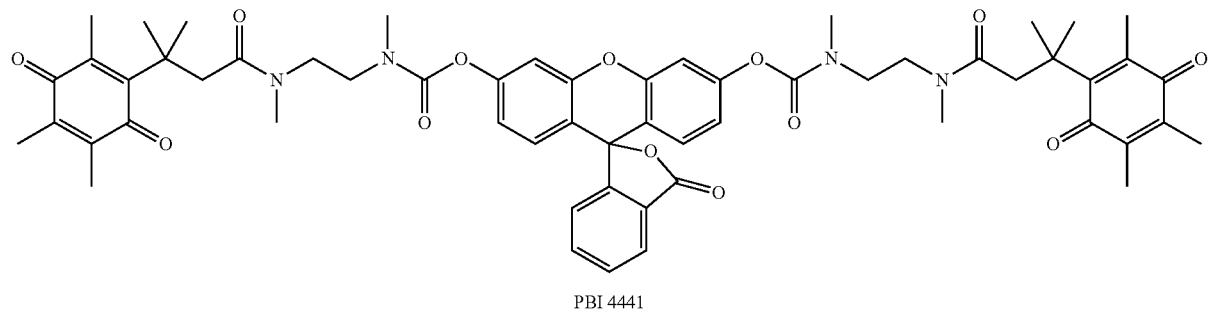 [SMILES: CC1=C(C)C(=O)C(C(C)(C)CC(=O)N(C)CCN(C)C(=O)Oc2ccc3c(c2)Oc2cc(OC(=O)N(C)CCN(C)C(=O)CC(C)(C)C4=C(C)C(=O)C(C)=C(C)C4=O)ccc2C32OC(=O)c3ccccc32)=C(C)C1=O]

PBI 4441

Bis-quinone trimethyllock diamine fluorescein (PBI 4441) was isolated from the reaction of quinone-trimethyllock-C2-diamine carbonyl chloride and fluorescein for making PBI 4440 (Example 15). $^1$H NMR (300 MHz, $CD_2Cl_2$) δ 8.02 (d, J=6.9, 1H), 7.83-7.65 (m, 2H), 7.4-7.1 (m, 3H), 7.0-6.6 (m, 4H), 6.35 (s, 1H), 3.2-3.7 (m, 8H, NCH2), 3.1-2.7 (m, 16H), 2.2-1.7 (m, 18H, CH3), 1.46-1.33 (m, 12H). MS (m/e): 1025.7 (M+).

Example 17

Synthesis of PBI 4552

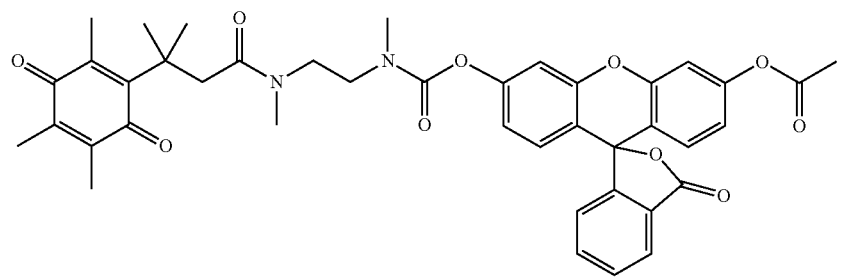

PBI 4552

Mono-quinone trimethyllock diamine fluorescein acetyl ester (PBI 4552) was made from quinone-trimethyllock-C2-diamine carbonyl chloride and fluorescein acetyl ester by employing the similar method described in Example 5. $^1$H NMR (300 MHz, $CD_2Cl_2$) δ 7.89 (d, J=6.9, 1H), 7.52-7.80 (m, 2H), 7.1-7.3 (m, 3H), 6.7-7.0 (m, 5H), 3.3-3.7 (m, 4H, NCH2), 3.2-2.7 (m, 8H), 2.31 (s, 3H, COCH3), 2.2-1.6 (m, 9H, CH3), 1.48-1.30 (m, 6H, CH3). MS (m/e):721.4 (M+).

Example 18

Synthesis of PBI 4543

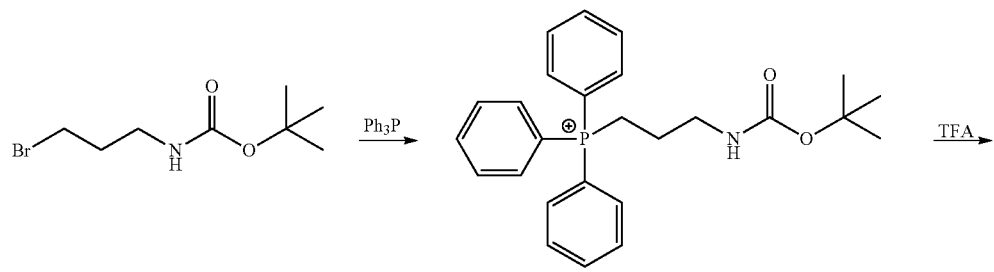

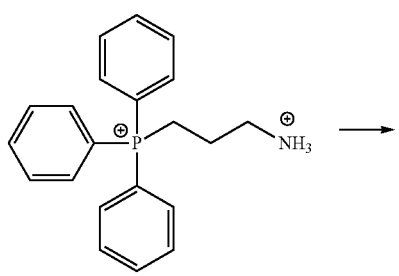

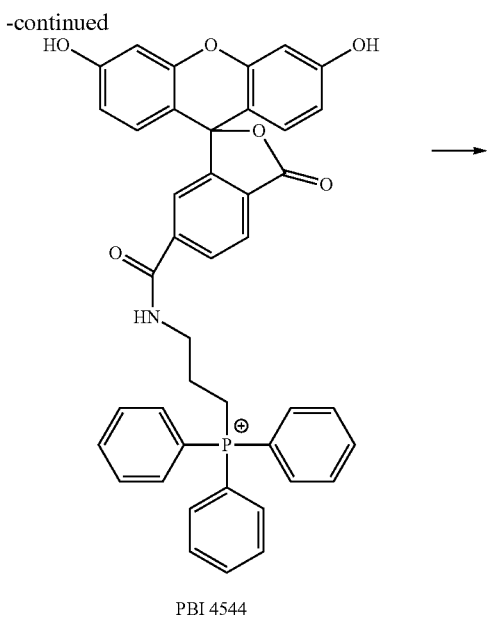

PBI 4544

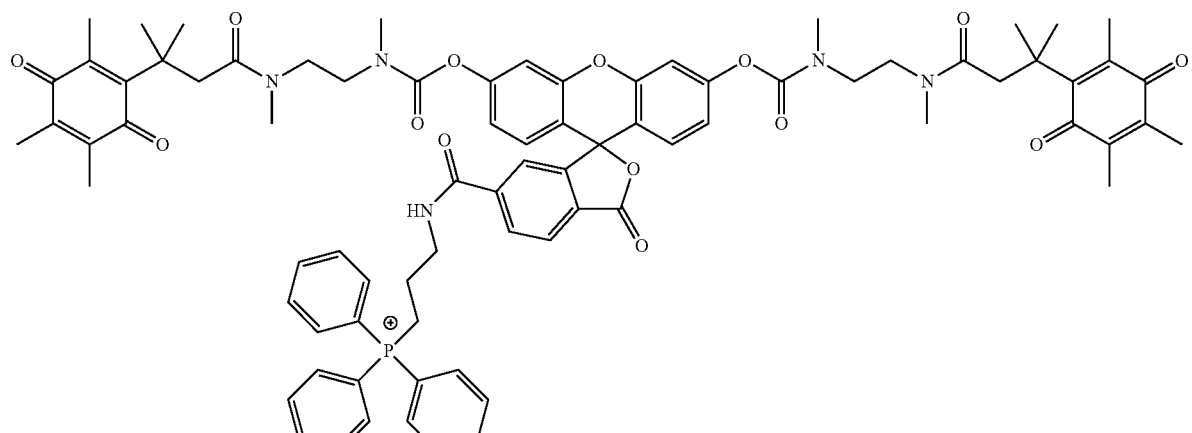

PBI 4543

(3-((tert-butoxycarbonyl)amino)propyl)triphenylphosphonium bromide

A mixture of tert-butyl (3-bromopropyl)carbamate (5.45 g, 22.88 mmol) and triphenylphosphine (6.0 g, 22.88 mmol) in 100 ml of acetonitrile was heated to reflux for 2 days. Upon cooling to room temperature, the compound was purified with silica chromatography using methylene chloride/methanol as an eluent to give a yield of 64% (6.15 g).

(3-Ammoniopropyl)triphenylphosphonium bromide

The solution of TFA/CH$_2$Cl$_2$ (1:1, 50 ml) containing tri-isoproylsilane (0.2 ml) was added to (3-((tert-butoxycarbonyl)amino) propyl)triphenylphosphonium bromide (6.15 g, 14.6 mmol). The mixture was stirred for 2 hours. After removal of the solvent, the compound was dried over vacuum and directly used in next step.

FAM-C3-TPP (PBI 4544)

To a solution of (3-ammoniopropyl)triphenyl phosphonium bromide (0.28 g, 0.54 mmol) in 20 ml DMF, TEA (0.163 g, 1.164 mmol) and 5,6-diacetyl FAM-SE (0.30 g, 0.54 mmol) was added, and the mixture was stirred overnight. Methanol (10 ml) was added to hydrolyze acetyl ester, and the resultant mixture was stirred for 30 minutes. After removal of the solvent, the compound was purified by silica chromatography using methylene chloride/MeOH as an eluent. MS (m/e): 679.4 (M+).

Bis(quinone trimethyllock) FAM-C3-TPP (PBI 4543)

A mixture of FAM-C3-TPP (PBI 4544) (0.10 g, 0.132 mmol), quinone trimethyllock C2-diamine carbonyl chloride (0.20 g, 0.527 mmol), DMAP (0.064 g, 0.527 mmol) and TEA (0.053 g, 0.0527 mmol) was mixed overnight. After removal the excess quinone trimethyllock C2-diamine carbonyl chloride by silica chromatography, the compound was further purified by HPLC using 0.1% formic acid/acetonitrile as an eluent. MS (m/e): 1371.4 (M+).

Example 19
Synthesis of PBI 4547
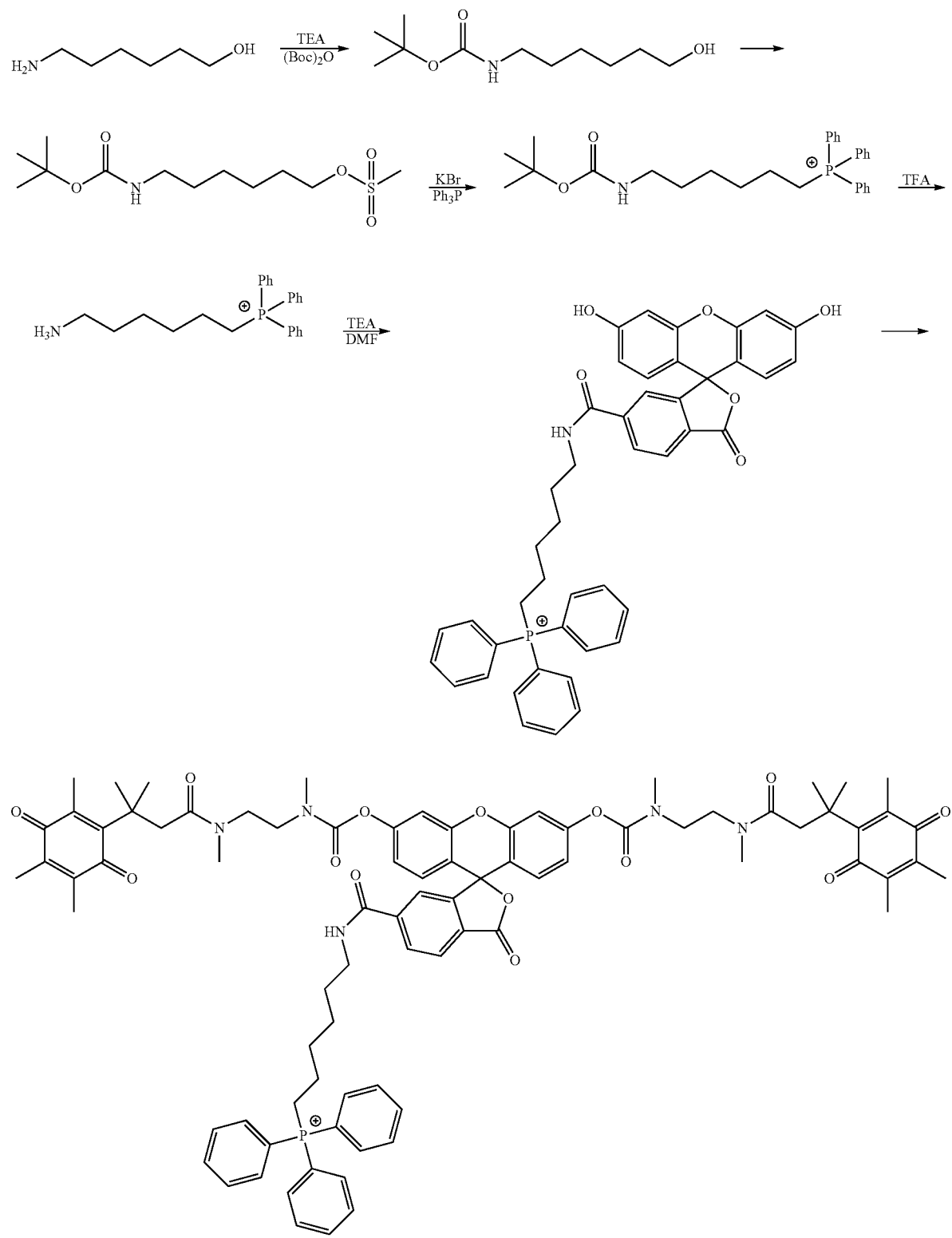
PBI 4547 tert-Butyl (6-hydroxyhexyl)carbamate

To a solution of 6-aminohexan-1-ol (10.0 g, 85.33 mmol) and TEA (12 ml) in 200 ml of $CH_2Cl_2$, a solution of boc anhydride (18.62 g, 85.33 mmol) in 50 ml of methylene chloride was added at 0° C., and the mixture stirred overnight. The mixture was washed with water, and the organic layer was dried over $Na_2SO_4$. After removal of solvent, the compound was dried under a vacuum to give a yield of 87% (16.07 g), which was used directly without further purification.

6-((tert-Butoxycarbonyl)amino)hexyl methanesulfonate

To a solution of tert-butyl (6-hydroxyhexyl)carbamate (12.18 g, 56.05 mmol) and TEA (8.51 g, 84.08 mmol) in 100 ml of methylene chloride, methanesulfonyl chloride (9.63 g, 84.08 mmol) was slowly added at 0° C. The mixture was stirred at room temperature overnight. The compound was purified by silica chromatography using heptane/ethyl acetate as eluent.

(6-((tert-Butoxycarbonyl)amino)hexyl)triphenylphosphonium bromide

A mixture of 6-((tert-butoxycarbonyl)amino)hexyl methanesulfonate (8.0 g, 27.08 mmol), triphenyl phosphine (10.65 g, 40.62 mmol) and KBr (6.45 g, 54.16 mmol) in ACN/DMF (3:1. 120 ml) was heated to reflux for 2 days. After removal of the solvent, the compound was purified using $CH_2Cl_2$/MeOH as an eluent to give a yield of 65% (8.2 0 g).

(6-ammoniohexyl)triphenylphosphonium bromide/TFA salt

A solution of TFA/$CH_2Cl_2$ (1:1, 50 ml) containing triisoproylsilane (0.2 ml) was added to (6-((tert-butoxycarbonyl)amino)hexyl)triphenylphosphonium bromide (8.0 g). The mixture was stirred for 2 hours. After removal of the solvent, the compound was dried over a vacuum and directly used in next step.

FAM-C6-TPP

To a solution of (3-ammoniohexyl)triphenyl phosphonium bromide (0.87 g, 1.79 mmol) in 20 ml DMF, TEA (0.54 g, 5.37 mmol) and 5,6-diacetyl FAM-SE (1.0 g, 0.1.79 mmol) was added, and the mixture stirred overnight. Methanol (10 ml) was added to hydrolyze the acetyl ester, and the resultant mixture was stirred for 30 minutes. After removal of the solvent, the compound was purified by silica chromatography using methylene chloride/MeOH as an eluent to give a yield of 46% (0.59 g). MS (m/e): 721.4 (M+); HPLC purity: 94.7% at 254 nm (5-/6-isomer ratio: 40.9%/53.8%).

Bis(quinone trimethyllock) FAM-C6-TPP (PBI 4547)

The mixture of FAM-C6-TPP (0.10 g, 0.124 mmol), quinone trimethyllock C2-diamine carbonyl chloride (0.19 g, 0.498 mmol), DMAP (0.064 g, 0.527 mmol) and TEA (0.053 g, 0.0527 mmol) in 10 ml of methylene dichloride was stirred overnight. After removal the excess quinone trimethyllock C2-diamine carbonyl chloride by silica chromatography, the compound was further purified by HPLC using 0.1% formic acid/acetonitrile as an eluent. MS (m/e): 1413.5 (M+); HPLC purity: 85% at 254 nm (5-/6-FAM isomers cannot be separated by HPLC).

Example 20

Synthesis of PBI 4442

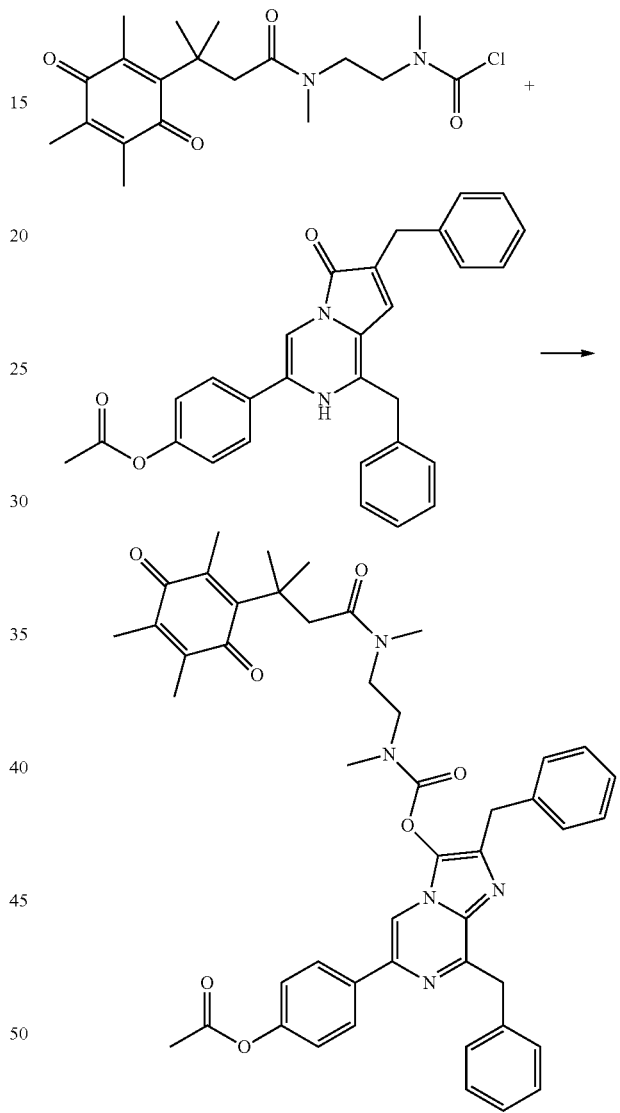

PBI 4442

A mixture of coelenterazine acetyl ester (0.50 g, 1.14 mmol), quinone trimethyllock C2-diamine carbonyl chloride (0.436 g, 1.14 mmol), DMAP (0.139 g, 1.14 mmol) and TEA (0.115 g, 1.14 mmol) in 20 ml of methylene dichloride was stirred overnight at room temperature. The compound was purified by silica chromatography using heptane/ethyl acetate as an eluent to give a yield of 20% (0.184 g). $^1$H NMR (300 MHz, $CD_2Cl_2$) δ 8.47 (s, 1H), 8.04 (d, 2H), 7.55 (d, 2H), 7.0-7.5 (m, 9H), 4.57 (s, 2H, CH2), 4.16 (s, 2H, CH2), 3.2-3.7 (m, 4H, NCH2), 2.7-3.2 (m, 8H, 2NCH3+$CH_2$), 2.30 (s, 3H, CH3), 1.0-2.2 (m, 15H, CH3). MS (m/e): 796.5 (M+).

Example 21

Synthesis of PBI 4600

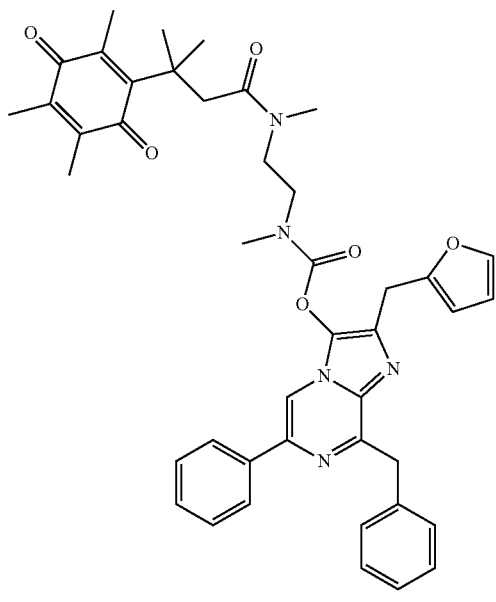

PBI 4600

PBI 4600 was made by employing the similar method for preparing PBI 4442 (Example 20). The compound was purified by silica chromatography using heptane/ethyl acetate as an eluent to give a yield of 60% (0.32 g). $^1$H NMR (300 MHz, CD2C12) δ 8.47 (s, 1H), 8.03 (m, 2H), 7.57 (d, 2H), 7.1-7.5 (m, 7H), 6.33 (s, 1H), 6.17 (s, 1H), 4.58 (s, 2H, CH2), 4.19 (s, 2H, CH$_2$), 3.3-3.7 (m, 4H, NCH2), 2.7-3.2 (m, 8H, 2NCH3+CH$_2$), 1.0-2.2 (m, 15H, CH3). MS (m/e): 728.5 (M+). HPLC purity: 90% at 262 nm.

Example 22

Synthesis of PBI 4601

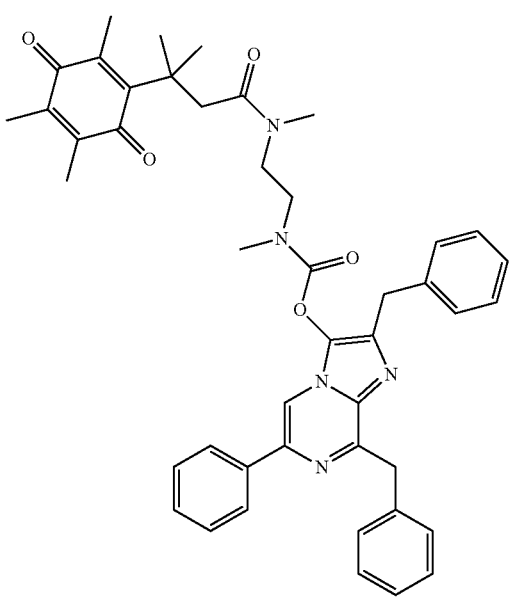

PBI 4601

PBI 4601 was made by employing the similar method for preparing PBI 4442 (Example 20). The compound was purified by silica chromatography using heptane/ethyl acetate as an eluent to give a yield of 17% (0.15 g). $^1$H NMR (300 MHz, CD$_2$Cl$_2$) δ 8.42 (s, 1H), 7.99 (m, 2H), 7.57 (d, 2H), 7.1-7.5 (m, 10H), 4.58 (s, 2H, CH2), 4.19 (s, 2H, CH2), 3.3-3.7 (m, 4H, NCH2), 2.7-3.2 (m, 8H, 2NCH3+CH$_2$), 1.0-2.2 (m, 15H, CH3). MS (m/e): 738.5 (M+). HPLC purity: 95% at 262 nm.

Example 23

Analysis of Substrates in Different Cell Types

This example demonstrates the use of the substrates of the present invention in three different cell lines: A549 (adenocarcinomic human alveolar basal epithelial cell line), Jurkat (human T-lymphocyte cell line), and HepG2 (human liver carcinoma cell line).

Figure 1:
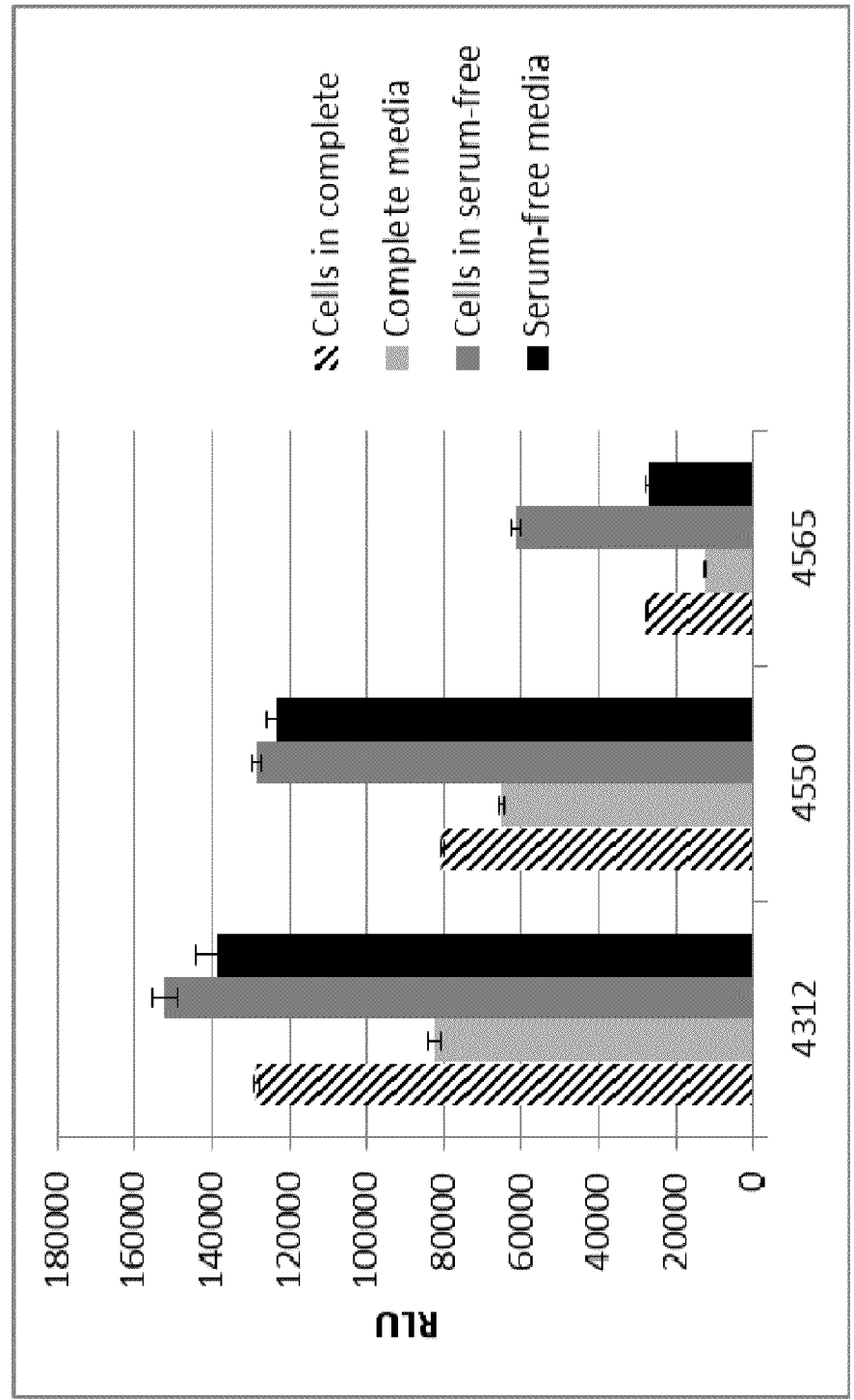
FIG. 1. shows the analysis of compounds 4312, 4550, and 4565 in Jurkat cells. Jurkat cells were plated at 50,000 cells/well. Cells were treated with 50 µM of each compound for 1 hour. Luminescence (RLUs) was detected for each compound.

Jurkat cells were plated at 50,000 cells/well in either 10% serum media or serum-free media into wells of a 96-well assay plate. 50 μM PBI-4312, 4550 or 4565 was added to the cell media, and the cells incubated at 37° C. for 30 minutes then room temperature for 30 minutes. 50 μl of Luciferin Detection Reagent (LDR; Promega) was added to each well and incubated for 20 minutes at room temperature. Luminescence (RLUs) was detected on a Promega GloMax® luminometer (FIG. 1).

Figure 2A:
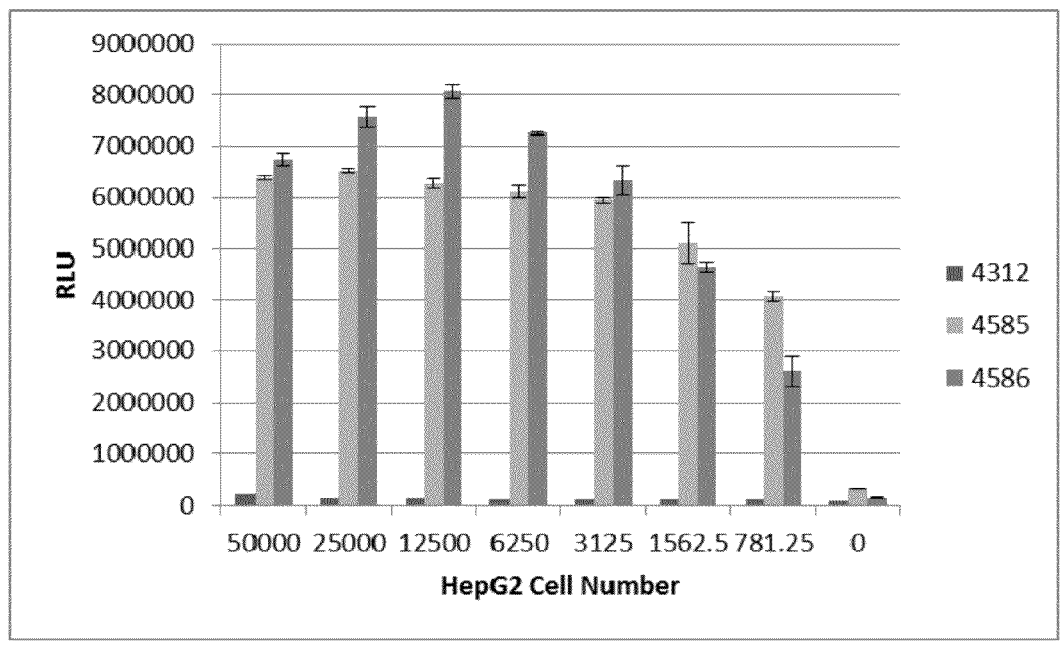
FIG. 2 shows the analysis of compounds 4312, 4585, and 4586 in HepG2 cells. HepG2 cells were plated at different cell densities into wells of a 96-well assay plate. Cells were treated with 50 µM of each compound for 1 hour. Luminescence (RLU) was detected (a), and the signal-to-background (S/B) was calculated by dividing the sample RLU by the RLU generated by each compound in media (b).
Figure 2B:
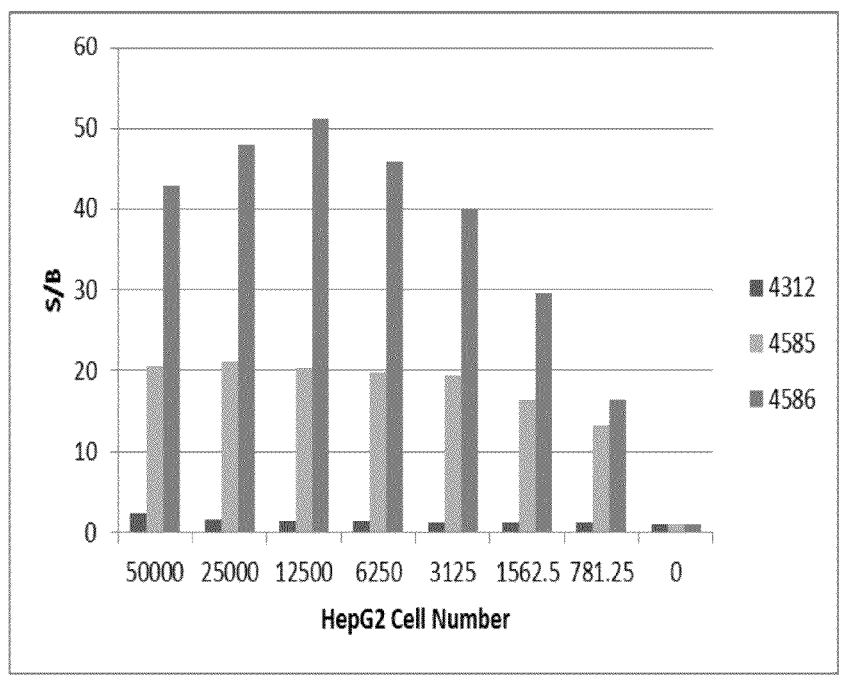

HepG2 cells were plated at different cell densities (50,000; 25,000; 12,500; 6250; 3125; 1562.5; or 781.25 cells/well) in 10% serum media into wells of a 96-well assay plate. 50 μM PBI-4312, 4585 or 4586 was added to the cell media, and the cells incubated at 37° C. for 30 minutes then at room temperature for 30 minutes. 50 μl of Luciferin Detection Reagent (LDR; Promega) was added to each sample and incubated for 20 minutes at room temperature. Luminescence (RLUs) was detected on a Promega GloMax® luminometer (FIG. 2a). Signal-to-background (S/B; FIG. 2b) was determined by dividing the sample RLU by the RLU generated by each compound in media only (no cells).

Figure 3A:
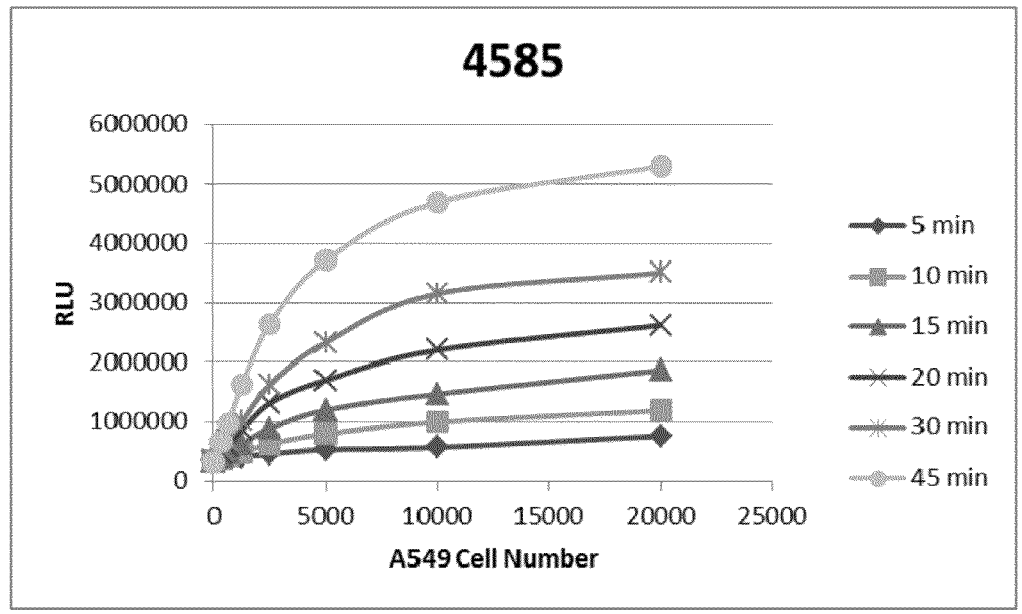
FIG. 3 shows the analysis of compounds 4585 and 4586 in A549 cells. A549 cells were plated at different cell densities into wells of a 96-well assay plate and treated with 100 µM of each compound. An aliquot of cell media was taken at different time points, and luminescence (RLUs) detected (3a and 3c). Signal-to-background (S/B) was calculated by dividing the sample RLU by the RLU generated by each compound in media alone (3b and 3d).
Figure 3B:
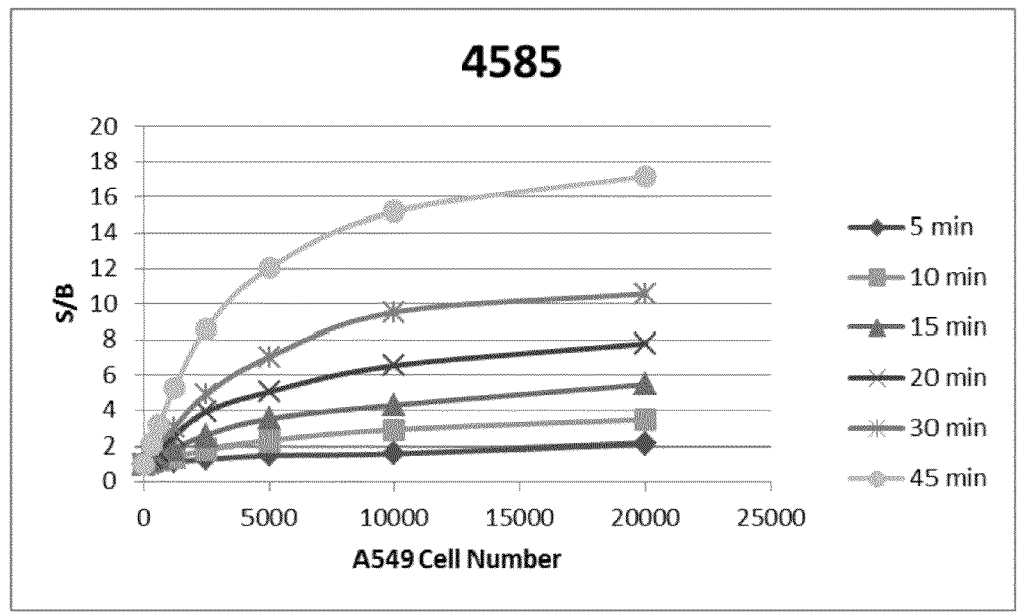
Figure 3C:
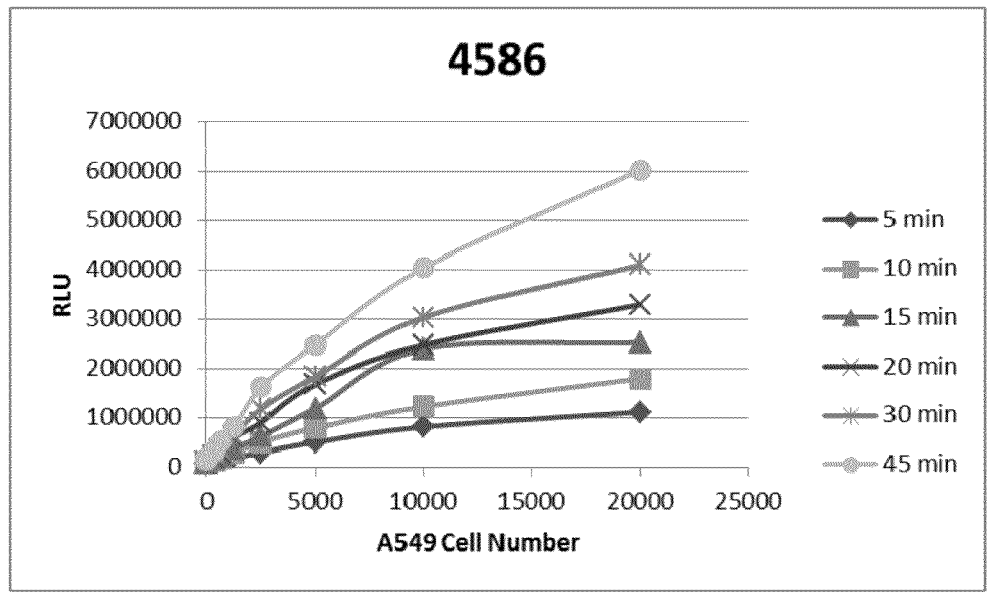
Figure 3D:
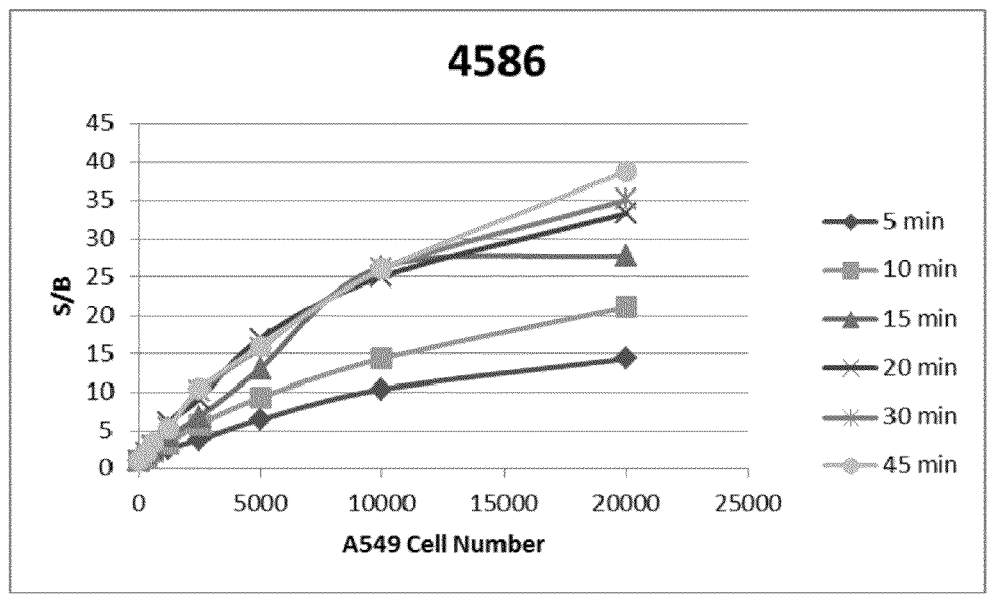
Figure 4A:
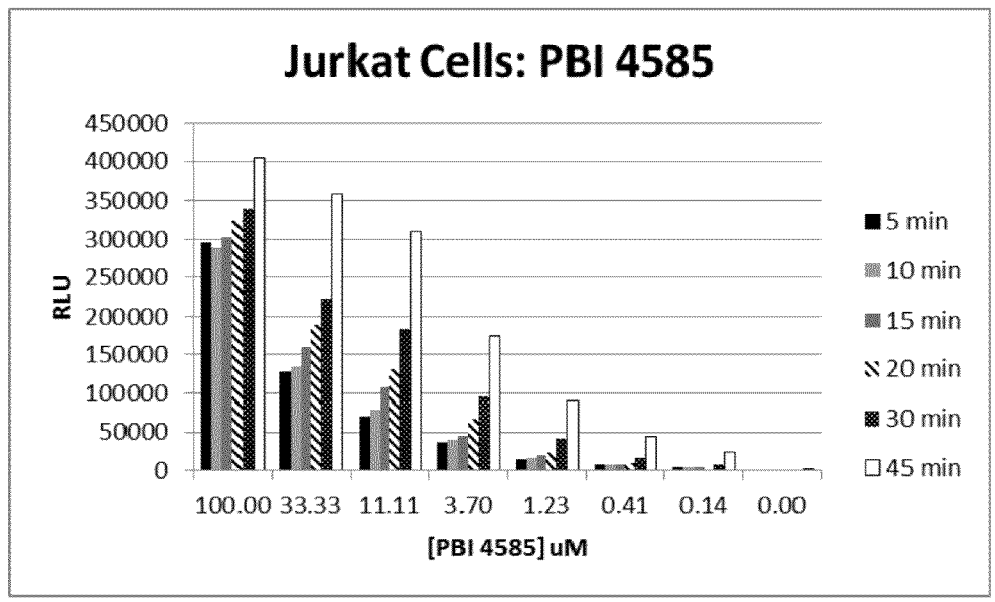
FIG. 4 shows pro-luciferin compound titration. Jurkat (4a and 4b) or A549 cells (4c and 4d) were plated at 40,000 cells/well in a 96-well assay plate and treated with increasing concentrations of the pro-luciferin compounds 4585 (4a and 4c) and 4586 (4b and 4d). The relative light units (RLUs) were determined at different time points ranging from 5 minutes to 45 minutes post-compound addition.
Figure 4B:
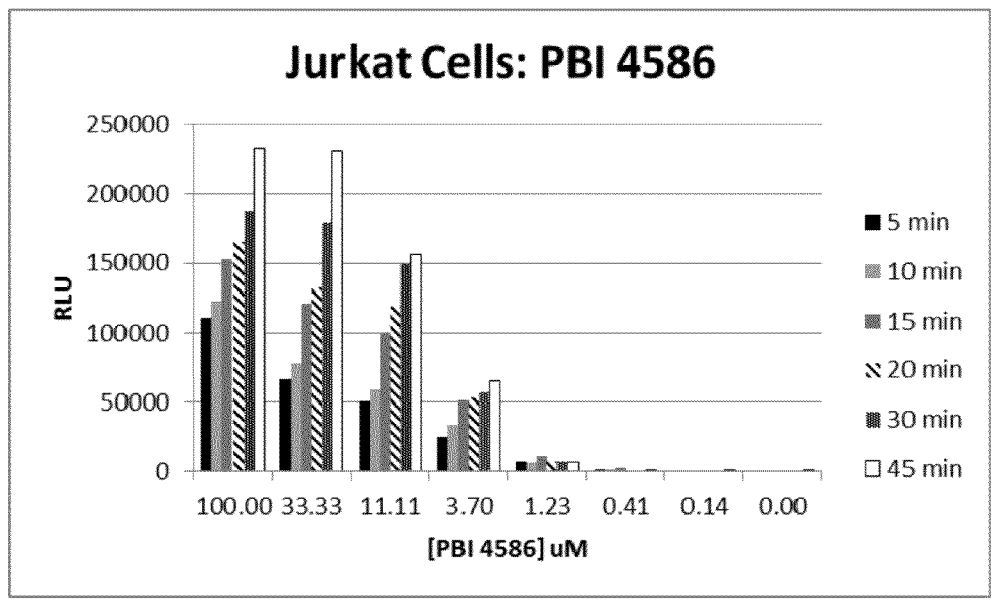
Figure 4C:
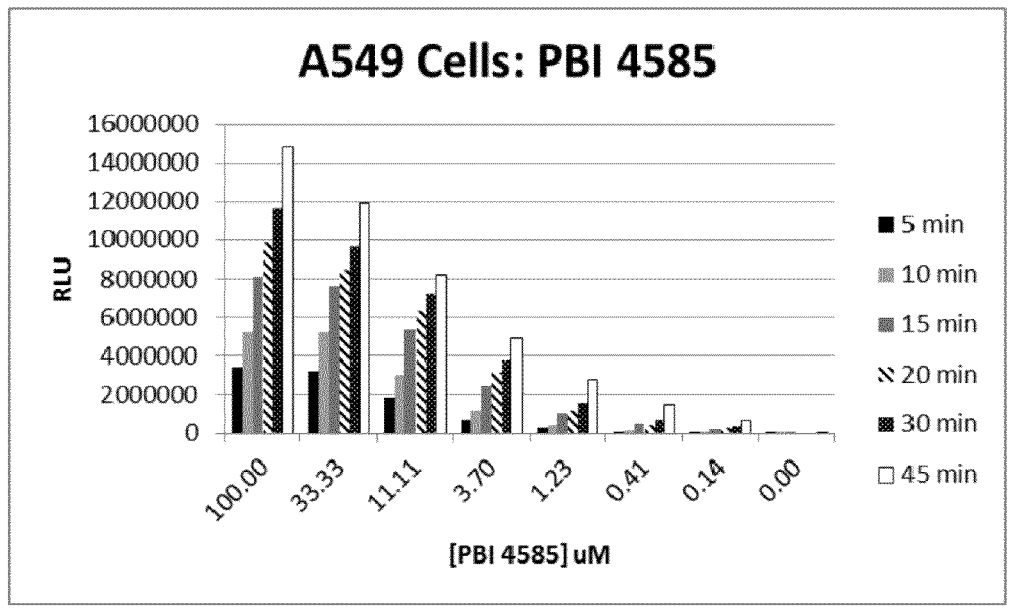
Figure 4D:
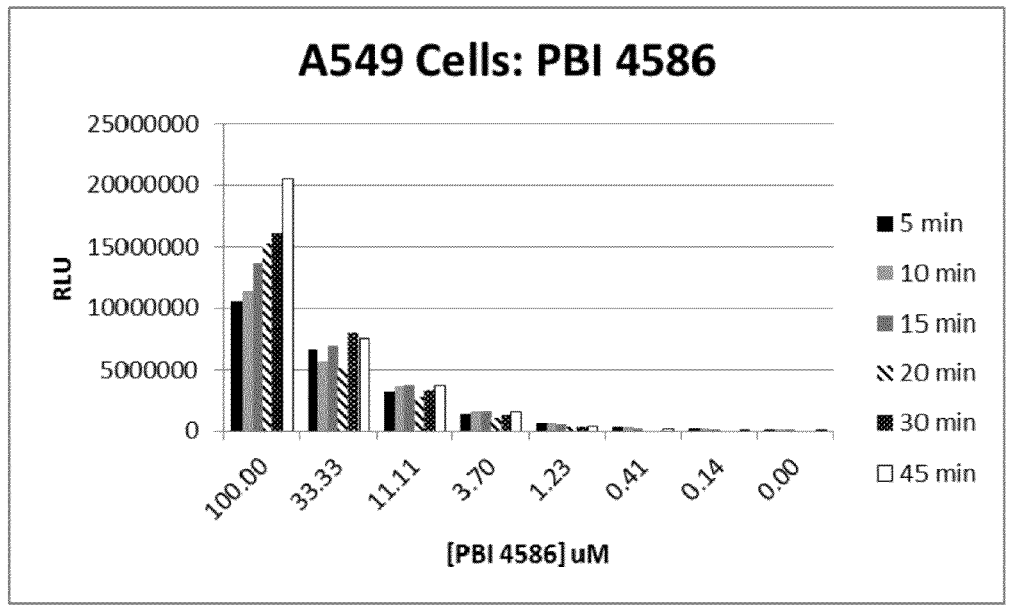

A549 cells were plated at different cell densities (20,000; 10,000; 5,000; 2,500; 1, 250; 625; 312.5 cells/well) in 10% serum media into wells of a 96-well assay plate. 100 μM PBI-4585 or 4586 was added to the cell media, and the cells incubated at room temperature for various time periods (5, 10, 15, 20, 30, or 45 minutes). A sample (50 μl) of the cell media was taken at each time point and added to 50 μl of Luciferin Detection Reagent (LDR; Promega). The samples were incubated for 20 minutes at room temperature. Luminescence (RLUs) was detected on a Promega GloMax® luminometer (FIGS. 3a and 3c). Signal-to-background (S/B; FIGS. 3b and 3d) were determined by dividing the sample RLU by the RLU generated by each compound in media only (no cells).

Optimal concentrations of 4585 and 4586 in Jurkat and A549 cells were determined by performing a compound titration. Jurkat or A549 cells were plated at 40,000 cells/well into wells of a 96-well assay plate. Increasing concentrations (0.14, 0.41, 1.23, 3.70, 11.11, 33.33 and 100 μM) of PBI-4585 or 4586 was added to the cell media. The cells were incubated at room temperature for various time periods (5, 10, 15, 20, 30, or 45 minutes). 50 μl of Luciferin Detection Reagent (LDR; Promega) was added at each time point. The samples were incubated for 20 minutes at room temperature. Luminescence (RLUs) was detected on a Promega GloMax® luminometer (FIG. 4a-d).

Example 24

Determining Redox State

This example demonstrates the use of the substrates of the present invention to determine metabolic cell health. The substrates PBI 4312 and 4586 were screened for their ability to assess metabolic cell health in menadione-treated A549 cells.

Figure 5:
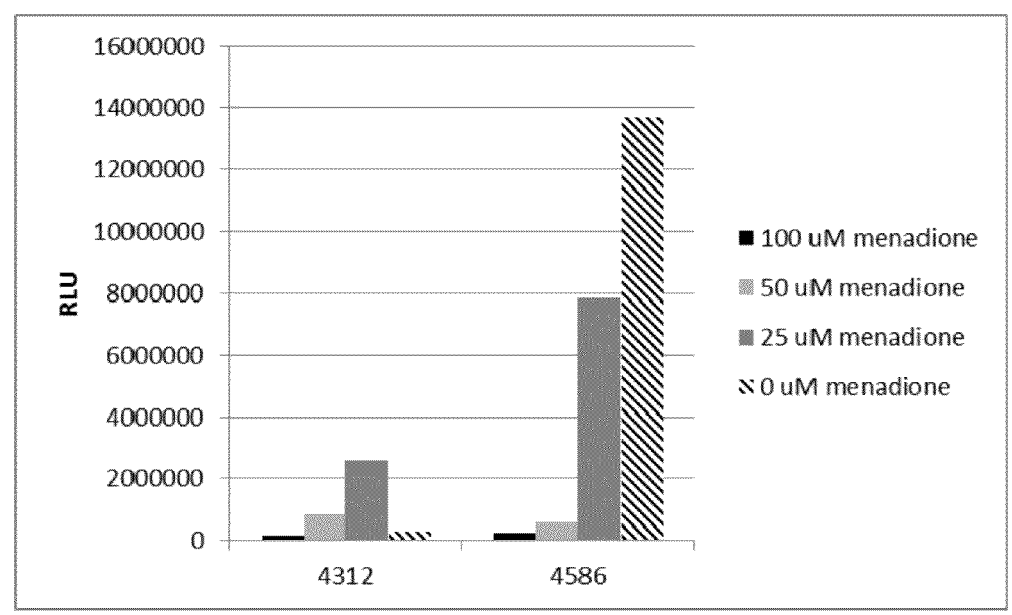
FIG. 5 shows the analysis of the redox state of menadione-treated A549 cells. A549 cells were plated at 20,000 cells/ well in a 96-well assay plate and treated with various concentrations of menadione for 1 hour. PBI-4312 or 4586 was then added to the cells and incubated at room temperature for 1 hour. Luminescence (RLUs) was detected for each treatment.

A549 cells were plated at 20,000 cells/well into wells of a 96-well assay plate. Cells were treated with various concentrations (0, 25, 50 or 100 μM) of menadione for 1 hour at 37° C. The cells were then treated with 50 uM PBI-4312 or 4586 and incubated at room temperature for 1 hour. 50 μl of Luciferin Detection Reagent (LDR; Promega) was then added. The samples were incubated for 20 minutes at room temperature. Luminescence (RLUs) was detected on a Promega GloMax® luminometer (FIG. 5).

Example 25

Fluorescent Imaging of Live Cells

HeLa cells were plated at 40,000 cell/well into wells of an 8-well chambered coverslip and incubated at 37° C.+5% $CO_2$. The media (DMEM) was replaced with warm complete media (with 10% FBS) containing 10 μM PBI-4412, 4413, 4440 or 4441. Cells were then transferred to a confocal microscope for imaging using 10% λ488 nm laser power (4412, 4413, and 4441) or 5% laser power (4440). All images (FIGS. 6a-d) are at 30× magnification. The images show that the substrates are only reduced once inside cells.

Example 26

Mitochondrial-Targeted Substrates

HeLa cells were plated at 50,000 cell/well into wells of an 8-well chambered coverslip and incubated at 37° C.+5% $CO_2$. The media (DMEM) was replaced with complete media (DMEM with 10% FBS) containing 10 uM PBI-4543 or 4547 for 1 hour. Media was then replaced with low serum media (1% FBS) containing 50 nM Mito Tracker DeepRed FM (Invitrogen) as per manufacture's instructions. Cells were then transferred to a confocal microscope for imaging using λ488 nm laser for viability (4543 or 4547) or λ633 nm laser for Mito Tracker in sequential mode. All images (FIGS. 7a-b) are at 100× magnification.

Example 27

Cellular Function Assay

HeLa cells were plated at 50,000 cell/well into wells of a 8-well chambered coverslip and incubated at 37° C.+5% $CO_2$. The media (DMEM) was replaced with complete media (with 10% FBS) containing 10 μM PBI-4543 or 4547. The cells were incubated for 30 minutes, and 6.8 mM 3-nitropropionic acid (3-NPA; known inhibitor of electron transport chain (ETC) via complex II) was added the cells. Controls cells received no 3-NPA. Cells were then incubated for 85 minutes and then transferred to a confocal microscope for imaging using 10% λ488 nm laser. All images (FIGS. 8a-d) are at 40× magnification.

Example 28

Measuring Metabolically Active Cells Using Quinone Derivatives

This example demonstrates the use of quinone derivatives, a coelenterazine and fluorescent derivative, to measure the amount of metabolically active cells. Viable cells maintain a metabolically active state that is inevitably lost when cells are damaged. Upon entering the living cells, the quinone coelenterazine is reduced to a coelenterazine derivative that is a substrate for a coelenterazine-utilizing luciferase, e.g., *Oplophorus* or *Renilla* luciferase. Conversion of the quinone coelenterazine is proportional to the number of metabolically active cells, and therefore can be measured quantitatively by monitoring light produced by luciferase reaction. Similarly, quinone derivatives coupled to fluorophores can be used to measure the amount of metabolically active cells by measuring the increase in fluorescence values.

A. Quinone Coelenterazine Derivatives

Two-fold serial dilutions of Jurkat cells were prepared in PBS, and 50 μl per well transferred to wells in 96-well plates. Compound PBI 4600 and 4601 were diluted in PBS to make 50 μM and 100 μM stocks, respectively. 10 μl of prepared compound stocks were added to the cells, and the cells were placed into 37° C., 5% $CO_2$ incubator. Following a 30 minute incubation, the cells were removed from incubator, cooled at room temperature for 10 minutes, and 50 μl of *Oplophorus* luciferase detection reagent (Promega Corporation) added directly to the wells. The samples were mixed, incubated at room temperature for 20 minutes, and luminescence measured. FIG. 9 shows the linear correlation between cell number and luminescence indicating a direct relationship between luminescence and cell number.

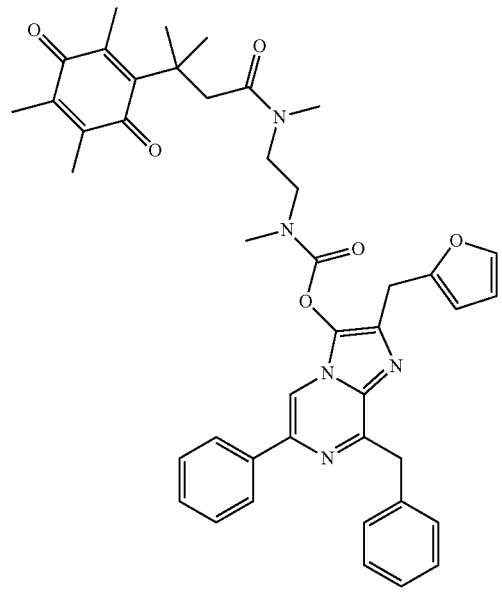

4600

-continued

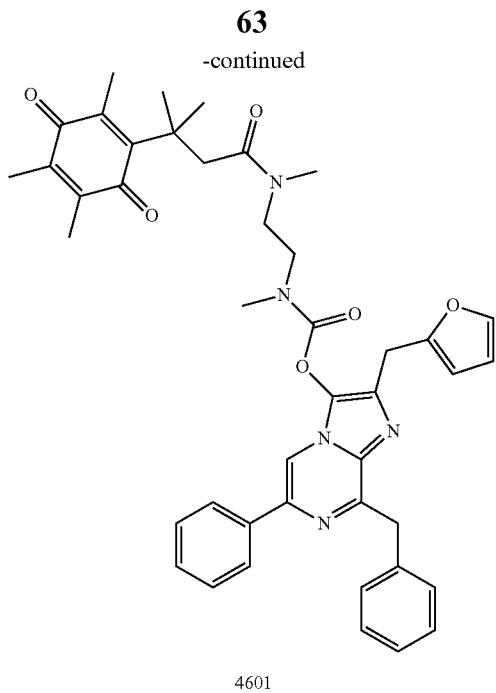

4601

B. Quinone Fluorescein Derivatives i. Two-fold serial dilutions of HEK293 cells were prepared in full DMEM media, and 100 µl per well were transferred into wells of 96-well plates. Compounds PBI 4440 and 4412 were diluted in full DMEM media to make 20 µM and 10 µM stocks, respectively. 100 µl of the prepared compound stocks were added to the cells, and the cells were incubated for 60 minutes in a 37° C., 5% $CO_2$ incubator. Following incubation, the cells were removed from incubator, and fluorescence measured with Tecan Infinite 500 at 480ex/Em530em wavelength. FIG. 10 shows the linear correlation between cell number and fluorescence indicating a direct relationship between fluorescence measured with compounds 4440 and 4412 and cell number.

ii. To induce cytotoxicity, cells were treated with digitonin. A452 cells were plated at 50,000 cells/per well into wells of a 96-well plate. After 24 hours, the media was removed, and 100 µl fresh media with or without 50 µg/ml of digitonin was added. The cells were incubated for 30 minutes at 37° C., 5% $CO_2$. After incubation, 100 µl of media containing 20 µM compound 4440 was added. The cells were incubated another 30 minutes, and fluorescence measured as described above. As seen in FIG. 11, a greater than 90% decrease in fluorescent signal was seen after digitonin treatment illustrating the ability of compound 4440 to measure a decrease in cell viability.

Example 29

Screening for a Compound that Affects Cell Viability

A549 cells were plated into wells of a 384-well assay plate at 250 cells/well. Cells were treated with dose curves of staurosporine or doxorubicin for 72 hours. After 72 hours, 50 uM PBI 4586 was added to the cell culture and incubated at room temperature for 30 minutes. LDR and 10 mM D-cysteine was added to the reaction and incubated at room temperature for 20 minutes. Luminescence was measured on a Tecan M1000.

The results illustrate the use of the method described to rapidly identify and characterize compounds affecting cell viability (FIG. 12).

Example 30

Detection of Lactate, Ethanol, or Glucokinase

To demonstrate the ability of the substrates of the present invention to detect lactate, ethanol or glucokinase, the proluciferin substrate, PBI-4312, was combined with a diaphorase enzyme, NAD or NADP, and a dehydrogenase enzyme (lactate dehydrogenase (LDH), alcohol dehydrogenase or glucose-6-phosphate (G6P) dehydrogenase). The NADH generated by the dehydrogenase reacting with its substrate is utilized by the diaphorase enzyme to convert the proluciferin substrate to luciferin which can then be detected using a luciferase detection reagent. (FIG. 14)

A. Detection of Lactate in Cells

Figure 15A:
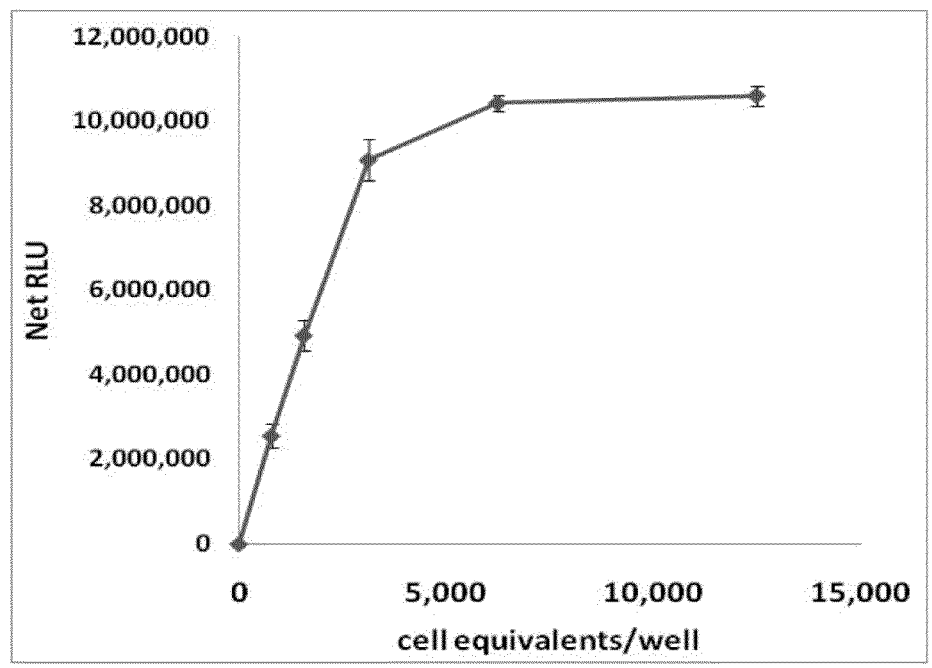
Figure 15B:
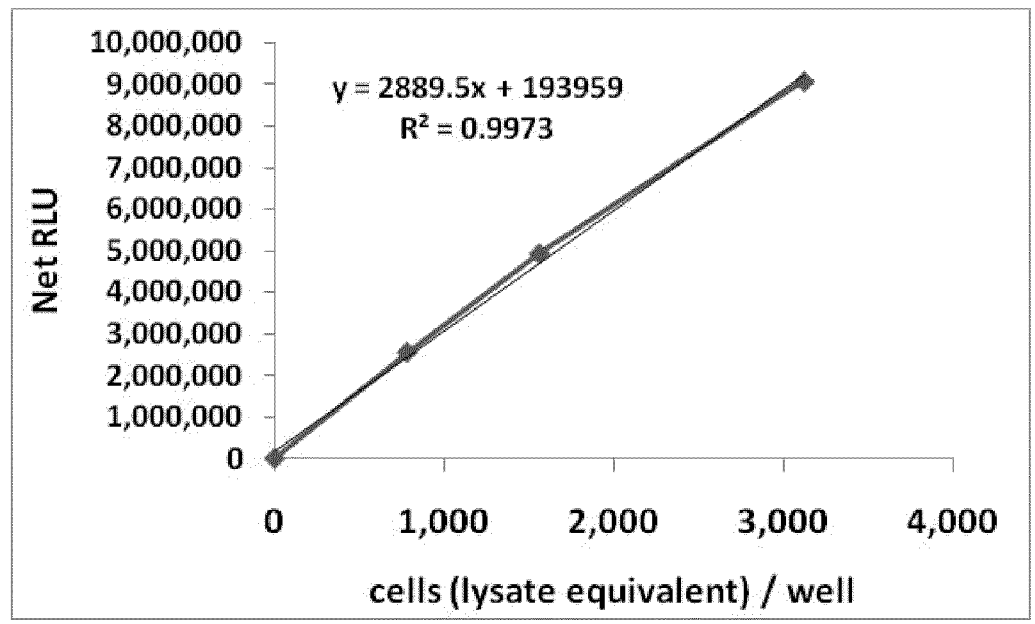

Jurkat cells were lysed at 2× concentration in PBS+0.1% Triton. Serial dilutions (5,000; 10,000; or 15,000 cell equivalents/well) were made in the same lysis buffer and plated into wells of a 96-well luminometer plate. The volume of the cell lysate was 25 µl. To the cell lysates, 25 ul of a 2× reaction mixture (2.5 mM NAD, 13.4 units/ml diaphorase (Sigma), 50 µM PBI-4312, 16 units/ml lactate dehydrogenase (Type II, Rabbit Muscle) was added and incubated at room temperature for 15 minutes. 50 µl Luciferin Detection Reagent (Promega Cat. No. V8920) and 0.5 mM menadione was added to the wells and incubated for 15 minutes at room temperature. Luminescence (RLUs) was detected on a Promega GloMax® luminometer. FIG. 15a shows the net RLUs generated from the reaction. FIG. 15b shows the correlation between cell number and luminescence indicating a direct relationship between luminescence generated via proluciferin conversion and lactate concentration.

B. Detecting Ethanol

Figure 16A:
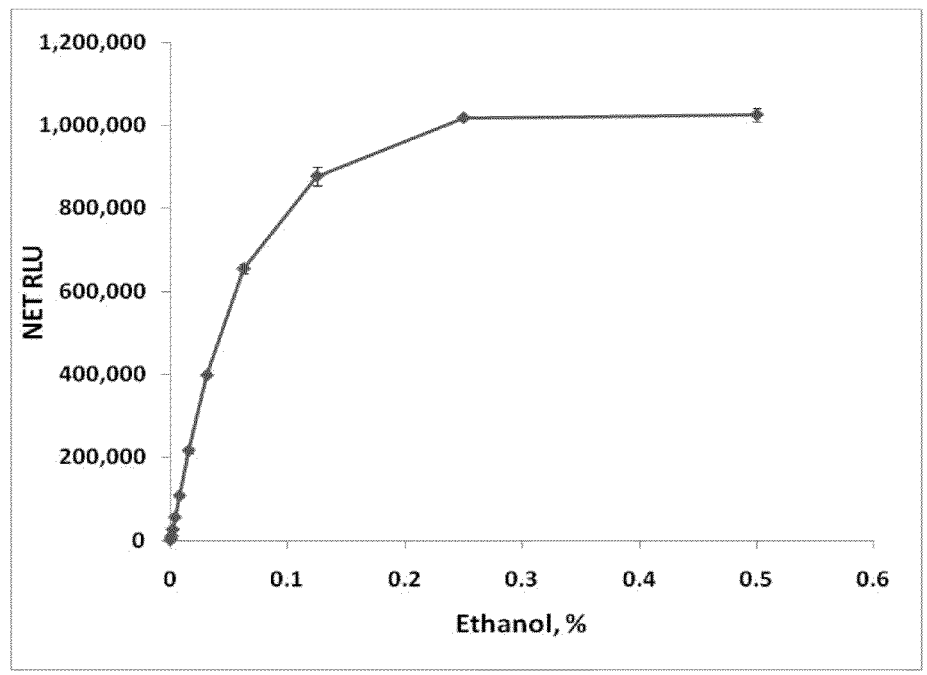
Figure 16B:
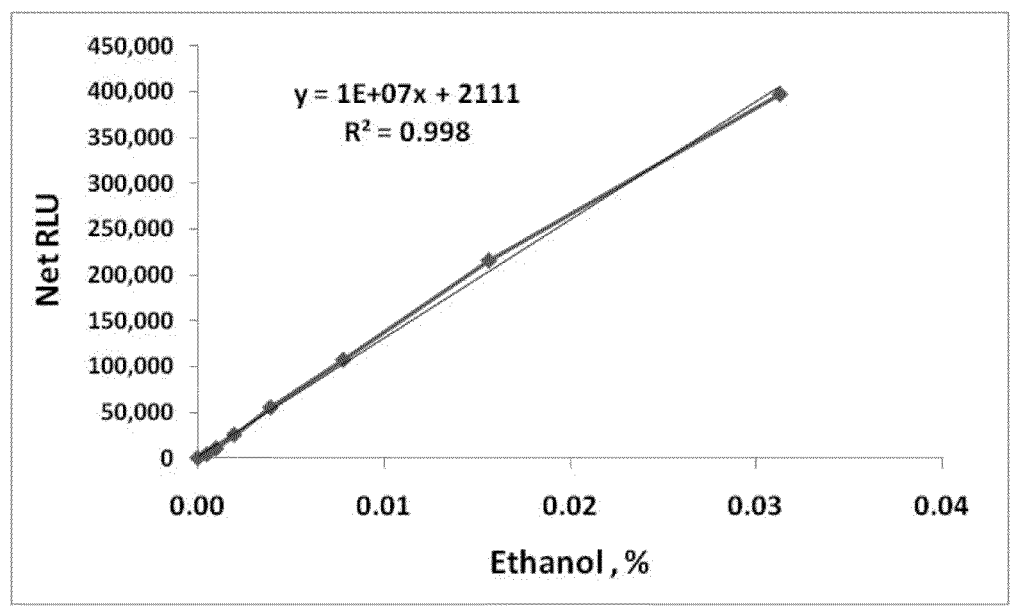

Serial dilutions of 2× ethanol in 1×PBS were added to wells of a 96-well luminometer plate. The volume of ethanol was 15 µl. To the ethanol, 15 µl of a 2× reaction mixture, 25 µl of a 2× reaction mixture (2.5 mM NAD, 12.5 units/ml diaphorase (Sigma), 50 µM PBI-4312, 16 units/ml alcohol dehydrogenase (yeast) was added and incubated at room temperature for 15 minutes. 30 µl LDR and 0.5 mM menadione was added to the wells and incubated for 15 minutes at room temperature. Luminescence (RLUs) was detected as previously described. FIG. 16a shows the net RLUs generated from the reaction. FIG. 16b shows the correlation between luminescence generated via proluciferin conversion and ethanol concentration.

C. Detecting Glucose-6-Phosphate

Serial dilutions of 2× glucose-6-phosphate (G6P) in 1×PBS were added to wells of a 96-well luminometer plate. The volume of G6P was 15 µl. To the G6P, 15 µl of a 2× reaction mixture (200 µM NAD, 13.4 units/ml diaphorase (Sigma), 50 µM PBI-4312, 0.1 units/ml glucose-6-phosphate dehydrogenase (*L. mesenteroids*) was added and incubated at room temperature for 15 minutes. 30 µl LDR and 0.5 mM menadione was added to the wells and incubated for 15 minutes at room temperature. Luminescence (RLUs) was detected as previously described. FIG. 17 shows the linear correlation between luminescence generated via proluciferin conversion and G6P concentration.

D. Detecting Glucokinase in Cells

HepG2 cells were dounced and sonicated in 2× buffer (100 mM KCl, 25 mM HEPES pH 7.5, 7.5 mM MgCl$_2$, 4 mM DTT). Serial dilutions (0; 12,000; 25,000; 50,000; and 100,000 cell density/reaction as lysate) were made in the 2× buffer and added to wells of a 96-well luminometer plate. The volume of cell lysate was 25 µl. To the cell lysates, 25 µl of a 2× reaction mixture (200 µM NADP, 13.4 units/ml diaphorase (Sigma), 50 µM PBI-4312, 0.2 units/ml glucose-6-phosphate dehydrogenase (*L. mesenteroids*) was added and incubated at room temperature for 15 minutes. 50 µl LDR and 0.5 mM menadione was added to the wells and incubated for 15 minutes at room temperature. Luminescence (RLUs) for the samples wherein the difference between luminescence at 100 mM and 0.5 mM glucose indicated glucokinase activity. (FIG. 18)

Example 31

NADH Detection and Measurement

The following examples demonstrate the use of the proluciferin substrates PBI-4312, 4550 and 4565 to detect and measure NADH. Luminescence generated is indicative of the presence of NADH and diaphorase.

A. NADH Detection Using PBI-4312, 4550 or 4565.

Each substrate (PBI-4312, 4550 and 4565) was incubated at 20 µM with 0 µM or 10 µM NADH (Sigma) and 0 u/ml or 5 u/ml rat diaphorase (Sigma) in a volume of 10 µl in 50 mM Tris pH 7.5. Reactions were performed in quadruplicate in a 384-well white luminometer plate and incubated at room temperature for 20 minutes. 10 µl LDR was added to each sample, incubated for 20 minutes at room temperature, and luminescence detected on a Tecan plate luminometer. The RLUs from the quadruplicates were averaged (Table 1).

TABLE 1

| Compound | Proluciferin In reaction? | NADH In reaction? | Diaphorase In reaction? | Avg RLU | S.D. | % C.V. |
|---|---|---|---|---|---|---|
| 4312 | Yes | Yes | yes | 197017 | 21600 | 11 |
|  | Yes | Yes | no | 3918 | 251 | 6 |
|  | Yes | No | yes | 3910 | 431 | 11 |
|  | No | Yes | yes | 23.5 | 10 | 44 |
|  | Yes | No | no | 4262 | 265 | 6 |
|  | No | No | no | 15 | 9 | 62 |
| 4550 | Yes | Yes | yes | 125597 | 5615 | 4 |
|  | Yes | Yes | no | 3075 | 308 | 10 |
|  | Yes | No | yes | 2848 | 216 | 8 |
|  | No | Yes | yes | 24 | 3.7 | 15 |
|  | Yes | No | no | 3070 | 139 | 5 |
|  | No | No | no | 20 | 8.5 | 42 |
| 4565 | Yes | Yes | yes | 98349 | 14792 | 15 |
|  | Yes | Yes | no | 891 | 40 | 4 |
|  | Yes | No | yes | 860 | 48 | 6 |
|  | No | Yes | yes | 25 | 12 | 50 |
|  | Yes | No | no | 801 | 79 | 10 |
|  | No | No | no | 14 | 5 | 35 |

B. Detecting NADH with Rat Diaphorase or *Clostridium* Diaphorase

Figure 19A:
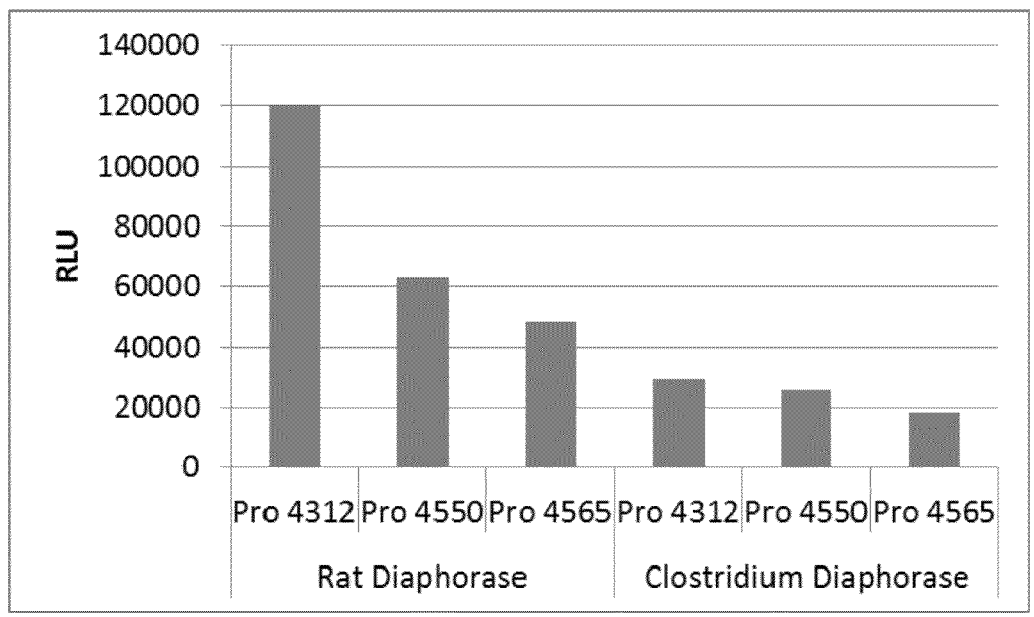
Figure 19B:
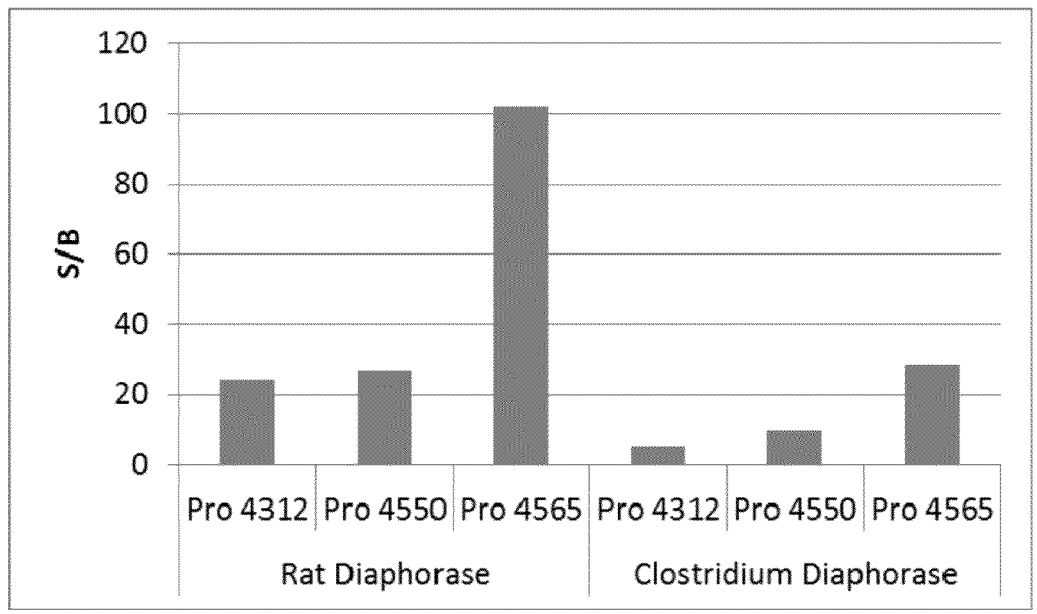

Each compound was incubated at 20 µM with 10 µM NADH (Sigma) and 5 u/ml rat diaphorase (Sigma) or 0.5 u/ml *Clostridium* diaphorase (Sigma) in a volume of 10 µl in 50 mM Tris pH 7.5. Negative control reactions lacking NADH were also included. The samples were incubated at room temperature for 30 minutes, 10 µl LDR added, and luminescence measured every 10 minutes for 70 minutes as previously described. Luminescence (RLUs) at 70 minutes is shown in Table 2. Quadruplicate reactions were performed, and the RLUs averaged (FIG. 19a). Signal to background ratios (S/B) were also calculated by dividing the signal from reactions with NADH by the signal from the reactions without NADH (FIG. 19b).

TABLE 2

| | | With NADH | | | Without NADH | | | |
|---|---|---|---|---|---|---|---|---|
| Diaphorase | Compound | Avg RLU | S.D. | % C.V. | Avg RLU | S.D. | % C.V. | S/B |
| Rat | 4312 | 120633 | 5032 | 4.2 | 4981 | 307 | 6.2 | 24 |
| Rat | 4550 | 62987 | 2184 | 3.5 | 2337 | 127 | 5.4 | 27 |
| Rat | 4565 | 48903 | 1652 | 3.4 | 479 | 108 | 22.5 | 102 |
| *Clostridium* | 4312 | 29068 | 994 | 3.4 | 5311 | 552 | 10.4 | 5.5 |
| *Clostridium* | 4550 | 25644 | 557 | 2.2 | 2597 | 325 | 12.5 | 10 |
| *Clostridium* | 4565 | 18559 | 1234 | 6.6 | 646 | 44 | 6.8 | 29 |

C. NADH Titration

Figure 22B:
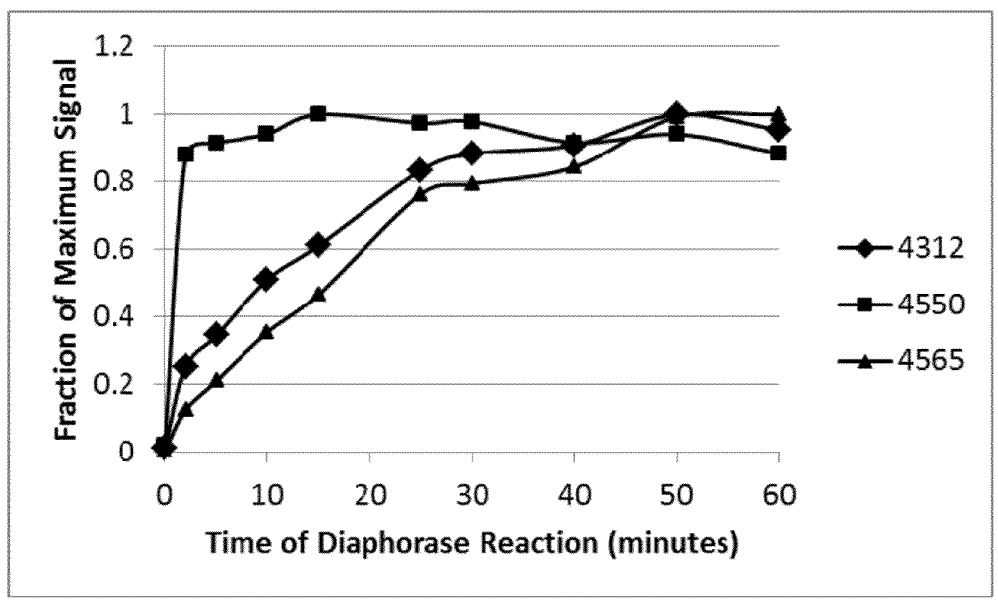

Each compound was incubated at 20 μM with increasing amounts of NADH (Table 3) (Sigma) and 5 u/ml rat diaphorase (Sigma) in a volume of 10 μl in 50 mM Tris pH 7.5. Quadruplicate reactions were performed. The samples were incubated for 40 minute at room temperature, 10 μl LDR added, and incubated for 20 minutes at room temperature. Luminescence was detected as previously described, and RLUs of the quadruplicate reactions averaged (Table 3 and FIG. 20).

rase (Sigma) in a volume of 10 μl in 50 mM Tris pH 7.5. Forty identical reactions were prepared. At the timepoints indicated in Table 5, 10 μl LDR with 500 μM menadione was added to 4 of the reactions for each compound. Luminescence was measured at as previously described. RLUs of quadruplicate reactions were averaged (Table 5 and FIG. 22a). Each average signal was also divided by the maximum signal obtained with that compound to calculate the fraction of maximum signal (FIG. 22b).

TABLE 3

| NADH | Compound 4312 | | | Compound 4550 | | | Compound 4565 | | |
|---|---|---|---|---|---|---|---|---|---|
| (μM) | Avg RLU | S.D. | % C.V. | Avg RLU | S.D. | % C.V. | Avg RLU | S.D. | % C.V. |
| 100 | 663944 | 82043 | 12 | 322628 | 51886 | 16 | 306242 | 34007 | 11 |
| 50 | 687602 | 157886 | 23 | 260182 | 94365 | 36 | 287306 | 38164 | 13 |
| 25 | 608014 | 40229 | 7 | 297532 | 28067 | 9 | 294331 | 32177 | 11 |
| 12.5 | 465875 | 19562 | 4 | 227115 | 3903 | 2 | 258360 | 9498 | 4 |
| 6.25 | 235674 | 11748 | 5 | 129289 | 7852 | 6 | 128719 | 5700 | 4 |
| 3.125 | 119311 | 6007 | 5 | 71636 | 3954 | 6 | 63621 | 2926 | 5 |
| 1.56 | 60043 | 1953 | 3 | 38843 | 5601 | 14 | 29258 | 2564 | 9 |
| 0.78 | 33801 | 3651 | 11 | 21815 | 4360 | 20 | 13828 | 926 | 7 |
| 0.39 | 43659 | 2315 | 5 | 19629 | 682 | 3 | 16200 | 1553 | 10 |
| 0.195 | 27871 | 5153 | 18 | 11927 | 379 | 3 | 8863 | 501 | 6 |
| 0.098 | 20126 | 6418 | 32 | 7340 | 795 | 11 | 4931 | 377 | 8 |
| 0.049 | 11190 | 1002 | 9 | 5185 | 277 | 5 | 3065 | 359 | 12 |
| 0.024 | 8864 | 1308 | 15 | 4217 | 366 | 9 | 2300 | 776 | 34 |
| 0.012 | 7075 | 406 | 6 | 3770 | 510 | 14 | 1412 | 187 | 13 |
| 0.006 | 6447 | 743 | 12 | 3470 | 136 | 4 | 1120 | 116 | 10 |
| 0 | 5410 | 480 | 9 | 3185 | 211 | 7 | 967 | 272 | 28 |

Example 32

Inhibition of the Diaphorase Reaction by Menadione

Each substrate (PBI-4312, 4550 and 4565) was incubated at 20 μM with 10 μM NADH (Sigma) and 5 u/ml rat diaphorase (Sigma) in a volume of 10 μl 50 mM Tris pH 7.5. Eight identical reactions for each substrate were prepared. The samples were incubated at 5 minutes at room temperature, and 4 of the reactions received 10 μl LDR, and the other 4 reactions received 10 μl LDR with 500 μM menadione. Luciferin generation was monitored over the course of 5 minutes to monitor menadione's inhibition of the diaphorase reaction with each of the 3 substrates. Luminescence was measured, and the RLUs of quadruplicate reactions averaged (Table 4 and FIG. 21). The first reading was taken at approximately one minute after addition of LDR, and the last reading was taken 5 minutes later (~6 minutes).

TABLE 4

| | First Reading | | Last Reading | |
|---|---|---|---|---|
| Compound | Without menadione | With menadione | Without menadione | With menadione |
| 4312 | 5900 | 3527 | 39855 | 5062 |
| 4550 | 16495 | 1786 | 100603 | 2393 |
| 4565 | 564 | 324 | 4407 | 446 |

Example 33

Time Course of the Diaphorase Reaction

Each substrate (PBI-4312, 4550 and 4565) was incubated at 20 μM with 10 μM NADH (Sigma) and 5 u/ml rat diapho-

TABLE 5

| | Avg RLU | | |
|---|---|---|---|
| Reaction time (min) | PBI-4312 | PBI-4550 | PBI-4565 |
| 0 | 7809 | 5965 | 1294 |
| 2 | 150745 | 235195 | 41615 |
| 5 | 206822 | 244517 | 69945 |
| 10 | 305968 | 251968 | 117067 |
| 15 | 366592 | 267318 | 154427 |
| 25 | 499283 | 260601 | 252212 |
| 30 | 529063 | 261773 | 262123 |
| 40 | 544475 | 245014 | 278567 |
| 50 | 599165 | 251575 | 328037 |
| 60 | 571954 | 236357 | 330433 |

Example 34

Fluorescent NADH Detection Assay

Figure 24A:
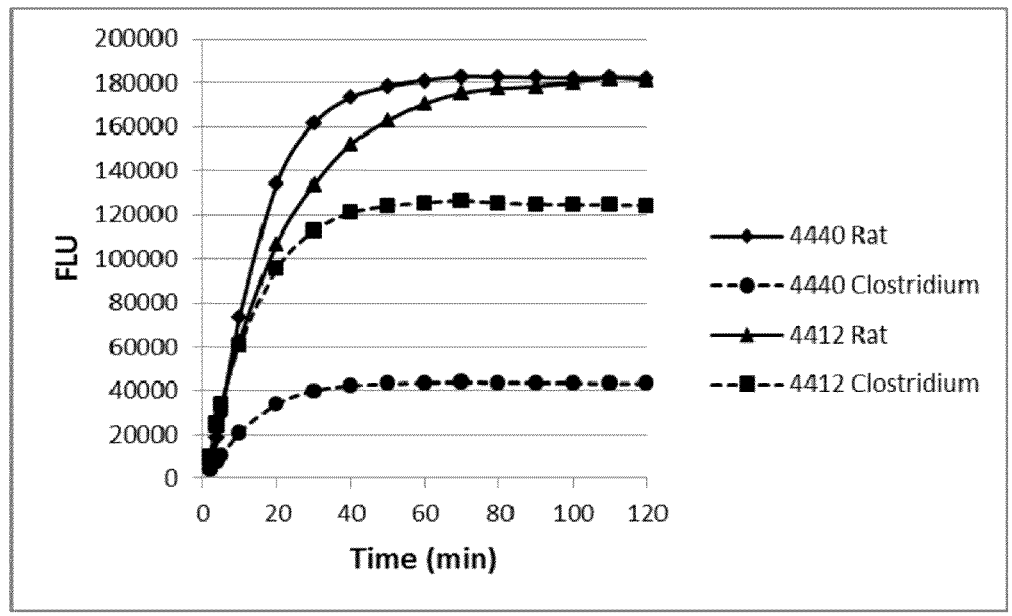
Figure 24B:
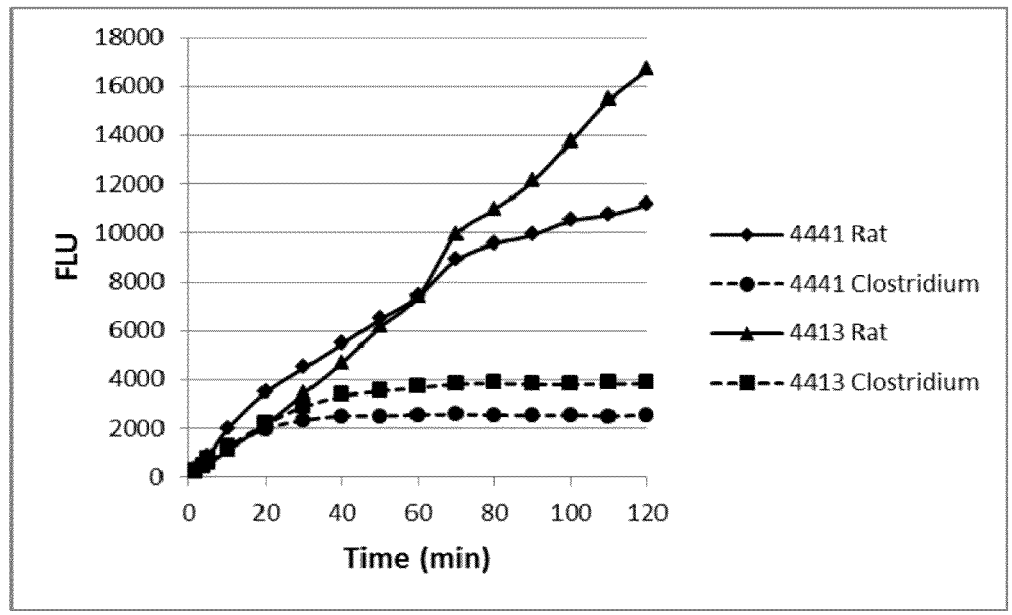

Each fluorescent substrate (PBI-4412, 4413, 4440, and 4441) was incubated at 920 μM with 0 μM or 10 μM NADH (Sigma) or a titration of NADH (Table 8) and 1 u/ml rat diaphorase (Sigma) or 1 u/ml Clostridium diaphorase (Sigma) in a volume of 100 μl in 50 mM Tris pH 7.5. Single reactions were prepared in the wells of a 96-well black plate at room temperature. Fluorescence was monitored over the course of two hours at excitation and emission wavelengths of 485 and 527, respectively, using a fluorescence plate reader. Table 6 and FIG. 23 show that at 60 minutes the fluorescent signal (FLUs) increases when each of the 4 compounds is incubated with 10 μM NADH and either rat diaphorase or Clostridium diaphorase. Table 7 and FIGS. 24a-b show the reaction time course with each substrate with 10 uM NADH. Table 8 and FIG. 25 show the NADH titration at 60 minutes with PBI-4440 and 4412 with rat diaphorase.

TABLE 6

| FLUs | Rat Diaphorase | | | | Clostridium Diaphorase | | | |
| --- | --- | --- | --- | --- | --- | --- | --- | --- |
| | PBI-4440 | PBI-4441 | PBI-4412 | PBI-4413 | PBI-4440 | PBI-4441 | PBI-4412 | PBI-4413 |
| 10 μM NADH | 180909 | 7387 | 170571 | 7397 | 43362 | 2570 | 125352 | 2517 |
| 0 μM NADH | 2922 | 120 | 3772 | 39 | 3050 | 314 | 3940 | 255 |

TABLE 7

| Time | PBI-4440 | | PBI-4412 | | PBI-4441 | | PBI-4413 | |
| --- | --- | --- | --- | --- | --- | --- | --- | --- |
| (min) | Rat | Clostridium | Rat | Clostridium | Rat | Clostridium | Rat | Clostridium |
| 2 | 6473 | 3611 | 10099 | 9933 | 302 | 354 | 180 | 264 |
| 4 | 18626 | 7197 | 24171 | 24883 | 608 | 481 | 419 | 457 |
| 5 | 28997 | 10142 | 33247 | 33881 | 827 | 576 | 545 | 698 |
| 10 | 73216 | 20624 | 62502 | 60458 | 1961 | 1152 | 1091 | 1195 |
| 20 | 133999 | 33781 | 106834 | 95260 | 3454 | 1974 | 2151 | 2167 |
| 30 | 161355 | 39807 | 133278 | 112465 | 4460 | 2334 | 3407 | 2896 |
| 40 | 173345 | 42268 | 151941 | 120688 | 5442 | 2515 | 4669 | 3329 |
| 50 | 178374 | 43000 | 162636 | 123934 | 6457 | 2514 | 6127 | 3519 |
| 60 | 180909 | 43362 | 170571 | 125352 | 7387 | 2570 | 7397 | 3664 |
| 70 | 182618 | 43750 | 175380 | 126364 | 8891 | 2584 | 9925 | 3803 |
| 80 | 182416 | 43425 | 177516 | 125242 | 9545 | 2561 | 10959 | 3841 |
| 90 | 182263 | 43468 | 178423 | 124786 | 9915 | 2539 | 12101 | 3798 |
| 100 | 181996 | 43296 | 180027 | 124434 | 10496 | 2555 | 13732 | 3801 |
| 110 | 182253 | 43005 | 182051 | 124460 | 10736 | 2515 | 15434 | 3820 |
| 120 | 182132 | 43150 | 181077 | 124182 | 11149 | 2570 | 16666 | 3821 |

TABLE 8

| | FLUs | |
| --- | --- | --- |
| NADH (μM) | PBI-4440 | PBI-4412 |
| 80 | 305861 | 183372 |
| 40 | 304293 | 185532 |
| 20 | 309004 | 183286 |
| 10 | 180909 | 170571 |
| 5 | 99331 | 97995 |
| 2.5 | 50387 | 51005 |
| 1.25 | 24788 | 26228 |
| 0 | 2922 | 3772 |

Example 35

Detection of Dehydrogenase Activity Through the Measurement of NADH

To measure the activity of a dehydrogenase by assaying for the production of NADH, reactions containing increasing amounts of dehydrogenase were assembled. The reactions contained isocitrate dehydrogenase (EC 1.1.1.42; Sigma) at concentrations ranging from 0 to 60 nM, 100 μM NADP (Sigma) and 100 μM isocitrate (Sigma). The reactions were in a final volume of 100 μl in buffer 50 mM Tris pH 7.5 1 mM MgCl$_2$. After an incubation of 35 minutes at room temperature, three 25 μl aliquots were removed from each reaction and added to the wells of a 96-well white plate. 25 μl of a mixture of rat (final concentration 5 u/ml) or Clostridium (0.5 u/ml) diaphorase and compound PBI 4312 (final concentration 20 μM) were then added. After 30 minutes at room temperature, 50 μl of LDR was added, and the luminescence measured after 25 minutes using a plate luminometer (Promega). The signals from triplicate wells were averaged (Table 9; FIG. 26a). The signal-to-background ratios (S/B) were calculated by dividing the average signal of samples by the average signal of the wells with 0 nM isocitrate dehydrogenase (Table 9; FIG. 26b).

TABLE 9

| Isocitrate Dehydrogenase | Rat Diaphorase | | Clostridium Diaphorase | |
| --- | --- | --- | --- | --- |
| (nM) | Avg RLU | S/B | Avg RLU | S/B |
| 60 | 19810714 | 181 | 2487241 | 24 |
| 30 | 12649877 | 116 | 1756702 | 17 |
| 15 | 5112106 | 47 | 869482 | 8.3 |
| 7.5 | 22320356 | 20 | 402371 | 3.9 |
| 3.75 | 916791 | 8.4 | 214768 | 2.1 |
| 1.88 | 482006 | 4.4 | 143343 | 1.4 |
| 0.94 | 281161 | 2.6 | 123148 | 1.2 |
| 0.47 | 179081 | 1.6 | 115300 | 1.1 |
| 0.23 | 135578 | 1.2 | 114560 | 1.1 |
| 0.12 | 124743 | 1.1 | 110756 | 1.1 |
| 0.06 | 110787 | 1.0 | 104418 | 1.0 |
| 0 | 109521 | 1.0 | 1042345 | 1.0 |

Example 36

Detection of Dehydrogenase Activity by Measuring NADH

This example demonstrates that the activity of a demethylase enzyme, lysine specific demethylase 1 (LSD1), can be detected by measuring NADH. By combining the demethylase reaction, which produces formaldehyde, with formaldehyde dehydrogenase and NAD+, NADH is generated and can be detected by a method of the present invention (FIG. 27).

LSD1 (0-20 ug/ml) was mixed with H3K4 (me2; 100 μM), formaldehyde dehydrogenase (Pseudomonas; 0.25 U/ml), NAD+ (0.25 mM), Clostridium diaphorase (0.5 U/ml) and compound PBI 4312 (20 μM) in 1×PBS. The reaction was

Example 37

Simultaneous NADH Detection and Light Production

Two fold serial dilutions of NADH (Sigma) were made in PBS starting from 10 µM. 25 ul of each dilution was transferred into wells of a 384-well plates. Detection reagent was made by adding 10 U/ml rat diaphorase (Sigma) and 40 µM proluciferin substrate PBI 4312 into Luciferin Detection Reagent (LDR; Promega Cat. No V8920). 25 µl of detection reagent was added to the NADH samples. The reactions were incubated for 30 minutes at room temperature, and luminescence was measured using a Tecan plate luminometer.

The results show that the diaphorase enzyme remains active in the detection reagent, and the NADH-dependent reduction of the proluciferin by diaphorase into luciferin can occur simultaneously with the luciferin-dependent light-generating luciferase reaction (FIG. 29).

Example 38

NAD Detection and Measurement

Two fold serial dilutions of NAD (Sigma) were made in PBS starting from 0.25 µM. 25 µl of each dilution was transferred into wells of a 384-well plates. Detection reagent was made by adding 10 U/ml rat diaphorase (Sigma), 40 µM proluciferin substrate PBI 4312 and NAD dependent enzyme amplification system consisting of 5 U/ml Lactate Dehydrogenase (Calbiochem) and 40 mM lactate (Sigma) into Luciferin Detection Reagent (LDR; Promega Cat. No V8920). 25 µl of the detection reagent was added to the NAD samples. The reactions were incubated for 30 minutes at room temperature, and luminescence measured using a Tecan plate luminometer.

The following example demonstrates the use of the pro-luciferin substrate PBI-4312 to detect and measure NAD. Luminescence generated is indicative of the presence of NAD with the light output directly proportional to the amount of NAD present in the sample. The results show that the diaphorase and lactate dehydrogenase enzymes remain active in the detection reagent, and all three enzymatic reactions can occur simultaneously (FIG. 30A)

Example 39

NADP Detection and Measurement

Two fold serial dilutions of NADP (Sigma) were made in PBS starting from 0.5 µM. 25 µl of each dilution was transferred into wells of a 384-well plates. Detection reagent was made by adding 10 U/ml rat diaphorase (Sigma), 40 µM proluciferin substrate PBI 4312 and NADP dependent enzyme amplification system consisting of 0.5 U/ml Glucose 6 Phosphate Dehydrogenase (Sigma) and 500 µM glucose 6 phosphate (Sigma) into Luciferin Detection Reagent (LDR; Promega Cat. No V8920). 25µ of detection reagent was added to the NADP samples. The reaction was incubated for 30 minutes at room temperature, and luminescence measured using a Tecan plate luminometer.

The following example demonstrates the use of the pro-luciferin substrate PBI 4312 to detect and measure NADP. Luminescence generated is indicative of the presence of NADP with the light output directly proportional to the amount of NADP present in the sample. The results show that the diaphorase and glucose 6 phosphate dehydrogenase enzymes remain active in detection reagent, and all three enzymatic reactions can occur simultaneously (FIG. 30B).

Example 40

Specificity of Detection Systems

Two fold serial dilutions of NADH, NADPH, NAD, and NADP (Sigma) were made in PBS starting from 0.313 uM. 10 ul of each dilution was transferred into wells of a 384-well plate. Detection reagents were made by adding 10 U/ml of rat diaphorase (Sigma), 40 uM proluciferin substrate PBI 4312 and NADP or NAD dependent enzyme amplification systems consisting of Glucose-6Phosphate Dehydrogenase (5 U/ml) and glucose-6P (0.5 mM) for NADP or Lactate Dehydrogenase (5 U/ml) and Lactate (40 mM) for NAD into Luciferin Detection Reagent (LDR; Promega Cat. No V8920). 10 ul of appropriate detection reagent was added to the dinucleotide samples. The reactions were incubated for 30 minutes at room temperature, and luminescence measured on a Tecan plate luminometer.

The results show that when the detection method described herein is combined with the dinucleotide specific amplification enzyme system, light is generated only in the samples containing appropriate dinucleotide (FIG. 31).

Example 41

Detection of Total Amount of Reduced NADH/NADPH in Cells

Two fold serial dilutions of PC3 cells were made in F12K media with 10% FBS. 25 ul of each dilution was transferred into wells of a 384-well plate. Detection reagent was made by adding 10 U/ml rat diaphorase (Sigma) and 40 µM proluciferin substrate PBI 4312 into Luciferin Detection Reagent (LDR; Promega Cat. No V8920). 25 µl of detection reagent was added directly to the cells. The reactions were incubated for 30 minutes at room temperature, and luminescence measured using a Tecan plate luminometer.

FIG. 32 shows the correlation between cell number and luminescence indicating a direct relationship between luminescence generated via proluciferin conversion and the total amount of reduced dinucleotides NADH/NADPH present in the cells. The results also show that detection system comprised of diaphorase and pro-luciferin PBI 4312 combined with Luciferase Detection Reagent (LDR) can be added directly to the cells to measure the amount of reduced dinucleotides present in the cells.

Example 42

Detection of Total Amount of Oxidized and Reduced Dinucleotides in Cells

Two fold serial dilutions of PC3 cells were made in F12K media with 10% FBS. 25 ul of each dilution was transferred into wells of a 384-well plate. For measuring total amount of NAD/NADH, detection reagent was made by adding 10 U/ml of rat diaphorase (Sigma), 40 µM proluciferin substrate PBI 4312, 5 U/ml of Lactate Dehydrogenase (Calbiochem) and 40 mM lactate (Sigma) into Luciferin Detection Reagent (LDR; Promega Cat. No V8920). For measuring total amount of NADP/NADPH, detection reagent was made by adding 10 U/ml of rat diaphorase (Sigma), 40 µM proluciferin substrate PBI 4312, 0.5 U/ml of Glucose 6 Phosphate Dehydrogenase (Sigma) and 0.5 mM glucose 6 phosphate (Sigma) into Luciferin Detection Reagent (LDR; Promega Cat. No V8920). 25 µl of appropriate detection reagent was added to the cells. The reactions were incubated for 30 minutes at room temperature, and luminescence measured using a Tecan plate luminometer.

The results show that a detection system comprised of an amplification enzyme system (amplification enzyme+its substrate), diaphorase and proluciferin PBI 4312 can be combined with Luciferase Detection Reagent (LDR) and added directly to the cells to measure the amount of dinucleotides present in the cells. FIG. 33 shows the correlation between cell number and luminescence indicating a direct relationship between luminescence generated via proluciferin conversion and the amount of total NAD/NADH(a) or NADP/NADPH (b) present in the cells.

Example 43

Monitoring Inhibition of NAD Biosynthesis

Cells were plated at 7.5×103 cells/12.5 ul into wells of a 384-well plates. The cells were plated in full media containing 10% FBS (PC3 and A549 cells in F12K; Hela, MD-AMB and HET116 cells in DMEM without pyruvate; HepG2 cells in E-MEM and Jurkat cells in RPMI). Two fold serial dilution of FK866 (a known inhibitor of NAD biosynthesis pathway) was made in appropriate media for each cell line, and 12.5 ul added to the cells. The cells were placed in a $CO_2$ dependent incubator. After 48 hours of treatment, the plates were removed from the incubator, and 25 ul of detection reagent consisting of 10 U/ml of rat diaphorase, 40 uM proluciferin substrate PBI 4312, 10 U/ml Lactate Dehydrogenase and 40 mM Lactate in Luciferin Detection Reagent (LDR; Promega Cat. No V8920) was added to each well. The reaction was incubated for 30 minutes at room temperature, and luminescence measured using a Tecan plate luminometer. The data are shown as % inhibition compared to control (no inhibitor) and are plotted using the sigmoidal dose-response, variable slope model supplied with SigmaPlot 11.0 software. A signal-to-background ratio (S/B) calculated between control cells and cells treated with the highest FK866 concentration.

The results show the decrease in NAD levels induced by FK866 can be monitored using the method described herein (FIG. 34).

Example 44

Measuring Total NAD+NADH from Rat Red Blood Cells

An equal volume of rat whole blood (Bioreclaimation) was layered over Histopaque 1083 (Sigma) and centrifuged at 400×g for 30 min. The supernatant over the pelleted red blood cells (RBCs) was aspirated. The pelleted cells were washed twice with PBS+5% FBS (Hyclone) followed by re-suspension of the RBCs in PBS. Equal volumes of serially diluted RBCs and LDR reagent with 10 U/ml diaphorase, 40 uM proluciferin PBI 4312, 8 mM lactate, and 10 U/ml LDH were added to wells of a 96-well plate and incubated at room temperature for 30 minutes. Luminescence was measured on a Turner luminometer.

The results show that the total amount of NAD/NADH can be measured in red blood cells using the method described herein (FIG. 35).

Example 45

Monitoring Drug Induced Changes in Total NAD(P)/NAD(P)H Levels

HepG2 cells were plated into wells of a 384-well plate at 5,000 cells/well in 25 ul of RPMI media containing 22 mM glucose or 10 mM galactose as an energy source. The cells were treated with 1 uM mitochondrial toxin antimycin or rotenone. At 4 and 24 hours after drug treatment, 25 ul of appropriate detection reagent was added to the cells. The NADH/NADPH detection reagent contained 10 U/ml rat diaphorase, 32 uM proluciferin substrate PBI 4312, 0.5 U/ml Glucose-6-Phosphate Dehydrogenase and 0.4 mM glucose-6-phosphate into Luciferin Detection Reagent. The NAD/NADH detection reagent contained 10 U/ml of rat diaphorase, 32 uM proluciferin substrate PBI 4312, 10 U/ml Lactate Dehydrogenase and 40 mM Lactate in Luciferin Detection Reagent. The reactions were incubated for 30 minutes at room temperature, and luminescence measured using a Tecan plate luminometer. The data are shown as % of dinucleotides remaining in the cells after treatment compared to untreated cells.

The results show that drug induced changes in cellular NAD(P)/NAD(P)H levels can be measured using the method described herein (FIG. 36).

Example 46

Cycling Reactions: Kinetic Measurement and Measurement after Adding Menadione

50 µl of NAD(Sigma) or NADP (Sigma) dilutions were made in PBS. NAD detection reagent was made by adding 10 U/ml rat diaphorase (Sigma), 40 µM proluciferin substrate PBI 4312, 5 U/ml Lactate Dehydrogenase (Calbiochem) and 40 mM lactate (Sigma) into reconstituted Luciferin Detection Reagent (LDR; Promega Cat. No V8920). NADP detection reagent was made by adding 10 U/ml rat diaphorase (Sigma), 40 µM proluciferin substrate PBI 4312, 0.5 U/ml Glucose-6-Phosphate Dehydrogenase (Sigma) and 500 µM Glucose-6-Phosphate (Sigma) into reconstituted Luciferin Detection Reagent (LDR; Promega Cat. No V8920). 50 µl of the appropriate detection reagent was added to the NAD or NADP dilutions. Luminescence was monitored approximately every 5 minutes. At the 25 minute time point, 10 µl of 2.75 mM Menadione (Sigma) was added to three wells of each dilution. Luminescence continued to be monitored at 5 minute and 10 minute intervals. Six repeats were used for each experiment.

The results show that luminescence continues to increase with time as the reaction cycles between oxidized and reduced forms of the dinucleotides resulting in the release of free luciferin. When all of the proluciferin has been converted to luciferin, luminescence will no longer increase. Menadione added at the desired time stops production of the light signal, thereby allowing the light signals to be read at a later time (FIG. 37).

Example 47

Measuring Oxidation of Reduced Dinucleotides

The assay was performed in two steps. 20 uM NADPH and 20 uM NADP stocks were made in PBS and mixed at different ratios to mimic the conversion of NADPH to NADP by enzymatic reaction. For example, 40% NADP sample contained 60% NADPH, 20% NADP sample contained 80% NADPH, etc. In the first step, 5 ul of 0.5N HCl was added to 10 ul the pre-made NADPH-NADP mixtures, and the samples incubated for 30 minutes at room temperature. Detection reagent was made by adding 10 U/ml of rat diaphorase, 40 uM proluciferin substrate PBI 4312, 0.5 U/ml of Glucose-6-Phosphate Dehydrogenase and 0.5 mM glucose-6-Phosphate into Luciferin Detection Reagent. 5 ul of buffer containing 20 mM $NaHCO_3$ and 100 mM $Na_2CO_3$ was added to 20 ul of detection reagent, and the prepared mixture added to the acid treated NADPH-NADP samples. The reactions were incubated for 30 minutes at room temperature, and luminescence measured using a Tecan plate luminometer.

The results show that reduced forms of dinucleotides can be selective destroyed by acid treatment and the amount of NADPH converted to NAD can be determined by measuring NAD production. The assay sensitivity allowed detecting 5-10% conversion of NADPH to NADP (FIG. 38).

Example 48

Acid Extraction of a Mixture of Oxidized and Reduced Dinucleotides Removes the Reduced Form and Allows Measurement of the Oxidized Form NAD (Sigma) and NADH (Sigma) samples were prepared at 125 μM and 250 μM in PBS. Equal volumes of NAD and NADH were mixed to prepare a sample containing both dinucleotides. 20 μl of each sample was added to 8 wells of a 384-well white luminometer plate. 10 μl of 0.3N hydrochloric acid was added to 4 of the 8 wells. After 15 minutes, 10 μl of 0.3N sodium hydroxide base was added to neutralize the acid. This step was followed by the addition of 40 μl of NAD detection reagent. Wells not acid treated received 40 μl of NAD detection reagent and 20 μl premixed 0.3N acid and 0.3 N base. The NAD detection reagent was 10 U/ml diaphorase (Sigma), 40 μM proluciferin substrate PBI 4312, 5 u/ml lactate dehydrogenase (Calbiochem) and 40 mM lactate (Sigma) in reconstituted Luciferin Detection Reagent (LDR; Promega Cat. No V8920). Luminescence was measured at 60 minutes using a Tecan Luminometer. The results, in Table 10, show that the acid treatment destroys NADH, but not NAD. This allows for the measurement of NAD in a sample that contains both NADH and NAD. The ratio of NAD to NADH can be determined using the formula: signal from acid treated sample divided by (signal from no acid treatment sample minus signal from acid treated sample). The calculation for this data is in Table 11.

In addition to purified dinucleotide samples, 10,000 Jurkat cells in PBS were also added to 16 wells. 8 wells were acid treated and 8 were not following the protocol above. The results of these samples and calculations are in Table 12.

TABLE 10

| | Average relative Light Units (RLU) | | | | | |
|---|---|---|---|---|---|---|
| | No Acid Treatment | | | Acid Treatment | | |
| | NAD | NADH | NAD + NADH | NAD | NADH | NAD + NADH |
| 250 nM | 391,458 | 457,580 | 417,911 | 433,471 | 25002 | 211841 |
| 125 nM | 202,591 | 205,932 | 205,284 | 216,075 | 15,589 | 104,463 |

TABLE 11

| | |
|---|---|
| No acid treatment sample of 1:1 mix of 250 μM NAD:250 μM NADH | 417,911 RLU |
| Acid treatment sample of 1:1 mix of 250 μM NAD:250 μM NADH | 211,841 RLU |
| Difference | 206,070 RLU |
| Ratio of NAD to NADH determined using the formula: signal from acid treated sample divided by (signal from no acid treatment sample minus signal from acid treated sample) | 1.03 |

TABLE 12

| | No Acid Treatment of 10,000 Jurkat Cells | Acid Treatment of 10,000 Jurkat Cells | Difference | Ratio |
|---|---|---|---|---|
| Average RLU | 175,463 | 119,416 | 56047 | 2.1 |
| Standard Deviation | 11,249 | 10,297 | | |

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A compound is of Formula (IV):

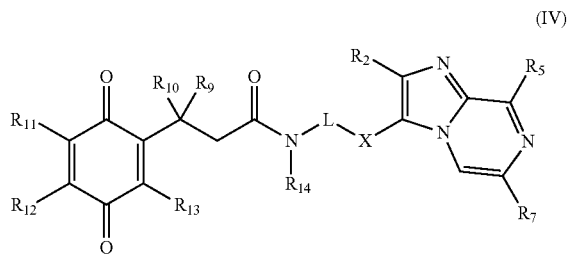

wherein $R_2$ is selected from —$CH_2$-aryl or —$CH_2$-heteroaryl;

$R_5$ is selected from —$CH_2$-aryl or —$CH_2$-heteroaryl;

$R_7$ is selected from aryl or heteroaryl;

$R_{14}$ is H, $C_{1-4}$ alkyl, $C_{1-4}$ alkoxyl, $C_{2-4}$ hydroxylalkyl, $C_{2-4}$alkoxyl, $C_{2-4}$ carboxylic acid, or $C_{2-4}$ amide;

$R_9$ and $R_{10}$ are independently selected from $C_{1-4}$ alkyl;

$R_{11}$, $R_{12}$ and $R_{13}$ are independently selected from H, $C_{1-4}$ alkyl, $C_{1-4}$ alkoxyl, bromo, chloro or amino, or $R_{11}$ and $R_{12}$ can form a fused phenyl ring;

X is O, NH or a direct bond;
L is a direct bond or —C$_6$(R$_{16}$)$_4$CH$_2$— or —(CH$_2$)$_m$C(R$_{17}$)$_2$(CH$_2$)$_n$—Y—C(O)—;
R$_{16}$ is independently H, halogen, CH$_3$, OCH$_3$, or NO$_2$;
R$_{17}$ is independently H, C$_{1-4}$ alkyl; or both R$_{17}$ together can form an alkyl ring having from 3-7 carbons;
m is an integer from 0-2;
n is an integer from 0-2;
Y is O or NR$_{15}$; and
R$_{15}$ is H, C$_{1-4}$ alkyl, C$_{2-4}$ hydroxylalkyl, C$_{2-4}$ alkoxyl, C$_{2-4}$ carboxylic acid, or C$_{2-4}$ amide.

2. A kit comprising a compound according to claim 1.

3. A compound is of Formula (II):

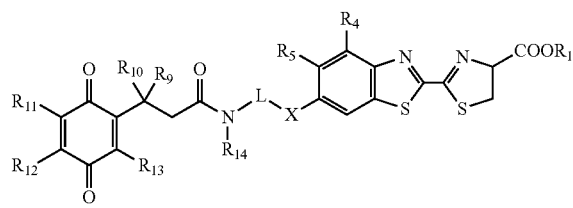
(II)

wherein R$_1$ is H, C$_{1-4}$ alkyl, C$_{1-4}$ hydroxylalkyl, C$_{3-7}$ cyclic ring, aryl, benzyl or substituted benzyl ring, heterocycle, heteroaryl and —(CH$_2$)$_n$—P(Ph)$_3$;
R$_4$ and R$_5$ are independently selected from H, halogen, methyl, and trifluoromethyl;
R$_{14}$ is H, C$_{1-4}$ alkyl, C$_{1-4}$ alkoxyl, C$_{2-4}$ hydroxylalkyl, C$_{2-4}$ alkoxyl, C$_{2-4}$ carboxylic acid, or C$_{2-4}$ amide;
R$_9$ and R$_{10}$ are independently selected from C$_{1-4}$ alkyl;
R$_{11}$, R$_{12}$ and R$_{13}$ are independently selected from H, C$_{1-4}$ alkyl, C$_{1-4}$ alkoxyl, bromo, chloro or amino, or R$_{11}$ and R$_{12}$ can form a fused phenyl ring;
X is O, NH or a direct bond;
L is a direct bond or —C$_6$(R$_{16}$)$_4$CH$_2$— or —(CH$_2$)$_m$C(R$_{17}$)$_2$(CH$_2$)$_n$—Y—C(O)—;
wherein at least one of X or L is not a direct bond;
R$_{16}$ is independently H, halogen, CH$_3$, OCH$_3$, or NO$_2$;
R$_{17}$ is independently H, C$_{1-4}$ alkyl or both R$_{17}$ together form an alkyl ring having from 3-7 carbons;
m is an integer from 0-2;
n is an integer from 0-2;
Y is O or NR$_{15}$; and
R$_{15}$ is H, C$_{1-4}$ alkyl, C$_{2-4}$ hydroxylalkyl, C$_{2-4}$ alkoxyl, C$_{2-4}$ carboxylic acid, or C$_{2-4}$ amide;
n' is an integer from 2-7.

4. The compound according to Formula (III):

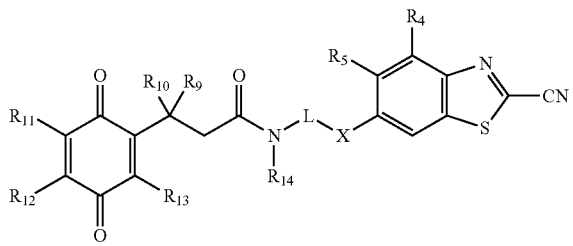
(III)

wherein R$_4$ and R$_5$ are independently selected from H, halogen, methyl, and trifluoromethyl;
R$_{14}$ is H, C$_{1-4}$ alkyl, C$_{1-4}$ alkoxyl, C$_{2-4}$ hydroxylalkyl, C$_{2-4}$ alkoxyl, C$_{2-4}$ carboxylic acid, or C$_{2-4}$ amide;
R$_9$ and R$_{10}$ are independently selected from C$_{1-4}$ alkyl;
R$_{11}$, R$_{12}$ and R$_{13}$ are independently selected from H, C$_{1-4}$ alkyl, C$_{1-4}$ alkoxyl, bromo, chloro or amino, or R$_{11}$ and R$_{12}$ can form a fused phenyl ring;
X is O, NH or a direct bond;
L is a direct bond or —C$_6$(R$_{16}$)$_4$CH$_2$— or —(CH$_2$)$_m$C(R$_{17}$)$_2$(CH$_2$)$_n$—Y—C(0)—;
R$_{16}$ is independently H, halogen, CH$_3$, OCH$_3$, or NO$_2$;
R$_{17}$ is independently H, C$_{1-4}$ alkyl or both R$_{17}$ together form an alkyl ring having from 3-7 carbons;
m is an integer from 0-2;
n is an integer from 0-2;
Y is O or NR$_{15}$; and
R$_{15}$ is H, C$_{1-4}$ alkyl, C$_{2-4}$ hydroxylalkyl, C$_{2-4}$ alkoxyl, C$_{2-4}$ carboxylic acid, or C$_{2-4}$ amide.

5. A kit comprising a compound according to claim 3.

6. A kit comprising a compound according to claim 4.

7. A compound selected from the group consisting of:

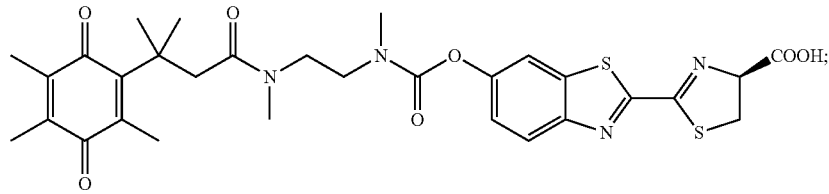
PBI 4312

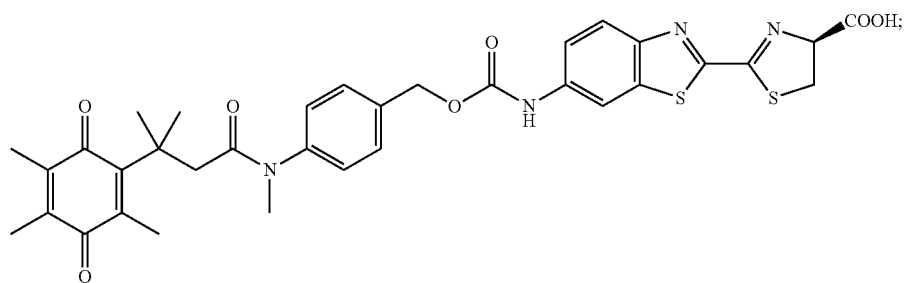
PBI 4550

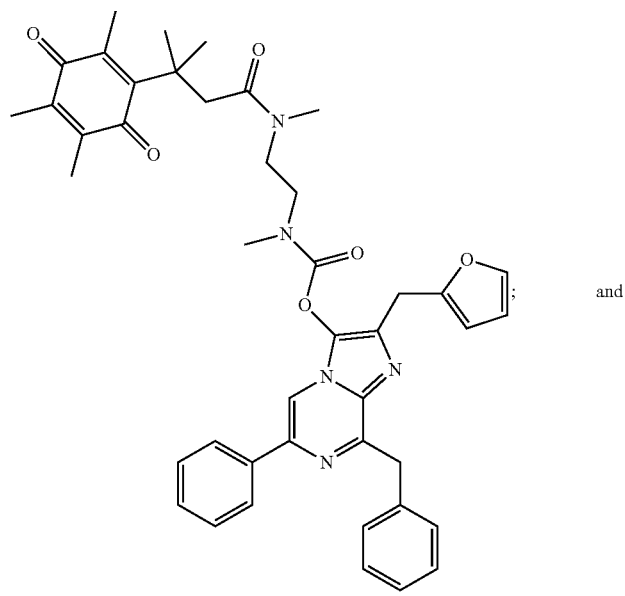
PBI 4600
and
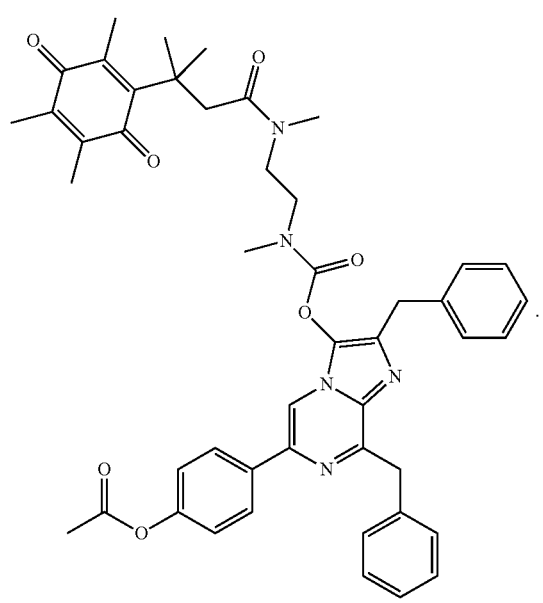
PBI 4442
* * * * *